US010836741B2

(12) United States Patent
Ioannidis et al.

(10) Patent No.: US 10,836,741 B2
(45) Date of Patent: Nov. 17, 2020

(54) QUINAZOLINONES AND AZAQUINAZOLINONES AS UBIQUITIN-SPECIFIC PROTEASE 7 INHIBITORS

(71) Applicant: Valo Early Discovery, Inc., Boston, MA (US)

(72) Inventors: Stephanos Ioannidis, Natick, MA (US); Adam Charles Talbot, Watertown, MA (US); Bruce Follows, Littleton, MA (US); Alexandre Joseph Buckmelter, Acton, MA (US); Minghua Wang, Acton, MA (US); Ann-Marie Campbell, Monroe, CT (US); David R. Lancia, Jr., Boston, MA (US)

(73) Assignee: Valo Early Discovery, Inc., Boston, MA (US)

(*) Notice: Subject to any disclaimer, the term of this patent is extended or adjusted under 35 U.S.C. 154(b) by 0 days.

(21) Appl. No.: 16/694,500

(22) Filed: Nov. 25, 2019

(65) Prior Publication Data

US 2020/0087280 A1 Mar. 19, 2020

Related U.S. Application Data

(63) Continuation of application No. 15/837,393, filed on Dec. 11, 2017, now Pat. No. 10,513,507, which is a continuation of application No. 15/015,571, filed on Feb. 4, 2016, now Pat. No. 9,840,491.

(60) Provisional application No. 62/112,487, filed on Feb. 5, 2015.

(51) Int. Cl.
*C07D 401/06* (2006.01)
*C07D 239/88* (2006.01)
*C07D 487/04* (2006.01)
*C07D 471/04* (2006.01)

(52) U.S. Cl.
CPC ......... *C07D 401/06* (2013.01); *C07D 239/88* (2013.01); *C07D 471/04* (2013.01); *C07D 487/04* (2013.01)

(58) Field of Classification Search
CPC .................................................. C07D 401/06
See application file for complete search history.

(56) References Cited

U.S. PATENT DOCUMENTS

| | | | |
|---|---|---|---|
| 4,895,841 A | 1/1990 | Sugimoto et al. |
| 5,100,901 A | 3/1992 | Sugimoto et al. |
| 5,124,335 A | 6/1992 | Patchett et al. |
| 5,656,627 A | 8/1997 | Bemis et al. |
| 5,716,929 A | 2/1998 | Bemis et al. |
| 5,756,466 A | 5/1998 | Bemis et al. |
| 5,847,135 A | 12/1998 | Bemis et al. |
| 5,874,424 A | 2/1999 | Batchelor et al. |
| 5,973,111 A | 10/1999 | Bemis et al. |
| 5,985,863 A | 11/1999 | Su et al. |
| 6,008,217 A | 12/1999 | Batchelor et al. |
| 6,103,711 A | 8/2000 | Bemis et al. |
| 6,204,261 B1 | 3/2001 | Batchelor et al. |
| 6,258,948 B1 | 7/2001 | Batchelor et al. |
| 6,420,522 B1 | 7/2002 | Bemis et al. |
| 6,423,840 B1 | 7/2002 | Batchelor et al. |
| 6,432,964 B1 | 8/2002 | Atherall et al. |
| 6,444,816 B1 | 9/2002 | Das et al. |
| 6,482,838 B2 | 11/2002 | Pratt |
| 6,506,771 B2 | 1/2003 | Pinto et al. |
| 6,541,630 B1 | 4/2003 | Atherall et al. |
| 6,576,646 B1 | 6/2003 | Pratt |
| 6,632,815 B2 | 10/2003 | Zhu et al. |
| 6,686,368 B1 | 2/2004 | Zhu et al. |
| 6,689,795 B2 | 2/2004 | Pratt |
| 6,720,317 B1 | 4/2004 | Zhu et al. |
| 6,943,253 B2 | 9/2005 | Vidal Juan et al. |
| 6,960,595 B2 | 11/2005 | Pinto et al. |
| 6,964,957 B2 | 11/2005 | Abreo et al. |
| 7,253,204 B2 | 8/2007 | Delorme et al. |
| 7,285,565 B2 | 10/2007 | Zhu et al. |
| 7,288,624 B2 | 10/2007 | Bemis et al. |
| 7,557,113 B2 | 7/2009 | Tsutsumi et al. |
| 7,563,808 B2 | 7/2009 | Pratt |
| 7,601,728 B2 | 10/2009 | Nakahira et al. |
| 7,745,447 B2 | 6/2010 | Washburn et al. |
| 7,772,366 B2 | 8/2010 | Bemis et al. |

(Continued)

FOREIGN PATENT DOCUMENTS

CN 103833646 A 6/2014
EP 1460077 A1 9/2004

(Continued)

OTHER PUBLICATIONS

Banker, et. al., Modern Pharmaceuticals, 596 (1996).

(Continued)

*Primary Examiner* — Paul V Ward
(74) *Attorney, Agent, or Firm* — Choate, Hall & Stewart LLP; Michael A. Shinall; Nicholas J. Pace

(57) ABSTRACT

The present disclosure relates to inhibitors of USP7 inhibitors useful in the treatment of cancers, neurodegenerative diseases, immunological disorders, inflammatory disorders, cardiovascular diseases, ischemic diseases, viral infections and diseases, and bacterial infections and diseases, having the Formula:

where $R_1$, $R_2$, $R_3$, $R_4$, $R_{4'}$, $X_1$, $Y_1$, $Y_2$, $Y_3$, $Y_4$, n, and m are described herein.

28 Claims, No Drawings

(56) References Cited

U.S. PATENT DOCUMENTS

| | | |
|---|---|---|
| 7,790,713 B2 | 9/2010 | Batchelor et al. |
| 7,816,363 B2 | 10/2010 | Angibaud et al. |
| 7,868,205 B2 | 1/2011 | Moradei et al. |
| 7,932,246 B2 | 4/2011 | Moffat et al. |
| 7,989,445 B2 | 8/2011 | Murata et al. |
| 8,084,459 B2 | 12/2011 | Kok et al. |
| 8,088,805 B2 | 1/2012 | Delorme et al. |
| 8,119,631 B2 | 2/2012 | Batchelor et al. |
| 8,133,998 B2 | 3/2012 | Pajouhesh et al. |
| 8,268,833 B2 | 9/2012 | Angibaud et al. |
| 8,343,988 B2 | 1/2013 | Angibaud et al. |
| 8,575,114 B2 | 11/2013 | Liu et al. |
| 8,586,619 B2 | 11/2013 | Wu et al. |
| 8,618,115 B2 | 12/2013 | Washburn et al. |
| 8,642,609 B2 | 2/2014 | Makings et al. |
| 8,765,773 B2 | 7/2014 | England et al. |
| 8,841,289 B2 | 9/2014 | Ratcliffe et al. |
| 8,859,566 B2 | 10/2014 | Palle et al. |
| 8,927,718 B2 | 1/2015 | Sasaki et al. |
| 9,260,448 B2 | 2/2016 | Choo et al. |
| 9,273,068 B2 | 3/2016 | Geneste et al. |
| 9,284,297 B2 | 3/2016 | Keller et al. |
| 9,546,150 B2 | 1/2017 | Colland et al. |
| 9,840,491 B2 | 12/2017 | Ioannidis et al. |
| 9,902,728 B2 | 2/2018 | Ioannidis et al. |
| 9,932,351 B2 | 4/2018 | Ioannidis et al. |
| 9,938,300 B2 | 4/2018 | Ioannidis et al. |
| 10,000,495 B2 | 6/2018 | Ioannidis et al. |
| 10,351,571 B2 | 7/2019 | Ioannidis et al. |
| 10,377,760 B2 | 8/2019 | Ioannidis et al. |
| 10,377,767 B2 | 8/2019 | Ioannidis et al. |
| 10,377,773 B2 | 8/2019 | Ioannidis et al. |
| 10,508,098 B2 | 12/2019 | Ioannidis et al. |
| 10,513,507 B2 | 12/2019 | Ioannidis et al. |
| 10,513,508 B2 | 12/2019 | Ioannidis et al. |
| 10,519,127 B2 | 12/2019 | Ioannidis et al. |
| 10,519,128 B2 | 12/2019 | Ioannidis et al. |
| 10,519,129 B2 | 12/2019 | Ioannidis et al. |
| 10,519,130 B2 | 12/2019 | Ioannidis et al. |
| 2002/0035128 A1 | 3/2002 | Pratt |
| 2002/0132319 A1 | 9/2002 | Abreo et al. |
| 2002/0169175 A1 | 11/2002 | Gaddam et al. |
| 2003/0153598 A1 | 8/2003 | Pratt |
| 2003/0225269 A1 | 12/2003 | Batchelor et al. |
| 2004/0038994 A1 | 2/2004 | Wilson |
| 2004/0039012 A1 | 2/2004 | Wilson |
| 2004/0116399 A1 | 6/2004 | Zhu et al. |
| 2004/0132732 A1 | 7/2004 | Han et al. |
| 2004/0180931 A1 | 9/2004 | Pratt |
| 2004/0192732 A1 | 9/2004 | Pratt et al. |
| 2004/0214863 A1 | 10/2004 | Pratt |
| 2005/0143436 A1 | 6/2005 | Batchelor et al. |
| 2005/0148534 A1 | 7/2005 | Castellino et al. |
| 2005/0153992 A1 | 7/2005 | Tsutsumi et al. |
| 2005/0250812 A1 | 11/2005 | Pratt |
| 2006/0018839 A1 | 1/2006 | Ieni et al. |
| 2006/0135507 A1 | 6/2006 | Yokoyama et al. |
| 2006/0172992 A1 | 8/2006 | Yokoyama et al. |
| 2006/0183776 A9 | 8/2006 | Pratt |
| 2006/0234909 A1 | 10/2006 | Newman et al. |
| 2007/0053976 A1 | 3/2007 | Sakai et al. |
| 2008/0045500 A1 | 2/2008 | Teramoto et al. |
| 2008/0064680 A1 | 3/2008 | Bamdad |
| 2008/0119457 A1 | 5/2008 | Huang et al. |
| 2008/0167343 A1 | 7/2008 | Ieni et al. |
| 2008/0312189 A1 | 12/2008 | Pratt |
| 2008/0318922 A1 | 12/2008 | Nakahira et al. |
| 2009/0042939 A1 | 2/2009 | Ieni et al. |
| 2009/0042940 A1 | 2/2009 | Ieni et al. |
| 2009/0118261 A1 | 5/2009 | Aquila et al. |
| 2009/0192129 A1 | 7/2009 | Nakahira et al. |
| 2009/0192138 A1 | 7/2009 | Baeschlin et al. |
| 2009/0253704 A1 | 10/2009 | Koltun et al. |
| 2011/0015193 A1 | 1/2011 | Eickmeier et al. |
| 2011/0015371 A1 | 1/2011 | Bemis et al. |
| 2011/0053981 A1 | 3/2011 | Ieni et al. |
| 2011/0082158 A1 | 4/2011 | Gangjee et al. |
| 2011/0184000 A1 | 7/2011 | Giovannini et al. |
| 2011/0263532 A1 | 10/2011 | Keller et al. |
| 2012/0122889 A1 | 5/2012 | Yuan et al. |
| 2012/0165319 A1 | 6/2012 | Batchelor et al. |
| 2012/0238749 A1 | 9/2012 | Bemis et al. |
| 2013/0085133 A1 | 4/2013 | Severson et al. |
| 2013/0116241 A1 | 5/2013 | Geneste et al. |
| 2013/0303551 A1 | 11/2013 | Adams et al. |
| 2014/0024657 A1 | 1/2014 | Yuan et al. |
| 2014/0213779 A1 | 7/2014 | Dixon et al. |
| 2016/0185785 A1 | 6/2016 | Ioannidis et al. |
| 2016/0185786 A1 | 6/2016 | Ioannidis et al. |
| 2016/0229833 A1 | 8/2016 | Ioannidis et al. |
| 2016/0229864 A1 | 8/2016 | Ioannidis et al. |
| 2016/0229872 A1 | 8/2016 | Ioannidis et al. |
| 2018/0162835 A1 | 6/2018 | Ioannidis et al. |
| 2018/0339988 A1 | 11/2018 | Ioannidis et al. |
| 2018/0339991 A1 | 11/2018 | Ioannidis et al. |
| 2018/0346480 A1 | 12/2018 | Ioannidis et al. |
| 2018/0346485 A1 | 12/2018 | Ioannidis et al. |
| 2019/0071418 A1 | 3/2019 | Ioannidis et al. |
| 2019/0071419 A1 | 3/2019 | Ioannidis et al. |
| 2019/0071420 A1 | 3/2019 | Ioannidis et al. |
| 2019/0071421 A1 | 3/2019 | Ioannidis et al. |
| 2019/0071422 A1 | 3/2019 | Ioannidis et al. |
| 2019/0071423 A1 | 3/2019 | Ioannidis et al. |
| 2019/0308980 A1 | 10/2019 | Ioannidis et al. |
| 2019/0359629 A1 | 11/2019 | Ioannidis et al. |
| 2019/0359635 A1 | 11/2019 | Ioannidis et al. |
| 2019/0367525 A1 | 12/2019 | Ioannidis et al. |

FOREIGN PATENT DOCUMENTS

| | | |
|---|---|---|
| EP | 2 565 186 A1 | 3/2013 |
| IN | 151496 B | 5/1983 |
| JP | H02-169569 A | 6/1990 |
| JP | 2002105081 A | 4/2002 |
| JP | 2006176503 A | 7/2006 |
| WO | WO-98/02162 A1 | 1/1998 |
| WO | WO-99/08501 A2 | 2/1999 |
| WO | WO-02/16365 A1 | 2/2002 |
| WO | WO-2003/024456 A1 | 3/2003 |
| WO | WO-2003/092606 A2 | 11/2003 |
| WO | WO-2004/037176 A2 | 5/2004 |
| WO | WO-2004/058727 A1 | 7/2004 |
| WO | WO-2005/019219 A1 | 3/2005 |
| WO | WO-2005/030704 A1 | 4/2005 |
| WO | WO-2007/053135 A1 | 5/2007 |
| WO | WO-2008/094909 A2 | 8/2008 |
| WO | WO-2008/113255 A1 | 9/2008 |
| WO | WO-2008/116053 A2 | 9/2008 |
| WO | WO-2009/010925 A2 | 1/2009 |
| WO | WO-2009/011617 A2 | 1/2009 |
| WO | WO-2012/075393 A2 | 6/2012 |
| WO | WO-2013/030218 A1 | 3/2013 |
| WO | WO-2013/130660 A1 | 9/2013 |
| WO | WO-2013/140189 A1 | 9/2013 |
| WO | WO-2014/105952 A2 | 7/2014 |
| WO | WO-2016/109480 A1 | 7/2016 |
| WO | WO-2016/109515 A1 | 7/2016 |
| WO | WO-2016/126926 A1 | 8/2016 |
| WO | WO-2016/126929 A1 | 8/2016 |
| WO | WO-2016/126935 A1 | 8/2016 |

OTHER PUBLICATIONS

Corrected Petition for Post Grant Review of U.S. Pat. No. 9,840,491 (PGR2018-00098, Oct. 1, 2018, Paper No. 4).

Database Registry [Online] Chemical Abstracts Service, Columbus, Ohio; Mar. 23, 2009, XP002755482, Data base accession No. 1125429-24-4, the whole document.

Database Registry [Online] Chemical Abstracts Service, Columbus, Ohio; Mar. 23, 2009, XP002755483, Database accession No. 1125419-46-6, the whole document.

(56) References Cited

OTHER PUBLICATIONS

Database Registry [Online] Chemical Abstracts Service, Columbus, Ohio; Jul. 4, 2012 (Jul. 4, 2012), XP002755481, Database accession No. 1381357-58-9.
Database Registry [Online] Chemical Abstracts Service, Columbus, Ohio; Jul. 4, 2012 (Jul. 4, 2012), XP002755499, Database accession No. 1381443-55-5.
Database Registry [Online] Chemical Abstracts Service, Columbus, Ohio; Jul. 4, 2012 (Jul. 4, 2012), XP002755500, Database accession No. 1381443-96-4.
Database Registry [Online] Chemical Abstracts Service, Columbus, Ohio; Jul. 4, 2012 (Jul. 4, 2012), XP002755501, Database accession No. 1381349-35-4.
Database Registry [Online] Chemical Abstracts Service, Columbus, Ohio; Jul. 4, 2012 (Jul. 4, 2012), XP002755502, Database accession No. 1381291-44-6.
Database Registry [Online] Chemical Abstracts Service, Columbus, Ohio; Jul. 4, 2012 (Jul. 4, 2012), XP002755503, Database accession No. 1381280-64-3.
Database Registry [Online] Chemical Abstracts Service, Columbus, Ohio; Jul. 4, 2012 (Jul. 4, 2012), XP002755504, Database accession No. 1381443-88-4.
Decision Granting Institution of Post Grant Review of U.S. Pat. No. 9,840,491 (PGR2018-00098, Mar. 20, 2019, Paper No. 10).
Du, Z. et al. DNMT1 stability is regulated by proteins coordinating deubiquitination and acetylation-driven ubiquitination, Sci. Signal. 3(146) (2010).
Epping M.T., et al. TSPYL5 suppresses p53 levels and function by physical interaction with USP7, Nat. Cell Biol. 13(1):102-108 (2011).
Everett R.D. et al. A novel ubiquitin-specific protease is dynamically associated with the PML nuclear domain and binds to a herpes virus regulatory protein, EMBO J 16(7): 1519-1530 (1997).
Faustrup H. et al. USP7 counteracts SCFβTrCP- but not APC Cdh1-mediated proteolysis of Claspin, J Cell Biol. 184(1):13-19 (2009).
Finley D. Recognition and processing of ubiquitin-protein conjugates by the proteasome Annu. Rev. Biochem. 78:477-513, (2009).
Gao Y. et al. Early adipogenesis is regulated through USP7-mediated deubiquitination of the hi stone acetyltransferase TIP60, Nat. Commun. 4:2656 (2013).
Holowaty M.N. et al. Protein profiling with Epstein-Barr nuclear antigen-I reveals an interaction with the herpesvirus-associated ubiquitin-specific protease HAUSP/USP7, J Biol. Chem. 278(32):29987-29994 (2003).
International Search Report for PCT/US2015/067781, 4 pages (dated Mar. 8, 2016).
International Search Report for PCT/US2015/067831, 4 pages (dated Mar. 23, 2016).
International Search Report for PCT/US2016/016542, 6 pages (dated Apr. 15, 2016).
International Search Report for PCT/US2016/016548, 4 pages (dated Apr. 5, 2016).
International Search Report for PCT/US2016/016556, 3 pages (dated Mar. 23, 2016).
Kessler, B., Selective and reversible inhibitors of ubiquitin-specific protease 7: a patent evaluation, Expert Opinion on Therapeutic Patents, 24(5): 597-602 (2014).
Komander D. The emerging complexity of protein ubiquitination, Biochem. Soc. Trans. 37(Pt 5):937-953 (2009).
Li M. et al. A dynamic role of HAUSP in the p53-Mdm2 pathway, Mal. Cell. 13(6):879-886 (2004).
Li M. et al. Deubiquitination of p53 by HAUSP is an important pathway for p53 stabilization, Nature 416(6881):648-653 (2002).
McMahon et al., VEGF Receptor Signaling in Tumor Angiogenesis, The Oncologist 2000; 5 (suppl 1): 3-10.
Petition for Post Grant Review of U.S. Pat. No. 9,840,491 (PGR2018-00098, Sep. 12, 2018, Paper No. 1).
Pinedo et al. Translational Research: The Role of VEGF in Tumor Angiogenesis, The Oncologist 2000; 5 (Suppl 1):1-2.
Saridakis V., et al. Structure of the p53 binding domain of HAUSP/USP7 bound to Epstein-Barr nuclear antigen 1 implications for EBY-mediated immortalization, Mal. Cell. 18(1):25-36 (2005).
Sarkari F. et al. EBNAI-mediated recruitment of a histone H2B deubiquitylating complex to the Epstein-Barr virus latent origin of DNA replication, PLoS pathoKens 5(10):el 000624 (2009).
Sep. 11, 2018 Declaration of Remi Delansorne, part 1 of 2 (PGR2018-00098, EX-1005).
Sep. 11, 2018 Declaration of Remi Delansorne, part 2 of 2 (PGR2018-00098, EX-1006).
Sheng Y. et al. Molecular recognition of p53 and MDM2 by USP7/HAUSP, Nat. Struct. Mal. Biol. 13(3):285-291 (2006).
Sippl, W. et al. Ubiquitin-specific proteases as cancer drug targets, Future Oncology, vol. 7, No. 5, May 1, 2011, p. 619-632.
Song M.S. et al. The deubiquitinylation and localization of PTEN are regulated by a HAUSP-PML network, Nature 455(7214):813-817 (2008).
Trotman L.C., et al. Ubiquitination regulates PTEN nuclear import and tumor suppression, Cell 128(1): 141-156 (2007).
Turnbull, A.P. et al., Molecular basis of USP7 inhibition by selective small-molecule inhibitors, Nature, 550: 481-486 (2017), 24 pages.
van der Horst A et al. FOX04 transcriptional activity is regulated by monoubiquitination and USP7/HAUSP, Nat. Cell Biol. 8(10): 1064-1073 (2006).
Vippagunta et al. Crystalline Solids, Advanced Drug Delivery Reviews, 48 (2001) 3-26.
West, A.R., Solid State Chemistry and Its Applications, Wiley, New York, Chapter 10: 358 (1988).
Wolff et. al., Burger's Medicinal Chemistry and Drug Discovery, 5th Ed. Part 1: 975-977 (1995).
Written Opinion for PCT/US2015/067781 (Publication WO2016/109480), 6 pages (dated Jul. 7, 2016).
Written Opinion for PCT/US2015/067831 (Publication WO2016/109515), 6 pages (dated Mar. 23, 2016).
Written Opinion for PCT/US2016/016542 (Publication WO2016/126926), 9 pages (dated Aug. 11, 2016).
Written Opinion for PCT/US2016/016548 (Publication WO2016/126929), 9 pages (dated Apr. 15, 2016).
Written Opinion for PCT/US2016/016556, (Publication WO2016/126935), 6 pages (dated Mar. 23, 2016).

QUINAZOLINONES AND AZAQUINAZOLINONES AS UBIQUITIN-SPECIFIC PROTEASE 7 INHIBITORS

RELATED APPLICATIONS

This application is a continuation of U.S. application Ser. No. 15/837,393, filed Dec. 11, 2017, which is a continuation of of U.S. application Ser. No. 15/015,571, filed Feb. 4, 2016, now U.S. Pat. No. 9,840,491, which claims the benefit of and priority to U.S. provisional application No. 62/112,487, filed Feb. 5, 2015, the entire contents of each of which are incorporated herein by reference in its entirety.

FIELD OF DISCLOSURE

The present disclosure is directed to inhibitors of ubiquitin-specific protease 7 (USP7) useful in the treatment of diseases or disorders associated with USP7 enzymes. Specifically, the disclosure is concerned with compounds and compositions inhibiting USP7, methods of treating diseases or disorders associated with USP7, and methods of synthesis of these compounds.

BACKGROUND OF THE DISCLOSURE

Ubiquitination is a post translational modification initially identified as a crucial component of proteasomal degradation in the ubiquitin proteasome system (UPS). Chains of Ubiquitin (Ub(s)), an 8.5 kDa highly conserved protein, are covalently attached to substrates to be degraded in the proteasome. (Finley D. "Recognition and processing of ubiquitin-protein conjugates by the proteasome." *Annual review of biochemistry* 78:477-513, (2009)) The molecular mechanisms by which the UPS acts are also varied, with different chain linkages of ubiquitination controlling protein turnover, enzymatic activity, subcellular localization, and protein-protein interactions of substrate proteins. (Komander D., et. al. "The emerging complexity of protein ubiquitination," *Biochem. Soc. Trans.* 37(Pt 5):937-53 (2009))

Ubiquitin-specific protease 7 (USP7) is a Ubiquitin Specific Protease (USP) family deubiquitinase (DUB) that was originally identified as an enzyme that interacted with virally-encoded proteins of the Herpes simplex virus and later the Epstein-Barr virus. (Everett R. D., Meredith M., Orr A., Cross A, Kathoria M., Parkinson J. "A novel ubiquitin-specific protease is dynamically associated with the PML nuclear domain and binds to a herpes virus regulatory protein," *EMBO J* 16(7):1519-30 (1997); Holowaty M. N., Zeghouf M., Wu H., et al. "Protein profiling with Epstein-Barr nuclear antigen-1 reveals an interaction with the herpesvirus-associated ubiquitin-specific protease HAUSP/USP7," *J. Biol. Chem.* 278(32):29987-94 (2003)) Ubiquitin Specific Proteases (USPs) specifically cleave the isopeptide bond at the carboxy terminus of ubiquitin. In contrast to other DUB classes, which are thought to generally regulate ubiquitin homeostasis or to be involved in pre-processing of linear ubiquitin chains, USPs remove ubiquitin from specific targets. Given this substrate specificity combined with the numerous roles ubiquitination has in the cell, USPs are important regulators of a multitude of pathways, ranging from preventing the proteolysis of ubquitinated substrates, to controlling their nuclear localization.

USP7 deubiquitinates a variety of cellular targets involved in different processes related to cancer and metastasis, neurodegenerative diseases, immunological disorders, osteoporosis, arthritis inflammatory disorders, cardiovascular diseases, ischemic diseases, viral infections and diseases, and bacterial infections and diseases.

For example, USP7 has been shown to stabilize DNMT1, a DNA methyltransferase that maintain epigenetic silencing, to maintain higher steady state-levels of Claspin, a protein involved in ataxia telangiectasia and Rad3-related (ATR) phosphorylation of Chk1, and to regulate Tip60 protein levels, a histone acetyltransferase and transcriptional coregulator involved in adipogenesis. (Zhanwen du, Song J., Wang Y., et al. "DNMT1 stability is regulated by proteins coordinating deubiquitination and acetylation-driven ubiquitination," *Science Signaling* 3(146) (2010); Faustrup H., Bekker-Jensen S., Bartek J., Lukas J., Mail N., Mailand N. "USP7 counteracts SCFbetaTrCP—but not APCCdh1-mediated proteolysis of Claspin," *The Journal of cell biology* 184(1):13-9 (2009); Gao Y., Koppen A., Rakhsh M., et al. "Early adipogenesis is regulated through USP7-mediated deubiquitination of the histone acetyltransferase TIP60," *Nature Communications* 4:2656 (2013)

In addition to regulating the protein stability of poly-ubiquitinated targets, USP7 also acts to control the subcellular localization of proteins. Mono-ubiquitination of PTEN has been shown to effect its cytoplasmic/nuclear partitioning, where nuclear localization of PTEN is important for its tumor suppression activity. (Trotman L. C., Wang X., Alimonti A., et al. "Ubiquitination regulates PTEN nuclear import and tumor suppression," *Cell* 128(1):141-56 (2007); Song M. S., Salmena L., Carracedo A., et al. "The deubiquitinylation and localization of PTEN are regulated by a HAUSP-PML network," *Nature* 455(7214):813-7 (2008)) USP7 has also been shown to bind and deubiquitinate FOXO4, a member of the FOXO subfamily of transcription factors involved in a variety of cell processes including metabolism, cell cycle regulation apoptosis, and response to oxidative stress, decreasing its nuclear localization and transcriptional activity. (van der Horst A., van der Horst O., de Vries-Smits A. M. M., et al. "FOXO4 transcriptional activity is regulated by monoubiquitination and USP7/HAUSP," *Nat. Cell Biol.* 8(10):1064-73 (2006))

Cellular targets of USP7 also include the tumor suppressor p53 and its major E3 ligase, MDM2, stabilizing p53 via the degradation of MDM2. (Li M., Chen D., Shiloh A., et al. "Deubiquitination of p53 by HAUSP is an important pathway for p53 stabilization," *Nature* 416(6881):648-53 (2002); Li M., Brooks C. L., Kon N., Gu W. "A dynamic role of HAUSP in the p53-Mdm2 pathway," *Mol. Cell.* 13(6): 879-86 (2004)) Structural studies have also shown that the EBNA1 protein encoded by the Epstein-Barr virus interacts at the same binding surface as USP7 on p53, preventing USP7 endogenous cellular activity while recruiting USP7 to viral promoters in order to activate latent viral gene expression. (Saridakis V., et al. "Structure of the p53 binding domain of HAUSP/USP7 bound to Epstein-Barr nuclear antigen 1 implications for EBV-mediated immortalization," *Mol. Cell.* 18(1):25-36 (2005); Sarkari F., Sanchez-Alcaraz T., Wang S., Holowaty M. N., Sheng Y., Frappier L. "EBNA1-mediated recruitment of a histone H2B deubiquitylating complex to the Epstein-Barr virus latent origin of DNA replication," *PLoS pathogens* 5(10) (2009); Sheng Y., et al. "Molecular recognition of p53 and MDM2 by USP7/HAUSP," *Nat. Struct. Mol. Biol.* 13(3):285-91 (2006)) Similarly, the gene product of TSPYL5, a gene frequently amplified in breast cancer and associated with poor clinical outcome, alters the ubiquitination status of p53 via its interaction with USP7. (Epping M. T., et al. "TSPYL5 suppresses p53 levels and function by physical interaction with USP7," *Nat. Cell Biol.* 13(1):102-8 (2011))

Inhibition of USP7 with small molecule inhibitors therefore has the potential to be a treatment for cancers and other disorders. For this reason, there remains a considerable need for novel and potent small molecule inhibitors of USP7.

SUMMARY OF THE DISCLOSURE

A first aspect of the disclosure relates to compounds of Formula (I):

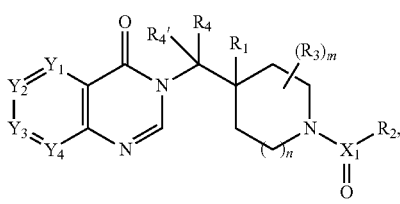

(I)

and pharmaceutically acceptable salts, hydrates, solvates, prodrugs, stereoisomers, and tautomers thereof,
wherein:
$X_1$ is C, S, or S(O);
$Y_1$ is N or CH;
$Y_2$ is N or $CR_5$;
$Y_3$ is N or $CR_6$;
$Y_4$ is N or $CR_7$;
$R_1$ is H, —OH, —SH, —NH$_2$, or F;
$R_2$ is $(C_1$-$C_6)$ alkyl, $(C_6$-$C_{14})$ aryl, heteroaryl, $(C_5$-$C_8)$ cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more $R_8$;
each $R_3$ is independently at each occurrence selected from D, $(C_1$-$C_6)$ alkyl, $(C_6$-$C_{14})$ aryl, heteroaryl, $(C_3$-$C_8)$ cycloalkyl, or heterocycloalkyl, wherein the alkyl, aryl, heteroaryl, cycloalkyl, and heterocycloalkyl are optionally substituted with one or more $R_{20}$; or
two $R_3$ together when on adjacent carbons form a $(C_3$-$C_8)$ cycloalkyl optionally substituted with one or more $R_{20}$; or two $R_3$ together when attached to the same carbon atom form a $(C_3$-$C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;
$R_4$ and $R_4$' are independently H, D, $(C_1$-$C_6)$ alkyl, $(C_2$-$C_6)$ alkenyl, $(C_2$-$C_6)$ alkynyl, $(C_1$-$C_6)$ alkoxy, $(C_1$-$C_6)$ haloalkyl, $(C_1$-$C_6)$ haloalkoxy, halogen, or CN;
$R_5$ is H, $(C_1$-$C_6)$ alkyl, $(C_2$-$C_6)$ alkenyl, $(C_2$-$C_6)$ alkynyl, $(C_1$-$C_6)$ haloalkyl, halogen, NO$_2$, or CN, wherein the alkyl, alkenyl, and alkynyl are optionally substituted with one or more $R_{12}$;
$R_6$ is H, D, $(C_1$-$C_6)$ alkyl, $(C_2$-$C_6)$ alkenyl, $(C_2$-$C_6)$ alkynyl, $(C_1$-$C_6)$ alkoxy, $(C_1$-$C_6)$ haloalkyl, $(C_1$-$C_6)$ haloalkoxy, halogen, CN, NO$_2$, —NH$_2$, —NHC(O)$(C_1$-$C_6)$ alkyl, $(C_6$-$C_{14})$ aryl, heteroaryl, $(C_5$-$C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1$-$C_6)$ alkyl, $(C_6$-$C_{14})$ aryl, heteroaryl, $(C_5$-$C_8)$ cycloalkyl, heterocycloalkyl, —O-aryl, —O-heteroaryl, —N(($C_1$-$C_6)$ alkyl)-aryl, NH-aryl, —N(($C_1$-$C_6)$ alkyl)-heteroaryl, or —NH-heteroaryl, wherein the alkyl, aryl, heteroaryl, cycloalkyl, and heterocycloalkyl are optionally substituted with one or more $R_{14}$;
wherein $R_5$, $R_6$, and $R_7$ are not all simultaneously H;
each $R_8$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —$(C_1$-$C_3)$-alkylene-O—$(C_1$-$C_6)$ alkyl, —$(C_0$-$C_4)$-alkylene-aryl, —$(C_0$-$C_4)$-alkylene-heteroaryl, $(C_3$-$C_{10})$ cycloalkyl, heterocycloalkyl, —$(C_0$-$C_4)$-alkylene-O-aryl, —$(C_0$-$C_4)$-alkylene-O-heteroaryl, —O—$(C_3$-$C_8)$cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O)R$_{22}$, —NR$_{21}$C(O)NR$_{21}$R$_{22}$, —P(O)(($C_1$-$C_6)$ alkyl)$_2$, —P(O)(aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more $R_9$; or
two $R_8$ together when on adjacent atoms form a $(C_3$-$C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;
each $R_9$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, $(C_3$-$C_8)$ cycloalkyl, heterocycloalkyl, —$(C_0$-$C_3)$-alkylene-$(C_6$-$C_{14})$ aryl, —$(C_0$-$C_3)$-alkylene-heteroaryl, —NH$_2$, —OH, —C(O)R$_{23}$, —C(O)NR$_{23}$R$_{24}$, —NR$_{23}$C(O)R$_{24}$, —NR$_{23}$R$_{24}$, —S(O)$_q$R$_{23}$, —S(O)$_q$NR$_{23}$R$_{24}$, —NR$_{23}$S(O)$_q$R$_{24}$, oxo, —P(O)(($C_1$-$C_6)$ alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more $R_{19}$;
$R_{10}$ and $R_{11}$ are independently H, $(C_1$-$C_6)$ alkyl, $(C_6$-$C_{14})$ aryl, heteroaryl, $(C_5$-$C_8)$ cycloalkyl, or heterocycloalkyl, wherein the alkyl, aryl, heteroaryl, cycloalkyl, and heterocycloalkyl are optionally substituted with one or more $R_{17}$; or
$R_{10}$ and $R_{11}$ together with the nitrogen to which they are attached form a heterocycloalkyl ring optionally substituted with one or more $R_{17}$;
each $R_{12}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —C(O)($C_1$-$C_6)$ alkyl, —S(O)$_q$($C_1$-$C_6)$ alkyl, —NH$_2$, $(C_1$-$C_6)$ alkylamino, or di($C_1$-$C_6)$ alkylamino;
each $R_{13}$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —NH$_2$, —C(O)($C_1$-$C_6)$ alkyl, —S(O)$_q$($C_1$-$C_6)$ alkyl, $(C_1$-$C_6)$ alkylamino, di($C_1$-$C_6)$ alkylamino, $(C_6$-$C_{14})$ aryl, heteroaryl, $(C_3$-$C_8)$ cycloalkyl, heterocycloalkyl, —O-aryl, —O-heteroaryl, —O-heterocycloalkyl, —O—$(C_3$-$C_8)$cycloalkyl, —C(O)O($C_1$-$C_6)$ alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O)OR$_{27}$, —NR$_{26}$S(O)$_q$R$_{27}$, —NR$_{26}$C(O)R$_{27}$, halogen, —P(O)(($C_1$-$C_6)$ alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more $R_{15}$;
each $R_{14}$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —NH$_2$, —C(O)($C_1$-$C_6)$ alkyl, —S(O)$_q$($C_1$-$C_6)$ alkyl, $(C_1$-$C_6)$ alkylamino, di($C_1$-$C_6)$ alkylamino, $(C_6$-$C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —C(O)O$(C_1-C_6)$ alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O)OR$_{27}$, —NR$_{26}$S(O)$_q$R$_{27}$, —NR$_{26}$C(O)R$_{27}$, halogen, —P(O)((C$_1$-C$_6$) alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more R$_{16}$;

each R$_{15}$ is independently $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

each R$_{16}$ is independently $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —OH, or CN, wherein in the alkyl, aryl, heteroaryl, cycloalkyl, and heterocycloalkyl are optionally substituted with one or more R$_{28}$;

each R$_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more R$_{18}$;

each R$_{18}$ is independently $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

each R$_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)((C$_1$-C$_6$) alkyl)$_2$, —P(O)(aryl)$_2$, —SiMe$_3$, —SF$_5$, —OH, or CN;

each R$_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —NH$_2$, or CN;

each R$_{21}$ and R$_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more R$_{25}$;

each R$_{23}$ and R$_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more R$_{25}$;

each R$_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, or CN;

each R$_{26}$ and R$_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, —NH$_2$, $(C_1-C_6)$ alkylamino, or di$(C_1-C_6)$ alkylamino;

each R$_{28}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

m is 0, 1, 2, 3, or 4;

n is 0, 1, 2, or 3;

q is independently at each occurrence 0, 1, or 2; and provided that when R$_2$ is optionally substituted alkyl, R$_5$ is H, and R$_7$ is H, R$_6$ is not chloro.

Another aspect of the present disclosure relates to a method of treating a disease or disorder associated with modulation of USP7. The method comprises administering to a patient in need of a treatment for diseases or disorders associated with modulation of USP7 an effective amount of a compound of Formula (I), or a pharmaceutically acceptable salt, hydrate, solvate, prodrug, stereoisomer, or tautomer thereof.

Another aspect of the present disclosure is directed to a method of inhibiting USP7. The method involves administering to a patient in need thereof an effective amount of a compound of Formula (I), or a pharmaceutically acceptable salt, hydrate, solvate, prodrug, stereoisomer, or tautomer thereof.

Another aspect of the present disclosure relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the present disclosure relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the present disclosure relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the present disclosure relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the present disclosure relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the present disclosure is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease associated with inhibiting USP7.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP7.

The present disclosure further provides methods of treating a disease or disorder associated with modulation of USP7 including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present disclosure provides inhibitors of USP7 that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present disclosure further provides compounds and compositions with an improved efficacy and safety profile relative to known USP7 inhibitors. The present disclosure also provides agents with novel mechanisms of action toward USP7 enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present disclosure provides the medical community with a novel pharmacological strategy for the treatment of diseases and disorders associated with USP7 enzymes.

DETAILED DESCRIPTION OF THE DISCLOSURE

The present disclosure relates to compounds and compositions that are capable of inhibiting the activity USP7. The disclosure features methods of treating, preventing or ameliorating a disease or disorder in which USP7 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of USP7 dependent diseases and disorders by inhibiting the activity of USP7 enzymes. Inhibition of USP7 provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the disclosure, the compounds of Formula (I) are described:

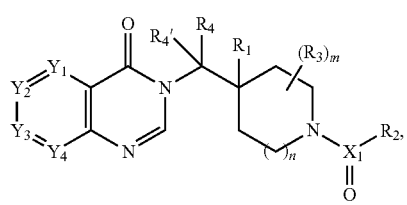

(I)

and pharmaceutically acceptable salts, hydrates, solvates, prodrugs, stereoisomers, and tautomers thereof, wherein $R_1$, $R_2$, $R_3$, $R_4$, $R_4'$, $X_1$, $Y_1$, $Y_2$, $Y_3$, $Y_4$, m, and n are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" or "carbocyclyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more —OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

The term "amino" as used herein means a substituent containing at least one nitrogen atom (e.g., $NH_2$).

The term "alkylamino" as used herein refers to an amino or $NH_2$ group where one of the hydrogens has been replaced with an alkyl group, as defined herein above, e.g., —NH(alkyl). Examples of alkylamino groups include, but are not limited to, methylamino (e.g., —NH(CH$_3$)), ethylamino, propylamino, iso-propylamino, n-butylamino, sec-butylamino, tert-butylamino, etc.

The term "dialkylamino" as used herein refers to an amino or $NH_2$ group where both of the hydrogens have been replaced with alkyl groups, as defined herein above, e.g., —N(alkyl)$_2$. The alkyl groups on the amino group can be the same or different alkyl groups. Example of dialkylamino groups include, but are not limited to, dimethylamino (e.g., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A (C$_3$-C$_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present disclosure relates to compounds or pharmaceutically acceptable salts, hydrates, solvates, prodrugs, stereoisomers, or tautomers thereof, capable of inhibiting USP7, which are useful for the treatment of diseases and disorders associated with modulation of a USP7 enzyme. The disclosure further relates to compounds, or pharmaceutically acceptable salts, hydrates, solvates, prodrugs, stereoisomers, or tautomers thereof, which are useful for inhibiting USP7.

In one embodiment, the compounds of Formula (I) have the structure of Formula (Ia):

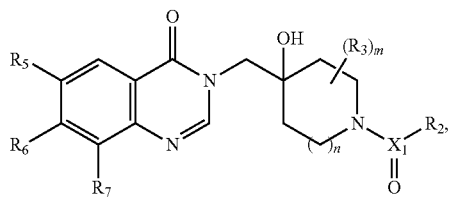

(Ia)

and pharmaceutically acceptable salts, hydrates, solvates, prodrugs, stereoisomers, and tautomers thereof,
wherein:

$X_1$ is C, S, or S(O);

$R_2$ is $(C_1-C_6)$ alkyl, $(C_6-C_{14})$ aryl, heteroaryl, $(C_5-C_8)$ cycloalkyl, heterocycloalkyl, $-NR_{10}R_{11}$, or $-OR_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_5$ is H, $(C_1-C_6)$ alkyl, $(C_2-C_6)$ alkenyl, $(C_2-C_6)$ alkynyl, $(C_1-C_6)$ haloalkyl, halogen, $NO_2$, or CN, wherein the alkyl, alkenyl, and alkynyl are optionally substituted with one or more $R_{12}$;

$R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, $NO_2$, $-NH_2$, $-NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1-C_6)$ alkyl, $(C_6-C_{14})$ aryl, heteroaryl, $(C_5-C_8)$ cycloalkyl, heterocycloalkyl, $-$O-aryl, $-$O-heteroaryl, $-N((C_1-C_6)$ alkyl)-aryl, NH-aryl $-N((C_1-C_6)$ alkyl)-heteroaryl, or $-$NH-heteroaryl, wherein the alkyl, aryl, heteroaryl, cycloalkyl, and heterocycloalkyl are optionally substituted with one or more $R_{14}$;

wherein $R_5$, $R_6$, and $R_7$ are not all simultaneously H;

each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, $-(C_1-C_3)$-alkylene-O$-(C_1-C_6)$ alkyl, $-(C_0-C_4)$-alkylene-aryl, $-(C_0-C_4)$-alkylene-heteroaryl, $(C_3-C_{10})$ cycloalkyl, heterocycloalkyl, $-(C_0-C_4)$-alkylene-O-aryl, $-(C_0-C_4)$-alkylene-O-heteroaryl, $-$O$-(C_3-C_8)$cycloalkyl, $-$S-heteroaryl, $-C(O)R_{21}$, $-CO(O)R_{21}$, $-C(O)NR_{21}R_{22}$, $-S(O)_qR_{21}$, $-S(O)_qNR_{21}R_{22}$, $-NR_{21}S(O)_qR_{22}$, $-(C_0-C_3)$-alkylene-$NR_{21}R_{22}$, $-NR_{21}C(O)R_{22}$, $-NR_{21}C(O)C(O)R_{22}$, $-NR_{21}C(O)NR_{21}R_{22}$, $-P(O)((C_1-C_6)$ alkyl)$_2$, $-P(O)(aryl)_2$, $-SiMe_3$, $-SF_5$, or $-OR_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, $-(C_0-C_3)$-alkylene-$(C_6-C_{14})$ aryl, $-(C_0-C_3)$-alkylene-heteroaryl, $-NH_2$, $-OH$, $-C(O)R_{23}$, $-C(O)NR_{23}R_{24}$, $-NR_{23}C(O)R_{24}$, $-NR_{23}R_{24}$, $-S(O)_qR_{23}$, $-S(O)_qNR_{23}R_{24}$, $-NR_{23}S(O)_qR_{24}$, Oxo, $-P(O)((C_1-C_6)$ alkyl)$_2$, $-P(O)(aryl)_2$, $-SiMe_3$, $-SF_5$, $-$O-aryl, CN, or $-$O-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{12}$ is independently $(C_1-C_6)$ alkyl, $(C_1-C_6)$ alkoxy, $(C_1-C_6)$ haloalkyl, $(C_1-C_6)$ haloalkoxy, halogen, CN, $-C(O)(C_1-C_6)$ alkyl, $-S(O)_q(C_1-C_6)$ alkyl, $-NH_2$, $(C_1-C_6)$ alkylamino, or di$(C_1-C_6)$ alkylamino;

each $R_{13}$ is independently D, $(C_1-C_6)$ alkyl, $(C_1-C_6)$ alkoxy, $(C_1-C_6)$ haloalkyl, $(C_1-C_6)$ haloalkoxy, halogen, CN, $-OH$, $-NH_2$, $-C(O)(C_1-C_6)$ alkyl, $-S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, $-$O-aryl, $-$O-heteroaryl, $-$O-heterocycloalkyl, $-$O$-(C_3-C_8)$cycloalkyl, $-C(O)O(C_1-C_6)$ alkyl, $-C(O)NR_{26}R_{27}$, $-S(O)_qNR_{26}R_{27}$, $-NR_{26}R_{27}$, $-NR_{26}C(O)NR_{26}R_{27}$, $-NR_{26}C(O)OR_{27}$, $-NR_{26}S(O)_qR_{27}$, $-NR_{26}C(O)R_{27}$, halogen, $-P(O)((C_1-C_6)$ alkyl)$_2$, $-P(O)(aryl)_2$, $-SiMe_3$, or $-SF_5$, wherein in the alkyl, aryl, heteroaryl, cycloalkyl, and heterocycloalkyl are optionally substituted with one or more $R_{15}$;

each $R_{14}$ is independently D, $(C_1-C_6)$ alkyl, $(C_1-C_6)$ alkoxy, $(C_1-C_6)$ haloalkyl, $(C_1-C_6)$ haloalkoxy, halogen, CN, $-OH$, $-NH_2$, $-C(O)(C_1-C_6)$ alkyl, $-S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, $-$O-aryl, $-$O-heteroaryl, $-$O-heterocycloalkyl, $-$O$-(C_3-C_8)$cycloalkyl, $-C(O)O(C_1-C_6)$ alkyl, $-C(O)NR_{26}R_{27}$, $-S(O)_qNR_{26}R_{27}$, $-NR_{26}R_{27}$, $-NR_{26}C(O)NR_{26}R_{27}$, $-NR_{26}C(O)OR_{27}$, $-NR_{26}S(O)_qR_{27}$, $-NR_{26}C(O)R_{27}$, halogen, $-P(O)((C_1-C_6)$ alkyl)$_2$, $-P(O)(aryl)_2$, $-SiMe_3$, or $-SF_5$, wherein in the alkyl, aryl, heteroaryl, cycloalkyl, and heterocycloalkyl are optionally substituted with one or more $R_{16}$;

each $R_{15}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $-OH$, or CN;

each $R_{16}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, $-$O-aryl, $-$O-heteroaryl, $-$O-heterocycloalkyl, $-$O$-(C_3-C_8)$cycloalkyl, —OH, or CN, wherein in the alkyl, aryl, heteroaryl, cycloalkyl, and heterocycloalkyl are optionally substituted with one or more $R_{28}$;

each $R_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1-C_6)$ alkyl, $(C_1-C_6)$ alkoxy, $(C_1-C_6)$ haloalkyl, $(C_1-C_6)$ haloalkoxy, halogen, —C(O) $(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)(($C_1-C_6$) alkyl)$_2$, —P(O)(aryl)$_2$, —SiMe$_3$, —SF$_5$, —OH, or CN;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —NH$_2$, or CN;

each $R_{21}$ and $R_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, or CN;

each $R_{26}$ and $R_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, —NH$_2$, $(C_1-C_6)$ alkylamino, or di$(C_1-C_6)$ alkylamino;

each $R_{28}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

m is 0, 1, 2, 3, or 4;

n is 0, 1, 2, or 3;

q is independently at each occurrence 0, 1, or 2; and provided that when $R_2$ is optionally substituted alkyl, $R_5$ is H, and $R_7$ is H, $R_6$ is not chloro.

In another embodiment, the compounds of Formula (I) have the structure of Formula (Ib):

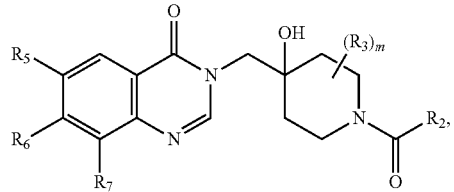

(Ib)

and pharmaceutically acceptable salts, hydrates, solvates, prodrugs, stereoisomers, and tautomers thereof, wherein:

$R_2$ is $(C_1-C_6)$ alkyl, $(C_6-C_{14})$ aryl, heteroaryl, $(C_5-C_8)$ cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_5$ is H, $(C_1-C_6)$ alkyl, $(C_2-C_6)$ alkenyl, $(C_2-C_6)$ alkynyl, $(C_1-C_6)$ haloalkyl, halogen, NO$_2$, or CN, wherein the alkyl, alkenyl, and alkynyl are optionally substituted with one or more $R_{12}$;

$R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, NO$_2$, —NH$_2$, —NHC(O)$(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1-C_6)$ alkyl, $(C_6-C_{14})$ aryl, heteroaryl, $(C_5-C_8)$ cycloalkyl, heterocycloalkyl, —O-aryl, —O-heteroaryl, —N(($C_1-C_6$) alkyl)-aryl, NH-aryl, —N(($C_1-C_6$) alkyl)-heteroaryl, or —NH-heteroaryl, wherein the alkyl, aryl, heteroaryl, cycloalkyl, and heterocycloalkyl are optionally substituted with one or more $R_{14}$;

wherein $R_5$, $R_6$, and $R_7$ are not all simultaneously H;

each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, —($C_1-C_3$)-alkylene-O—($C_1-C_6$) alkyl, —($C_0-C_4$)-alkylene-aryl, —($C_0-C_4$)-alkylene-heteroaryl, $(C_3-C_{10})$ cycloalkyl, heterocycloalkyl, —($C_0-C_4$)-alkylene-O-aryl, —($C_0-C_4$)-alkylene-O-heteroaryl, —O—($C_3-C_8$)cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O) R$_{22}$, —NR$_{21}$C(O)NR$_{21}$R$_{22}$, —P(O)(($C_1-C_6$) alkyl)$_2$, —P(O) (aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, —($C_0-C_3$)-alkylene-($C_6-C_{14}$) aryl, —($C_0-C_3$)-alkylene-heteroaryl, —NH$_2$, —OH, —C(O) R$_{23}$, —C(O)NR$_{23}$R$_{24}$, —NR$_{23}$C(O)R$_{24}$, —NR$_{23}$R$_{24}$, —S(O)$_q$R$_{23}$, —S(O)$_q$NR$_{23}$R$_{24}$, —NR$_{23}$S(O)$_q$R$_{24}$, Oxo, —P(O)((C$_1$-C$_6$) alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more R$_{19}$;

R$_{10}$ and R$_{11}$ are independently H, (C$_1$-C$_6$) alkyl, (C$_6$-C$_{14}$) aryl, heteroaryl, (C$_5$-C$_8$) cycloalkyl, or heterocycloalkyl, wherein the alkyl, aryl, heteroaryl, cycloalkyl, and heterocycloalkyl are optionally substituted with one or more R$_{17}$; or R$_{10}$ and R$_{11}$ together with the nitrogen to which they are attached form a heterocycloalkyl ring optionally substituted with one or more R$_{17}$;

each R$_{12}$ is independently (C$_1$-C$_6$) alkyl, (C$_1$-C$_6$) alkoxy, (C$_1$-C$_6$) haloalkyl, (C$_1$-C$_6$) haloalkoxy, halogen, CN, —C(O)(C$_1$-C$_6$) alkyl, —S(O)$_q$(C$_1$-C$_6$) alkyl, —NH$_2$, (C$_1$-C$_6$) alkylamino, or di(C$_1$-C$_6$) alkylamino;

each R$_{13}$ is independently D, (C$_1$-C$_6$) alkyl, (C$_1$-C$_6$) alkoxy, (C$_1$-C$_6$) haloalkyl, (C$_1$-C$_6$) haloalkoxy, halogen, CN, —OH, —NH$_2$, —C(O)(C$_1$-C$_6$) alkyl, —S(O)$_q$(C$_1$-C$_6$) alkyl, (C$_1$-C$_6$) alkylamino, di(C$_1$-C$_6$) alkylamino, (C$_6$-C$_{14}$) aryl, heteroaryl, (C$_3$-C$_8$) cycloalkyl, heterocycloalkyl, —O-aryl, —O-heteroaryl, —O-heterocycloalkyl, —O—(C$_3$-C$_8$)cycloalkyl, —C(O)O(C$_1$-C$_6$) alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O)OR$_{27}$, —NR$_{26}$S(O)$_q$R$_{27}$, —NR$_{26}$C(O)R$_{27}$, halogen, —P(O)((C$_1$-C$_6$) alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more R$_{15}$;

each R$_{14}$ is independently D, (C$_1$-C$_6$) alkyl, (C$_1$-C$_6$) alkoxy, (C$_1$-C$_6$) haloalkyl, (C$_1$-C$_6$) haloalkoxy, halogen, CN, —OH, —NH$_2$, —C(O)(C$_1$-C$_6$) alkyl, —S(O)$_q$(C$_1$-C$_6$) alkyl, (C$_1$-C$_6$) alkylamino, di(C$_1$-C$_6$) alkylamino, (C$_6$-C$_{14}$) aryl, heteroaryl, (C$_3$-C$_8$) cycloalkyl, heterocycloalkyl, —O-aryl, —O-heteroaryl, —O-heterocycloalkyl, —O—(C$_3$-C$_8$)cycloalkyl, —C(O)O(C$_1$-C$_6$) alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O)OR$_{27}$, —NR$_{26}$S(O)$_q$R$_{27}$, —NR$_{26}$C(O)R$_{27}$, halogen, —P(O)((C$_1$-C$_6$) alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more R$_{16}$;

each R$_{15}$ is independently (C$_1$-C$_6$) alkyl, (C$_1$-C$_6$) alkoxy, (C$_1$-C$_6$) haloalkyl, (C$_1$-C$_6$) haloalkoxy, halogen, —C(O)(C$_1$-C$_6$) alkyl, —S(O)$_q$(C$_1$-C$_6$) alkyl, —NH$_2$, (C$_1$-C$_6$) alkylamino, di(C$_1$-C$_6$) alkylamino, —OH, or CN;

each R$_{16}$ is independently (C$_1$-C$_6$) alkyl, (C$_1$-C$_6$) alkoxy, (C$_1$-C$_6$) haloalkyl, (C$_1$-C$_6$) haloalkoxy, halogen, —C(O)(C$_1$-C$_6$) alkyl, —S(O)$_q$(C$_1$-C$_6$) alkyl, —NH$_2$, (C$_1$-C$_6$) alkylamino, di(C$_1$-C$_6$) alkylamino, (C$_6$-C$_{14}$) aryl, heteroaryl, (C$_3$-C$_8$) cycloalkyl, heterocycloalkyl, —O-aryl, —O-heteroaryl, —O-heterocycloalkyl, —O—(C$_3$-C$_8$)cycloalkyl, —OH, or CN, wherein in the alkyl, aryl, heteroaryl, cycloalkyl, and heterocycloalkyl are optionally substituted with one or more R$_{28}$;

each R$_{17}$ is independently (C$_1$-C$_6$) alkyl, (C$_1$-C$_6$) alkoxy, (C$_1$-C$_6$) haloalkyl, (C$_1$-C$_6$) haloalkoxy, halogen, (C$_1$-C$_6$) hydroxyalkyl, —OH, CN, —C(O)(C$_1$-C$_6$) alkyl, —S(O)$_q$ (C$_1$-C$_6$) alkyl, —NH$_2$, (C$_1$-C$_6$) alkylamino, di(C$_1$-C$_6$) alkylamino, (C$_6$-C$_{14}$) aryl, heteroaryl, (C$_5$-C$_8$) cycloalkyl, or heterocycloalkyl, wherein in the alkyl, aryl, heteroaryl, cycloalkyl, and heterocycloalkyl are optionally substituted with one or more R$_{18}$;

each R$_{18}$ is independently (C$_1$-C$_6$) alkyl, (C$_1$-C$_6$) alkoxy, (C$_1$-C$_6$) haloalkyl, (C$_1$-C$_6$) haloalkoxy, halogen, —C(O) (C$_1$-C$_6$) alkyl, —S(O)$_q$(C$_1$-C$_6$) alkyl, —NH$_2$, (C$_1$-C$_6$) alkylamino, di(C$_1$-C$_6$) alkylamino, —OH, or CN;

each R$_{19}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)((C$_1$-C$_6$) alkyl)$_2$, —P(O)(aryl)$_2$, —SiMe$_3$, —SF$_5$, —OH, or CN;

each R$_{20}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —OH, —NH$_2$, or CN;

each R$_{21}$ and R$_{22}$ is independently H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, aryl, heteroaryl, cycloalkyl and heterocycloalkyl are optionally substituted with one or more R$_{25}$;

each R$_{23}$ and R$_{24}$ is independently H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, aryl, heteroaryl, cycloalkyl and heterocycloalkyl are optionally substituted with one or more R$_{25}$;

each R$_{25}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —OH, or CN;

each R$_{26}$ and R$_{27}$ is independently at each occurrence H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, alkenyl, alkynyl, aryl, heteroaryl, cycloalkyl and heterocycloalkyl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, —NH$_2$, (C$_1$-C$_6$) alkylamino, or di(C$_1$-C$_6$) alkylamino;

each R$_{28}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —C(O)(C$_1$-C$_6$) alkyl, —S(O)$_q$(C$_1$-C$_6$) alkyl, —NH$_2$, (C$_1$-C$_6$) alkylamino, di(C$_1$-C$_6$) alkylamino, —OH, or CN;

m is 0, 1, 2, 3, or 4;

q is independently at each occurrence 0, 1, or 2; and provided that when R$_2$ is optionally substituted alkyl, R$_5$ is H, and R$_7$ is H, R$_6$ is not chloro.

In another embodiment, the compounds of Formula (I) have the structure of Formula (Ic):

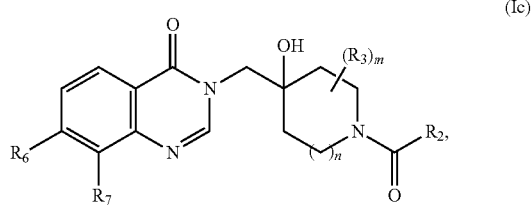

and pharmaceutically acceptable salts, hydrates, solvates, prodrugs, stereoisomers, and tautomers thereof, wherein:

R$_2$ is (C$_1$-C$_6$) alkyl, (C$_6$-C$_{14}$) aryl, heteroaryl, (C$_5$-C$_8$) cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more R$_8$;

each R$_3$ is independently at each occurrence selected from D, (C$_1$-C$_6$) alkyl, (C$_6$-C$_{14}$) aryl, heteroaryl, (C$_3$-C$_8$) cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3$-$C_8)$ cycloalkyl optionally substituted with one or more $R_{20}$; or two $R_3$ together when attached to the same carbon atom form a $(C_3$-$C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_6$ is H, D, $(C_1$-$C_6)$ alkyl, $(C_2$-$C_6)$ alkenyl, $(C_2$-$C_6)$ alkynyl, $(C_1$-$C_6)$ alkoxy, $(C_1$-$C_6)$ haloalkyl, $(C_1$-$C_6)$ haloalkoxy, halogen, CN, $NO_2$, $-NH_2$, $-NHC(O)(C_1$-$C_6)$ alkyl, $(C_6$-$C_{14})$ aryl, heteroaryl, $(C_5$-$C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1$-$C_6)$ alkyl, $(C_6$-$C_{14})$ aryl, heteroaryl, $(C_5$-$C_8)$ cycloalkyl, heterocycloalkyl, —O-aryl, —O-heteroaryl, —N$((C_1$-$C_6)$ alkyl)-aryl, NH-aryl, —N$((C_1$-$C_6)$ alkyl)-heteroaryl, or —NH-heteroaryl, wherein the alkyl, aryl, heteroaryl, cycloalkyl, and heterocycloalkyl are optionally substituted with one or more $R_{14}$;

wherein $R_6$ and $R_7$ are not both simultaneously H;

each $R_8$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —$(C_1$-$C_3)$-alkylene-O—$(C_1$-$C_6)$ alkyl, —$(C_0$-$C_4)$-alkylene-aryl, —$(C_0$-$C_4)$-alkylene-heteroaryl, $(C_3$-$C_{10})$ cycloalkyl, heterocycloalkyl, —$(C_0$-$C_4)$-alkylene-O-aryl, —$(C_0$-$C_4)$-alkylene-O-heteroaryl, —O—$(C_3$-$C_8)$cycloalkyl, —S-heteroaryl, —C(O)$R_{21}$, —CO(O)$R_{21}$, —C(O)N$R_{21}R_{22}$, —S(O)$_q R_{21}$, —S(O)$_q$N$R_{21}R_{22}$, —N$R_{21}$S(O)$_q R_{22}$, —$(C_0$-$C_3)$-alkylene-N$R_{21}R_{22}$, —N$R_{21}$C(O)$R_{22}$, —N$R_{21}$C(O)C(O)$R_{22}$, —N$R_{21}$C(O)N$R_{21}R_{22}$, —P(O)$((C_1$-$C_6)$ alkyl)$_2$, —P(O)(aryl)$_2$, —SiMe$_3$, —SF$_5$, or —O$R_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3$-$C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, $(C_3$-$C_8)$ cycloalkyl, heterocycloalkyl, —$(C_0$-$C_3)$-alkylene-$(C_6$-$C_{14})$ aryl, —$(C_0$-$C_3)$-alkylene-heteroaryl, —$NH_2$, —OH, —C(O)$R_{23}$, —C(O)N$R_{23}R_{24}$, —N$R_{23}$C(O)$R_{24}$, —N$R_{23}R_{24}$, —S(O)$_q R_{23}$, —S(O)$_q$N$R_{23}R_{24}$, —N$R_{23}$S(O)$_q R_{24}$, oxo, —P(O)$((C_1$-$C_6)$ alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1$-$C_6)$ alkyl, $(C_6$-$C_{14})$ aryl, heteroaryl, $(C_5$-$C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{13}$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —$NH_2$, —C(O)$(C_1$-$C_6)$ alkyl, —S(O)$_q$$(C_1$-$C_6)$ alkyl, $(C_1$-$C_6)$ alkylamino, di$(C_1$-$C_6)$ alkylamino, $(C_6$-$C_{14})$ aryl, heteroaryl, $(C_3$-$C_8)$ cycloalkyl, heterocycloalkyl, —O-aryl, —O-heteroaryl, —O-heterocycloalkyl, —O—$(C_3$-$C_8)$cycloalkyl, —C(O)O$(C_1$-$C_6)$ alkyl, —C(O)N$R_{26}R_{27}$, —S(O)$_q$N$R_{26}R_{27}$, —N$R_{26}R_{27}$, —N$R_{26}$C(O)N$R_{26}R_{27}$, —N$R_{26}$C(O)O$R_{27}$, —N$R_{26}$S(O)$_q R_{27}$, —N$R_{26}$C(O)$R_{27}$, halogen, —P(O)$((C_1$-$C_6)$ alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more $R_{15}$;

each $R_{14}$ is independently D, $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —$NH_2$, —C(O)$(C_1$-$C_6)$ alkyl, —S(O)$_q$$(C_1$-$C_6)$ alkyl, $(C_1$-$C_6)$ alkylamino, di$(C_1$-$C_6)$ alkylamino, $(C_6$-$C_{14})$ aryl, heteroaryl, $(C_3$-$C_8)$ cycloalkyl, heterocycloalkyl, —O-aryl, —O-heteroaryl, —O-heterocycloalkyl, —O—$(C_3$-$C_8)$cycloalkyl, —C(O)O$(C_1$-$C_6)$ alkyl, —C(O)N$R_{26}R_{27}$, —S(O)$_q$N$R_{26}R_{27}$, —N$R_{26}R_{27}$, —N$R_{26}$C(O)N$R_{26}R_{27}$, —N$R_{26}$C(O)O$R_{27}$, —N$R_{26}$S(O)$_q R_{27}$, —N$R_{26}$C(O)$R_{27}$, halogen, —P(O)$((C_1$-$C_6)$ alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more $R_{16}$;

each $R_{15}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, —C(O)$(C_1$-$C_6)$ alkyl, —S(O)$_q$$(C_1$-$C_6)$ alkyl, —$NH_2$, $(C_1$-$C_6)$ alkylamino, di$(C_1$-$C_6)$ alkylamino, —OH, or CN;

each $R_{16}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, —C(O)$(C_1$-$C_6)$ alkyl, —S(O)$_q$$(C_1$-$C_6)$ alkyl, —$NH_2$, $(C_1$-$C_6)$ alkylamino, di$(C_1$-$C_6)$ alkylamino, $(C_6$-$C_{14})$ aryl, heteroaryl, $(C_3$-$C_8)$ cycloalkyl, heterocycloalkyl, —O-aryl, —O-heteroaryl, —O-heterocycloalkyl, —O—$(C_3$-$C_8)$cycloalkyl, —OH, or CN, wherein in the alkyl, aryl, heteroaryl, cycloalkyl, and heterocycloalkyl are optionally substituted with one or more $R_{28}$;

each $R_{17}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, $(C_1$-$C_6)$ hydroxyalkyl, —OH, CN, —C(O)$(C_1$-$C_6)$ alkyl, —S(O)$_q$$(C_1$-$C_6)$ alkyl, —$NH_2$, $(C_1$-$C_6)$ alkylamino, di$(C_1$-$C_6)$ alkylamino, $(C_6$-$C_{14})$ aryl, heteroaryl, $(C_5$-$C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, —C(O)$(C_1$-$C_6)$ alkyl, —S(O)$_q$$(C_1$-$C_6)$ alkyl, —$NH_2$, $(C_1$-$C_6)$ alkylamino, di$(C_1$-$C_6)$ alkylamino, —OH, or CN;

each $R_{19}$ is independently at each occurrence $(C_1$-$C_6)$ alkyl, $(C_1$-$C_6)$ alkoxy, $(C_1$-$C_6)$ haloalkyl, $(C_1$-$C_6)$ haloalkoxy, halogen, —N$R_{26}$C(O)$R_{27}$, —N$R_{26}$S(O)$_q R_{27}$, —C(O)$R_{26}$, —C(O)N$R_{26}R_{27}$, —N$R_{26}R_{27}$, —S(O)$_q R_{26}$, —S(O)$_q$N$R_{26}R_{27}$, —P(O)$((C_1$-$C_6)$ alkyl)$_2$, —P(O)(aryl)$_2$, —SiMe$_3$, —SF$_5$, —OH, or CN;

each $R_{20}$ is independently at each occurrence $(C_1$-$C_6)$ alkyl, $(C_1$-$C_6)$ alkoxy, $(C_1$-$C_6)$ haloalkyl, $(C_1$-$C_6)$ haloalkoxy, halogen, —OH, —$NH_2$, or CN;

each $R_{21}$ and $R_{22}$ is independently H, $(C_1$-$C_6)$ alkyl, $(C_2$-$C_6)$ alkenyl, $(C_2$-$C_6)$ alkynyl, $(C_6$-$C_{14})$ aryl, heteroaryl, $(C_5$-$C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1$-$C_6)$ alkyl, $(C_2$-$C_6)$ alkenyl, $(C_2$-$C_6)$ alkynyl, $(C_6$-$C_{14})$ aryl, heteroaryl, ($C_5$-$C_8$) cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, —OH, or CN;

each $R_{26}$ and $R_{27}$ is independently at each occurrence H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, alkenyl, alkynyl, aryl, heteroaryl, cycloalkyl and heterocycloalkyl are optionally substituted with one or more substituents independently selected from ($C_1$-$C_6$) alkyl, ($C_1$-$C_6$) alkoxy, ($C_1$-$C_6$) haloalkyl, ($C_1$-$C_6$) haloalkoxy, —NH$_2$, ($C_1$-$C_6$) alkylamino, or di($C_1$-$C_6$) alkylamino;

each $R_{28}$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, —C(O)($C_1$-$C_6$) alkyl, —S(O)$_q$($C_1$-$C_6$) alkyl, —NH$_2$, ($C_1$-$C_6$) alkylamino, di($C_1$-$C_6$) alkylamino, —OH, or CN;

m is 0, 1, 2, 3, or 4;

n is 0, 1, 2, or 3;

q is independently at each occurrence 0, 1, or 2; and provided that when $R_2$ is optionally substituted alkyl and $R_7$ is H, $R_6$ is not chloro.

In another embodiment, the compounds of Formula (I) have the structure of Formula (Id):

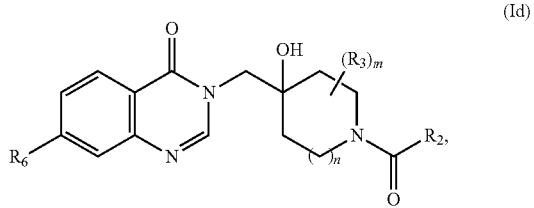

(Id)

and pharmaceutically acceptable salts, hydrates, solvates, prodrugs, stereoisomers, and tautomers thereof, wherein:

$R_2$ is ($C_1$-$C_6$) alkyl, ($C_6$-$C_{14}$) aryl, heteroaryl, ($C_5$-$C_8$) cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more $R_8$;

each $R_3$ is independently at each occurrence selected from D, ($C_1$-$C_6$) alkyl, ($C_6$-$C_{14}$) aryl, heteroaryl, ($C_3$-$C_8$) cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a ($C_3$-$C_8$) cycloalkyl optionally substituted with one or more $R_{20}$; or two $R_3$ together when attached to the same carbon atom form a ($C_3$-$C_8$) spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_6$ is D, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, halogen, CN, NO$_2$, —NH$_2$, —NHC(O)($C_1$-$C_6$) alkyl, ($C_6$-$C_{14}$) aryl, heteroaryl, ($C_5$-$C_8$) cycloalkyl, or heterocycloalkyl, wherein the alkyl, aryl, heteroaryl, cycloalkyl, and heterocycloalkyl are optionally substituted with one or more $R_{13}$;

each $R_8$ is independently D, ($C_1$-$C_6$) alkyl, ($C_1$-$C_6$) alkoxy, ($C_1$-$C_6$) haloalkyl, ($C_1$-$C_6$) haloalkoxy, halogen, CN, —($C_1$-$C_3$)-alkylene-O—($C_1$-$C_6$) alkyl, —($C_0$-$C_4$)-alkylene-aryl, —($C_0$-$C_4$)-alkylene-heteroaryl, ($C_3$-$C_{10}$) cycloalkyl, heterocycloalkyl, —($C_0$-$C_4$)-alkylene-O-aryl, —($C_0$-$C_4$)-alkylene-O-heteroaryl, —O—($C_3$-$C_8$)cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O)R$_{22}$, —NR$_{21}$C(O)NR$_{21}$R$_{22}$, —P(O)(($C_1$-$C_6$) alkyl)$_2$, —P(O)(aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more $R_9$; or two $R_8$ together when on adjacent atoms form a ($C_3$-$C_8$) cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently ($C_1$-$C_6$) alkyl, ($C_1$-$C_6$) alkoxy, ($C_1$-$C_6$) haloalkyl, ($C_1$-$C_6$) haloalkoxy, halogen, ($C_3$-$C_8$) cycloalkyl, heterocycloalkyl, —(C$_0$-C$_3$)-alkylene-($C_6$-$C_{14}$) aryl, —(C$_0$-C$_3$)-alkylene-heteroaryl, —NH$_2$, —OH, —C(O)R$_{23}$, —C(O)NR$_{23}$R$_{24}$, —NR$_{23}$C(O)R$_{24}$, —NR$_{23}$R$_{24}$, —S(O)$_q$R$_{23}$, —S(O)$_q$NR$_{23}$R$_{24}$, —NR$_{23}$S(O)$_q$R$_{24}$, oxo, —P(O)(($C_1$-$C_6$) alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more $R_{19}$;

$R_{10}$ and $R_{11}$ are independently H, ($C_1$-$C_6$) alkyl, ($C_6$-$C_{14}$) aryl, heteroaryl, ($C_5$-$C_8$) cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{13}$ is independently D, ($C_1$-$C_6$) alkyl, ($C_1$-$C_6$) alkoxy, ($C_1$-$C_6$) haloalkyl, ($C_1$-$C_6$) haloalkoxy, halogen, CN, —OH, —NH$_2$, —C(O)($C_1$-$C_6$) alkyl, —S(O)$_q$($C_1$-$C_6$) alkyl, ($C_1$-$C_6$) alkylamino, di($C_1$-$C_6$) alkylamino, ($C_6$-$C_{14}$) aryl, heteroaryl, ($C_3$-$C_8$) cycloalkyl, heterocycloalkyl, —O-aryl, —O-heteroaryl, —O-heterocycloalkyl, —O—($C_3$-$C_8$)cycloalkyl, —C(O)O($C_1$-$C_6$) alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O) OR$_{27}$, —NR$_{26}$S(O)$_q$R$_{27}$, —NR$_{26}$C(O)R$_{27}$, halogen, —P(O)(($C_1$-$C_6$) alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more $R_{15}$;

each $R_{15}$ is independently ($C_1$-$C_6$) alkyl, ($C_1$-$C_6$) alkoxy, ($C_1$-$C_6$) haloalkyl, ($C_1$-$C_6$) haloalkoxy, halogen, —C(O) ($C_1$-$C_6$) alkyl, —S(O)$_q$($C_1$-$C_6$) alkyl, —NH$_2$, ($C_1$-$C_6$) alkylamino, di($C_1$-$C_6$) alkylamino, —OH, or CN;

each $R_{17}$ is independently ($C_1$-$C_6$) alkyl, ($C_1$-$C_6$) alkoxy, ($C_1$-$C_6$) haloalkyl, ($C_1$-$C_6$) haloalkoxy, halogen, ($C_1$-$C_6$) hydroxyalkyl, —OH, CN, —C(O)($C_1$-$C_6$) alkyl, —S(O)$_q$ ($C_1$-$C_6$) alkyl, —NH$_2$, ($C_1$-$C_6$) alkylamino, di($C_1$-$C_6$) alkylamino, ($C_6$-$C_{14}$) aryl, heteroaryl, ($C_5$-$C_8$) cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)((C$_1$-C$_6$) alkyl)$_2$, —P(O)(aryl)$_2$, —SiMe$_3$, —SF$_5$, —OH, or CN;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —NH$_2$, or CN;

each $R_{21}$ and $R_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, or CN;

each $R_{26}$ and $R_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, —NH$_2$, $(C_1-C_6)$ alkylamino, or di$(C_1-C_6)$ alkylamino;

m is 0, 1, 2, 3, or 4;
n is 0, 1, 2, or 3;
q is independently at each occurrence 0, 1, or 2; and
provided that when $R_2$ is optionally substituted alkyl, $R_6$ is not chloro.

In another embodiment, the compounds of Formula (I) have the structure of Formula (Ie):

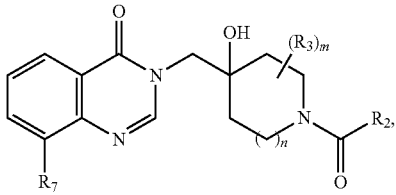

(Ie)

and pharmaceutically acceptable salts, hydrates, solvates, prodrugs, stereoisomers, and tautomers thereof,
wherein:

$R_2$ is $(C_1-C_6)$ alkyl, $(C_6-C_{14})$ aryl, heteroaryl, $(C_5-C_8)$ cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_7$ is $(C_1-C_6)$ alkyl, $(C_6-C_{14})$ aryl, heteroaryl, $(C_5-C_8)$ cycloalkyl, heterocycloalkyl, —O-aryl, —O-heteroaryl, —N((C$_1$-C$_6$) alkyl)-aryl, NH-aryl, —N((C$_1$-C$_6$) alkyl)-heteroaryl, or —NH— heteroaryl, wherein the alkyl, aryl, heteroaryl, cycloalkyl, and heterocycloalkyl are optionally substituted with one or more $R_{14}$;

each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, —(C$_1$-C$_3$)-alkylene-O—(C$_1$-C$_6$) alkyl, —(C$_0$-C$_4$)-alkylene-aryl, —(C$_0$-C$_4$)-alkylene-heteroaryl, $(C_3-C_{10})$ cycloalkyl, heterocycloalkyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O)R$_{22}$, —NR$_{21}$C(O)NR$_{21}$R$_{22}$, —P(O)((C$_1$-C$_6$) alkyl)$_2$, —P(O)(aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, —(C$_0$-C$_3$)-alkylene-(C$_6$-C$_{14}$) aryl, —(C$_0$-C$_3$)-alkylene-heteroaryl, —NH$_2$, —OH, —C(O)R$_{23}$, —C(O)NR$_{23}$R$_{24}$, —NR$_{23}$C(O)R$_{24}$, —NR$_{23}$R$_{24}$, —S(O)$_q$R$_{23}$, —S(O)$_q$NR$_{23}$R$_{24}$, —NR$_{23}$S(O)$_q$R$_{24}$, Oxo, —P(O)((C$_1$-C$_6$) alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{14}$ is independently D, $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —C(O)(C$_1$-C$_6$) alkyl, —S(O)$_q$(C$_1$-C$_6$) alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—(C$_3$-C$_8$)cycloalkyl, —C(O)O(C$_1$-C$_6$) alkyl, —C(O)NR$_{26}$R$_{27}$, —S(O)$_q$NR$_{26}$R$_{27}$, —NR$_{26}$R$_{27}$, —NR$_{26}$C(O)NR$_{26}$R$_{27}$, —NR$_{26}$C(O)OR$_{27}$, —NR$_{26}$S(O)$_q$R$_{27}$, —NR$_{26}$C(O)R$_{27}$, halogen, —P(O)((C$_1$-C$_6$) alkyl)$_2$, —P(O)(aryl)$_2$, —SiMe$_3$, or —SF$_5$, wherein in the alkyl, aryl, heteroaryl, cycloalkyl, and heterocycloalkyl are optionally substituted with one or more $R_{16}$;

each $R_{16}$ is independently $(C_1-C_6)$ alkyl, $(C_1-C_6)$ alkoxy, $(C_1-C_6)$ haloalkyl, $(C_1-C_6)$ haloalkoxy, halogen, —C(O) $(C_1-C_6)$ alkyl, —S(O)$_q$($C_1-C_6$) alkyl, —NH$_2$, $(C_1-C_6)$ alkylamino, di($C_1-C_6$) alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—($C_3-C_8$)cycloalkyl, —OH, or CN, wherein in the alkyl, aryl, heteroaryl, cycloalkyl, and heterocycloalkyl are optionally substituted with one or more $R_{28}$;

each $R_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —C(O)($C_1-C_6$) alkyl, —S(O)$_q$ $(C_1-C_6)$ alkyl, —NH$_2$, $(C_1-C_6)$ alkylamino, di($C_1-C_6$) alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1-C_6)$ alkyl, $(C_1-C_6)$ alkoxy, $(C_1-C_6)$ haloalkyl, $(C_1-C_6)$ haloalkoxy, halogen, —C(O) $(C_1-C_6)$ alkyl, —S(O)$_q$($C_1-C_6$) alkyl, —NH$_2$, $(C_1-C_6)$ alkylamino, di($C_1-C_6$) alkylamino, —OH, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)(($C_1-C_6$) alkyl)$_2$, —P(O)(aryl)$_2$, —SiMe$_3$, —SF$_5$, —OH, or CN;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —NH$_2$, or CN;

each $R_{21}$ and $R_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, or CN;

each $R_{26}$ and $R_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, —NH$_2$, $(C_1-C_6)$ alkylamino, or di($C_1-C_6$) alkylamino;

each $R_{28}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —C(O)($C_1-C_6$) alkyl, —S(O)$_q$($C_1-C_6$) alkyl, —NH$_2$, $(C_1-C_6)$ alkylamino, di($C_1-C_6$) alkylamino, —OH, or CN;

m is 0, 1, 2, 3, or 4;
n is 0, 1, 2, or 3; and
q is independently at each occurrence 0, 1, or 2.

In another embodiment, the compounds of Formula (I) have the structure of Formula (If):

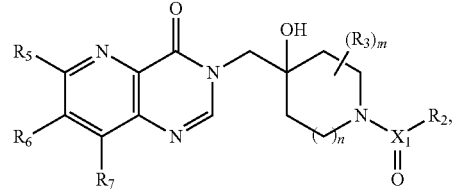

(If)

and pharmaceutically acceptable salts, hydrates, solvates, prodrugs, stereoisomers, and tautomers thereof, wherein:

$X_1$ is C, S, or S(O);

$R_2$ is $(C_1-C_6)$ alkyl, $(C_6-C_{14})$ aryl, heteroaryl, $(C_5-C_8)$ cycloalkyl, heterocycloalkyl, —NR$_{10}$R$_{11}$, or —OR$_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_5$ is H, $(C_1-C_6)$ alkyl, $(C_2-C_6)$ alkenyl, $(C_2-C_6)$ alkynyl, $(C_1-C_6)$ haloalkyl, halogen, NO$_2$, or CN, wherein the alkyl, alkenyl, and alkynyl are optionally substituted with one or more $R_{12}$;

$R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, NO$_2$, —NH$_2$, —NHC(O)($C_1-C_6$) alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1-C_6)$ alkyl, $(C_6-C_{14})$ aryl, heteroaryl, $(C_5-C_8)$ cycloalkyl, heterocycloalkyl, —O-aryl, —O-heteroaryl, —N(($C_1-C_6$) alkyl)-aryl, NH-aryl, —N(($C_1-C_6$) alkyl)-heteroaryl, or —NH-heteroaryl, wherein the alkyl, aryl, heteroaryl, cycloalkyl, and heterocycloalkyl are optionally substituted with one or more $R_{14}$;

each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, —($C_1-C_3$)-alkylene-O—($C_1-C_6$) alkyl, —($C_0-C_4$)-alkylene-aryl, —($C_0-C_4$)-alkylene-heteroaryl, $(C_3-C_{10})$ cycloalkyl, heterocycloalkyl, —($C_0-C_4$)-alkylene-O-aryl, —($C_0-C_4$)-alkylene-O-heteroaryl, —O—($C_3-C_8$)cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O) R$_{22}$, —NR$_{21}$C(O)NR$_{21}$R$_{22}$, —P(O)(($C_1-C_6$) alkyl)$_2$, —P(O) (aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, $(C_3\text{-}C_8)$ cycloalkyl, heterocycloalkyl, —$(C_0\text{-}C_3)$-alkylene-$(C_6\text{-}C_{14})$ aryl, —$(C_0\text{-}C_3)$-alkylene-heteroaryl, —$NH_2$, —OH, —C(O)$R_{23}$, —C(O)$NR_{23}R_{24}$, —$NR_{23}C(O)R_{24}$, —$NR_{23}R_{24}$, —$S(O)_qR_{23}$, —$S(O)_qNR_{23}R_{24}$, —$NR_{23}S(O)_qR_{24}$, oxo, —$P(O)((C_1\text{-}C_6) \text{ alkyl})_2$, —$P(O)(\text{aryl})_2$, —$SiMe_3$, —$SF_5$, —O-aryl, CN, or —O-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1\text{-}C_6)$ alkyl, $(C_6\text{-}C_{14})$ aryl, heteroaryl, $(C_5\text{-}C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{12}$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, CN, —$C(O)(C_1\text{-}C_6)$ alkyl, —$S(O)_q(C_1\text{-}C_6)$ alkyl, —$NH_2$, $(C_1\text{-}C_6)$ alkylamino, or di$(C_1\text{-}C_6)$ alkylamino;

each $R_{13}$ is independently D, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, CN, —OH, —$NH_2$, —$C(O)(C_1\text{-}C_6)$ alkyl, —$S(O)_q(C_1\text{-}C_6)$ alkyl, $(C_1\text{-}C_6)$ alkylamino, di$(C_1\text{-}C_6)$ alkylamino, $(C_6\text{-}C_{14})$ aryl, heteroaryl, $(C_3\text{-}C_8)$ cycloalkyl, heterocycloalkyl, —O-aryl, —O-heteroaryl, —O-heterocycloalkyl, —O—$(C_3\text{-}C_8)$cycloalkyl, —$C(O)O(C_1\text{-}C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1\text{-}C_6) \text{ alkyl})_2$, —$P(O)(\text{aryl})_2$, —$SiMe_3$, or —$SF_5$, wherein in the alkyl, aryl, heteroaryl, cycloalkyl, and heterocycloalkyl are optionally substituted with one or more $R_{15}$;

each $R_{14}$ is independently D, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, CN, —OH, —$NH_2$, —$C(O)(C_1\text{-}C_6)$ alkyl, —$S(O)_q(C_1\text{-}C_6)$ alkyl, $(C_1\text{-}C_6)$ alkylamino, di$(C_1\text{-}C_6)$ alkylamino, $(C_6\text{-}C_{14})$ aryl, heteroaryl, $(C_3\text{-}C_8)$ cycloalkyl, heterocycloalkyl, —O-aryl, —O-heteroaryl, —O-heterocycloalkyl, —O—$(C_3\text{-}C_8)$cycloalkyl, —$C(O)O(C_1\text{-}C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1\text{-}C_6) \text{ alkyl})_2$, —$P(O)(\text{aryl})_2$, —$SiMe_3$, or —$SF_5$, wherein in the alkyl, aryl, heteroaryl, cycloalkyl, and heterocycloalkyl are optionally substituted with one or more $R_{16}$;

each $R_{15}$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —$C(O)(C_1\text{-}C_6)$ alkyl, —$S(O)_q(C_1\text{-}C_6)$ alkyl, —$NH_2$, $(C_1\text{-}C_6)$ alkylamino, di$(C_1\text{-}C_6)$ alkylamino, —OH, or CN;

each $R_{16}$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —$C(O)(C_1\text{-}C_6)$ alkyl, —$S(O)_q(C_1\text{-}C_6)$ alkyl, —$NH_2$, $(C_1\text{-}C_6)$ alkylamino, di$(C_1\text{-}C_6)$ alkylamino, $(C_6\text{-}C_{14})$ aryl, heteroaryl, $(C_3\text{-}C_8)$ cycloalkyl, heterocycloalkyl, —O-aryl, —O-heteroaryl, —O-heterocycloalkyl, —O—$(C_3\text{-}C_8)$cycloalkyl, —OH, or CN, wherein in the alkyl, aryl, heteroaryl, cycloalkyl, and heterocycloalkyl are optionally substituted with one or more $R_{28}$;

each $R_{17}$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, $(C_1\text{-}C_6)$ hydroxyalkyl, —OH, CN, —$C(O)(C_1\text{-}C_6)$ alkyl, —$S(O)_q(C_1\text{-}C_6)$ alkyl, —$NH_2$, $(C_1\text{-}C_6)$ alkylamino, di$(C_1\text{-}C_6)$ alkylamino, $(C_6\text{-}C_{14})$ aryl, heteroaryl, $(C_5\text{-}C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —$C(O)(C_1\text{-}C_6)$ alkyl, —$S(O)_q(C_1\text{-}C_6)$ alkyl, —$NH_2$, $(C_1\text{-}C_6)$ alkylamino, di$(C_1\text{-}C_6)$ alkylamino, —OH, or CN;

each $R_{19}$ is independently at each occurrence $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —$NR_{26}C(O)R_{27}$, —$NR_{26}S(O)_qR_{27}$, —$C(O)R_{26}$, —$C(O)NR_{26}R_{27}$, —$NR_{26}R_{27}$, —$S(O)_qR_{26}$, —$S(O)_qNR_{26}R_{27}$, —$P(O)((C_1\text{-}C_6) \text{ alkyl})_2$, —$P(O)(\text{aryl})_2$, —$SiMe_3$, —$SF_5$, —OH, or CN;

each $R_{20}$ is independently at each occurrence $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —OH, —$NH_2$, or CN;

each $R_{21}$ and $R_{22}$ is independently H, $(C_1\text{-}C_6)$ alkyl, $(C_2\text{-}C_6)$ alkenyl, $(C_2\text{-}C_6)$ alkynyl, $(C_6\text{-}C_{14})$ aryl, heteroaryl, $(C_5\text{-}C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1\text{-}C_6)$ alkyl, $(C_2\text{-}C_6)$ alkenyl, $(C_2\text{-}C_6)$ alkynyl, $(C_6\text{-}C_{14})$ aryl, heteroaryl, $(C_5\text{-}C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —OH, or CN;

each $R_{26}$ and $R_{27}$ is independently at each occurrence H, $(C_1\text{-}C_6)$ alkyl, $(C_2\text{-}C_6)$ alkenyl, $(C_2\text{-}C_6)$ alkynyl, $(C_6\text{-}C_{14})$ aryl, heteroaryl, $(C_5\text{-}C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, —$NH_2$, $(C_1\text{-}C_6)$ alkylamino, or di$(C_1\text{-}C_6)$ alkylamino;

each $R_{28}$ is independently at each occurrence $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —$C(O)(C_1\text{-}C_6)$ alkyl, —$S(O)_q(C_1\text{-}C_6)$ alkyl, —$NH_2$, $(C_1\text{-}C_6)$ alkylamino, di$(C_1\text{-}C_6)$ alkylamino, —OH, or CN;

m is 0, 1, 2, 3, or 4;

n is 0, 1, 2, or 3;

q is independently at each occurrence 0, 1, or 2.

In another embodiment, the compounds of Formula (I) have the structure of Formula (Ig):

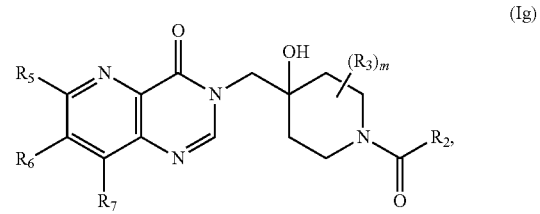

(Ig)

and pharmaceutically acceptable salts, hydrates, solvates, prodrugs, stereoisomers, and tautomers thereof, wherein:

$R_2$ is $(C_1-C_6)$ alkyl, $(C_6-C_{14})$ aryl, heteroaryl, $(C_5-C_8)$ cycloalkyl, heterocycloalkyl, —$NR_{10}R_{11}$, or —$OR_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_5$ is H, $(C_1-C_6)$ alkyl, $(C_2-C_6)$ alkenyl, $(C_2-C_6)$ alkynyl, $(C_1-C_6)$ haloalkyl, halogen, $NO_2$, or CN, wherein the alkyl, alkenyl, and alkynyl are optionally substituted with one or more $R_{12}$;

$R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, $NO_2$, —$NH_2$, —$NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$;

$R_7$ is H, $(C_1-C_6)$ alkyl, $(C_6-C_{14})$ aryl, heteroaryl, $(C_5-C_8)$ cycloalkyl, heterocycloalkyl, —O-aryl, —O-heteroaryl, —N$((C_1-C_6)$ alkyl)-aryl, NH-aryl, —N$((C_1-C_6)$ alkyl)-heteroaryl, or —NH-heteroaryl, wherein the alkyl, aryl, heteroaryl, cycloalkyl, and heterocycloalkyl are optionally substituted with one or more $R_{14}$;

each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, —$(C_1-C_3)$-alkylene-O—$(C_1-C_6)$ alkyl, —$(C_0-C_4)$-alkylene-aryl, —$(C_0-C_4)$-alkylene-heteroaryl, $(C_3-C_{10})$ cycloalkyl, heterocycloalkyl, —$(C_0-C_4)$-alkylene-O-aryl, —$(C_0-C_4)$-alkylene-O-heteroaryl, —O—$(C_3-C_8)$cycloalkyl, —S-heteroaryl, —$C(O)R_{21}$, —$CO(O)R_{21}$, —$C(O)NR_{21}R_{22}$, —$S(O)_qR_{21}$, —$S(O)_qNR_{21}R_{22}$, —$NR_{21}S(O)_qR_{22}$, —$(C_0-C_3)$-alkylene-$NR_{21}R_{22}$, —$NR_{21}C(O)R_{22}$, —$NR_{21}C(O)C(O)R_{22}$, —$NR_{21}C(O)NR_{21}R_{22}$, —$P(O)((C_1-C_6)$ alkyl$)_2$, —$P(O)(aryl)_2$, —$SiMe_3$, —$SF_5$, or —$OR_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, —$(C_0-C_3)$-alkylene-$(C_6-C_{14})$ aryl, —$(C_0-C_3)$-alkylene-heteroaryl, —$NH_2$, —OH, —$C(O)R_{23}$, —$C(O)NR_{23}R_{24}$, —$NR_{23}C(O)R_{24}$, —$NR_{23}R_{24}$, —$S(O)_qR_{23}$, —$S(O)_qNR_{23}R_{24}$, —$NR_{23}S(O)_qR_{24}$, Oxo, —$P(O)((C_1-C_6)$ alkyl$)_2$, —$P(O)(aryl)_2$, —$SiMe_3$, —$SF_5$, —O-aryl, CN, or —O-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{12}$ is independently $(C_1-C_6)$ alkyl, $(C_1-C_6)$ alkoxy, $(C_1-C_6)$ haloalkyl, $(C_1-C_6)$ haloalkoxy, halogen, CN, —$C(O)(C_1-C_6)$ alkyl, —$S(O)_q(C_1-C_6)$ alkyl, —$NH_2$, $(C_1-C_6)$ alkylamino, or di$(C_1-C_6)$ alkylamino;

each $R_{13}$ is independently D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one or more $R_{15}$;

each $R_{14}$ is independently D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one or more $R_{16}$;

each $R_{15}$ is independently $(C_1-C_6)$ alkyl, $(C_1-C_6)$ alkoxy, $(C_1-C_6)$ haloalkyl, $(C_1-C_6)$ haloalkoxy, halogen, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, —OH, or CN;

each $R_{16}$ is independently $(C_1-C_6)$ alkyl, $(C_1-C_6)$ alkoxy, $(C_1-C_6)$ haloalkyl, $(C_1-C_6)$ haloalkoxy, halogen, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —OH, or CN, wherein in the alkyl, aryl, heteroaryl, cycloalkyl, and heterocycloalkyl are optionally substituted with one or more $R_{28}$;

each $R_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1-C_6)$ alkyl, $(C_1-C_6)$ alkoxy, $(C_1-C_6)$ haloalkyl, $(C_1-C_6)$ haloalkoxy, halogen, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, —OH, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)((C$_1$-C$_6$) alkyl)$_2$, —P(O)(aryl)$_2$, —SiMe$_3$, —SF$_5$, —OH, or CN;

each R$_{20}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —OH, —NH$_2$, or CN;

each R$_{21}$ and R$_{22}$ is independently H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, aryl, heteroaryl, cycloalkyl and heterocycloalkyl are optionally substituted with one or more R$_{25}$;

each R$_{23}$ and R$_{24}$ is independently H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, aryl, heteroaryl, cycloalkyl and heterocycloalkyl are optionally substituted with one or more R$_{25}$;

each R$_{25}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —OH, or CN;

each R$_{26}$ and R$_{27}$ is independently at each occurrence H, (C$_1$-C$_6$) alkyl, (C$_2$-C$_6$) alkenyl, (C$_2$-C$_6$) alkynyl, (C$_6$-C$_{14}$) aryl, heteroaryl, (C$_5$-C$_8$) cycloalkyl, or heterocycloalkyl, wherein the alkyl, alkenyl, alkynyl, aryl, heteroaryl, cycloalkyl and heterocycloalkyl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, —NH$_2$, (C$_1$-C$_6$) alkylamino, or di(C$_1$-C$_6$) alkylamino;

each R$_{28}$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —C(O)(C$_1$-C$_6$) alkyl, —S(O)$_q$(C$_1$-C$_6$) alkyl, —NH$_2$, (C$_1$-C$_6$) alkylamino, di(C$_1$-C$_6$) alkylamino, —OH, or CN;

m is 0, 1, 2, 3, or 4; and q is independently at each occurrence 0, 1, or 2.

In another embodiment, the compounds of Formula (I) have the structure of Formula (Ih):

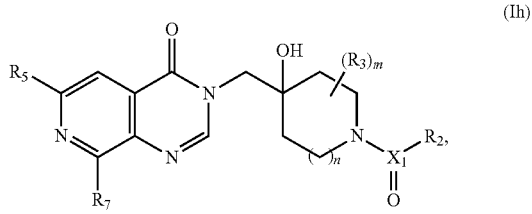

(Ih)

and pharmaceutically acceptable salts, hydrates, solvates, prodrugs, stereoisomers, and tautomers thereof, wherein:

X$_1$ is C, S, or S(O);

R$_2$ is (C$_1$-C$_6$) alkyl, (C$_6$-C$_{14}$) aryl, heteroaryl, (C$_5$-C$_8$) cycloalkyl, heterocycloalkyl, —NR$_{10}$R$_{11}$, or —OR$_{10}$; wherein the alkyl, aryl, heteroaryl, cycloalkyl, and heterocycloalkyl are optionally substituted with one or more R$_8$;

each R$_3$ is independently at each occurrence selected from D, (C$_1$-C$_6$) alkyl, (C$_6$-C$_{14}$) aryl, heteroaryl, (C$_3$-C$_8$) cycloalkyl, or heterocycloalkyl, wherein the alkyl, aryl, heteroaryl, cycloalkyl, and heterocycloalkyl are optionally substituted with one or more R$_{20}$; or two R$_3$ together when on adjacent carbons form a (C$_3$-C$_8$) cycloalkyl optionally substituted with one or more R$_{20}$; or two R$_3$ together when attached to the same carbon atom form a (C$_3$-C$_8$) spirocycloalkyl optionally substituted with one or more R$_{20}$; or two R$_3$ together when attached to the same carbon atom form a spiroheterocycloalkyl optionally substituted with one or more R$_{20}$; or two R$_3$ together when on adjacent carbons form an aryl ring optionally substituted with one or more R$_{20}$; or two R$_3$ together when on adjacent carbons form an heteroaryl ring optionally substituted with one or more R$_{20}$;

R$_5$ is H, (C$_1$-C$_6$) alkyl, (C$_2$-C$_6$) alkenyl, (C$_2$-C$_6$) alkynyl, (C$_1$-C$_6$) haloalkyl, halogen, NO$_2$, or CN, wherein the alkyl, alkenyl, and alkynyl are optionally substituted with one or more R$_{12}$;

R$_7$ is H, (C$_1$-C$_6$) alkyl, (C$_6$-C$_{14}$) aryl, heteroaryl, (C$_5$-C$_8$) cycloalkyl, heterocycloalkyl, —O-aryl, —O-heteroaryl, —N((C$_1$-C$_6$) alkyl)-aryl, NH-aryl, —N((C$_1$-C$_6$) alkyl)-heteroaryl, or —NH-heteroaryl, wherein the alkyl, aryl, heteroaryl, cycloalkyl, and heterocycloalkyl are optionally substituted with one or more R$_{14}$;

each R$_8$ is independently D, (C$_1$-C$_6$) alkyl, (C$_1$-C$_6$) alkoxy, (C$_1$-C$_6$) haloalkyl, (C$_1$-C$_6$) haloalkoxy, halogen, CN, —(C$_1$-C$_3$)-alkylene-O—(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocycloalkyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, —C(O)R$_{21}$, —CO(O)R$_{21}$, —C(O)NR$_{21}$R$_{22}$, —S(O)$_q$R$_{21}$, —S(O)$_q$NR$_{21}$R$_{22}$, —NR$_{21}$S(O)$_q$R$_{22}$, —(C$_0$-C$_3$)-alkylene-NR$_{21}$R$_{22}$, —NR$_{21}$C(O)R$_{22}$, —NR$_{21}$C(O)C(O)R$_{22}$, —NR$_{21}$C(O)NR$_{21}$R$_{22}$, —P(O)((C$_1$-C$_6$) alkyl)$_2$, —P(O)(aryl)$_2$, —SiMe$_3$, —SF$_5$, or —OR$_{21}$, wherein the alkyl, alkylene, aryl, heteroaryl, cycloalkyl, and heterocycloalkyl are optionally substituted with one or more R$_9$; or two R$_8$ together when on adjacent atoms form a (C$_3$-C$_8$) cycloalkyl optionally substituted with one or more R$_9$; or two R$_8$ together when on adjacent atoms form a heterocycloalkyl ring optionally substituted with one or more R$_9$; or two R$_8$ together when on adjacent atoms form an aryl ring optionally substituted with one or more R$_9$; or two R$_8$ together when on adjacent atoms form an heteroaryl ring optionally substituted with one or more R$_9$;

each R$_9$ is independently (C$_1$-C$_6$) alkyl, (C$_1$-C$_6$) alkoxy, (C$_1$-C$_6$) haloalkyl, (C$_1$-C$_6$) haloalkoxy, halogen, (C$_3$-C$_8$) cycloalkyl, heterocycloalkyl, —(C$_0$-C$_3$)-alkylene-(C$_6$-C$_{14}$) aryl, —(C$_0$-C$_3$)-alkylene-heteroaryl, —NH$_2$, —OH, —C(O)R$_{23}$, —C(O)NR$_{23}$R$_{24}$, —NR$_{23}$C(O)R$_{24}$, —NR$_{23}$R$_{24}$, —S(O)$_q$R$_{23}$, —S(O)$_q$NR$_{23}$R$_{24}$, —NR$_{23}$S(O)$_q$R$_{24}$, Oxo, —P(O)((C$_1$-C$_6$) alkyl)$_2$, —P(O)(aryl)$_2$, —SiMe$_3$, —SF$_5$, —O-aryl, CN, or —O-heteroaryl, wherein alkyl, aryl, heteroaryl, cycloalkyl, and heterocycloalkyl are optionally substituted with one or more R$_{19}$;

R$_{10}$ and R$_{11}$ are independently H, (C$_1$-C$_6$) alkyl, (C$_6$-C$_{14}$) aryl, heteroaryl, (C$_5$-C$_8$) cycloalkyl, or heterocycloalkyl, wherein the alkyl, aryl, heteroaryl, cycloalkyl, and heterocycloalkyl are optionally substituted with one or more R$_{17}$; or R$_{10}$ and R$_{11}$ together with the nitrogen to which they are attached form a heterocycloalkyl ring optionally substituted with one or more R$_{17}$;

each R$_{12}$ is independently (C$_1$-C$_6$) alkyl, (C$_1$-C$_6$) alkoxy, (C$_1$-C$_6$) haloalkyl, (C$_1$-C$_6$) haloalkoxy, halogen, CN, —C(O)(C$_1$-C$_6$) alkyl, —S(O)$_q$(C$_1$-C$_6$) alkyl, —NH$_2$, (C$_1$-C$_6$) alkylamino, or di(C$_1$-C$_6$) alkylamino;

each R$_{14}$ is independently D, (C$_1$-C$_6$) alkyl, (C$_1$-C$_6$) alkoxy, (C$_1$-C$_6$) haloalkyl, (C$_1$-C$_6$) haloalkoxy, halogen, CN, —OH, —NH$_2$, —C(O)(C$_1$-C$_6$) alkyl, —S(O)$_q$(C$_1$-C$_6$) alkyl, (C$_1$-C$_6$) alkylamino, di(C$_1$-C$_6$) alkylamino, (C$_6$-C$_{14}$) aryl, heteroaryl, (C$_3$-C$_8$) cycloalkyl, heterocycloalkyl, —O-aryl, —O-heteroaryl, —O-heterocycloalkyl, —O—(C$_3$-C$_8$)cycloalkyl, —C(O)O(C$_1$-C$_6$) alkyl, —C(O)NR$_{26}$R$_{27}$, —S(O)$_q$ $NR_{26}R_{27}$, $-NR_{26}R_{27}$, $-NR_{26}C(O)NR_{26}R_{27}$, $-NR_{26}C(O)$ $OR_{27}$, $-NR_{26}S(O)_qR_{27}$, $-NR_{26}C(O)R_{27}$, halogen, $-P(O)$ $((C_1-C_6)$ alkyl$)_2$, $-P(O)(aryl)_2$, $-SiMe_3$, or $-SF_5$, wherein in the alkyl, aryl, heteroaryl, cycloalkyl, and heterocycloalkyl are optionally substituted with one or more $R_{16}$;

each $R_{16}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)$ $(C_1-C_6)$ alkyl, $-S(O)_q(C_1-C_6)$ alkyl, $-NH_2$, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, $-O$-aryl, $-O$-heteroaryl, $-O$-heterocycloalkyl, $-O-(C_3-C_8)$cycloalkyl, $-OH$, or CN, wherein in the alkyl, aryl, heteroaryl, cycloalkyl, and heterocycloalkyl are optionally substituted with one or more $R_{28}$;

each $R_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, $-OH$, CN, $-C(O)(C_1-C_6)$ alkyl, $-S(O)_q$ $(C_1-C_6)$ alkyl, $-NH_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$;

each $R_{18}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)$ $(C_1-C_6)$ alkyl, $-S(O)_q(C_1-C_6)$ alkyl, $-NH_2$, $(C_1-C_6)$ alkylamino, di$(C_1-C_6)$ alkylamino, $-OH$, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-NR_{26}C(O)R_{27}$, $-NR_{26}S(O)_qR_{27}$, $-C(O)R_{26}$, $-C(O)NR_{26}R_{27}$, $-NR_{26}R_{27}$, $-S(O)_qR_{26}$, $-S(O)_qNR_{26}R_{27}$, $-P(O)((C_1-C_6)$ alkyl$)_2$, $-P(O)(aryl)_2$, $-SiMe_3$, $-SF_5$, $-OH$, or CN;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-OH$, $-NH_2$, or CN;

each $R_{21}$ and $R_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-OH$, or CN;

each $R_{26}$ and $R_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $-NH_2$, $(C_1-C_6)$ alkylamino, or di$(C_1-C_6)$ alkylamino;

each $R_{28}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $-OH$, or CN;

m is 0, 1, 2, 3, or 4;
n is 0, 1, 2, or 3; and
q is independently at each occurrence 0, 1, or 2.

In another embodiment, the compounds of Formula (I) have the structure of Formula (Ii):

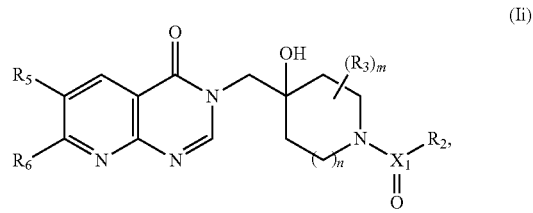

(Ii)

and pharmaceutically acceptable salts, hydrates, solvates, prodrugs, stereoisomers, and tautomers thereof,
wherein:

$X_1$ is C, S, or S(O);

$R_2$ is $(C_1-C_6)$ alkyl, $(C_6-C_{14})$ aryl, heteroaryl, $(C_5-C_8)$ cycloalkyl, heterocycloalkyl, $-NR_{10}R_{11}$, or $-OR_{10}$, wherein the alkyl, aryl, heteroaryl, cycloalkyl, and heterocycloalkyl are optionally substituted with one or more $R_8$;

each $R_3$ is independently at each occurrence selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$; or two $R_3$ together when on adjacent carbons form a $(C_3-C_8)$ cycloalkyl optionally substituted with one or more $R_{20}$; or two $R_3$ together when attached to the same carbon atom form a $(C_3-C_8)$ spirocycloalkyl optionally substituted with one or more $R_{20}$; or two $R_3$ together when attached to the same carbon atom form a spiroheterocycloalkyl optionally substituted with one or more $R_{20}$; or two $R_3$ together when on adjacent carbons form an aryl ring optionally substituted with one or more $R_{20}$; or two $R_3$ together when on adjacent carbons form an heteroaryl ring optionally substituted with one or more $R_{20}$;

$R_5$ is H, $(C_1-C_6)$ alkyl, $(C_2-C_6)$ alkenyl, $(C_2-C_6)$ alkynyl, $(C_1-C_6)$ haloalkyl, halogen, $NO_2$, or CN, wherein the alkyl, alkenyl, and alkynyl are optionally substituted with one or more $R_{12}$;

$R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, $NO_2$, $-NH_2$, $-NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$; or each $R_8$ is independently D, $(C_1-C_6)$ alkyl, $(C_1-C_6)$ alkoxy, $(C_1-C_6)$ haloalkyl, $(C_1-C_6)$ haloalkoxy, halogen, CN, $-(C_1-C_3)$-alkylene-O$-(C_1-C_6)$ alkyl, $-(C_0-C_4)$-alkylene-aryl, $-(C_0-C_4)$-alkylene-heteroaryl, $(C_3-C_{10})$ cycloalkyl, heterocycloalkyl, $-(C_0-C_4)$-alkylene-O-aryl, $-(C_0-C_4)$-alkylene-O-heteroaryl, $-O-(C_3-C_8)$cycloalkyl, $-S$-heteroaryl, $-C(O)R_{21}$, $-CO(O)R_{21}$, $-C(O)NR_{21}R_{22}$, $-S(O)_qR_{21}$, $-S(O)_qNR_{21}R_{22}$, $-NR_{21}S(O)_qR_{22}$, $-(C_0-C_3)$-alkylene-$NR_{21}R_{22}$, $-NR_{21}C(O)R_{22}$, $-NR_{21}C(O)C(O)R_{22}$, $-NR_{21}C(O)NR_{21}R_{22}$, $-P(O)((C_1-C_6)$ alkyl$)_2$, $-P(O)(aryl)_2$, $-SiMe_3$, $-SF_5$, or $-OR_{21}$, wherein the alkyl, alkylene, aryl, heteroaryl, cycloalkyl, and heterocycloalkyl are optionally substituted with one or more $R_9$; or two $R_8$ together when on adjacent atoms form a $(C_3-C_8)$ cycloalkyl optionally substituted with one or more $R_9$; or two $R_8$ together when on adjacent atoms form a heterocycloalkyl ring optionally substituted with one or more $R_9$; or two $R_8$ together when on adjacent atoms form an aryl ring optionally substituted with one or more $R_9$; or two $R_8$ together when on adjacent atoms form an heteroaryl ring optionally substituted with one or more $R_9$;

each $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, $-(C_0-C_3)$-alkylene-$(C_6-C_{14})$ aryl, $-(C_0-C_3)$-alkylene-heteroaryl, $-NH_2$, $-OH$, $-C(O)R_{23}$, $-C(O)NR_{23}R_{24}$, $-NR_{23}C(O)R_{24}$, $-NR_{23}R_{24}$, $-S(O)_qR_{23}$, $-S(O)_qNR_{23}R_{24}$, $-NR_{23}S(O)_qR_{24}$, oxo, $-P(O)((C_1-C_6)$ alkyl$)_2$, $-P(O)(aryl)_2$, $-SiMe_3$, $-SF_5$, $-O$-aryl, CN, or $-O$-heteroaryl, wherein alkyl, aryl, heteroaryl, cycloalkyl, and heterocycloalkyl are optionally substituted with one or more $R_{19}$;

$R_{10}$ and $R_{11}$ are independently H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$; or $R_{10}$ and $R_{11}$ together with the nitrogen to which they are attached form a heterocycloalkyl ring optionally substituted with one or more $R_{17}$;

each $R_{12}$ is independently $(C_1-C_6)$ alkyl, $(C_1-C_6)$ alkoxy, $(C_1-C_6)$ haloalkyl, $(C_1-C_6)$ haloalkoxy, halogen, CN, $-C(O)(C_1-C_6)$ alkyl, $-S(O)_q(C_1-C_6)$ alkyl, $-NH_2$, $(C_1-C_6)$ alkylamino, or di$(C_1-C_6)$ alkylamino;

each $R_{13}$ is independently D, $(C_1-C_6)$ alkyl, $(C_1-C_6)$ alkoxy, $(C_1-C_6)$ haloalkyl, $(C_1-C_6)$ haloalkoxy, halogen, CN, $-OH$, $-NH_2$, $-C(O)(C_1-C_6)$ alkyl, $-S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, $-O$-aryl, $-O$-heteroaryl, $-O$-heterocycloalkyl, $-O-(C_3-C_8)$cycloalkyl, $-C(O)O(C_1-C_6)$ alkyl, $-C(O)NR_{26}R_{27}$, $-S(O)_qNR_{26}R_{27}$, $-NR_{26}R_{27}$, $-NR_{26}C(O)NR_{26}R_{27}$, $-NR_{26}C(O)OR_{27}$, $-NR_{26}S(O)_qR_{27}$, $-NR_{26}C(O)R_{27}$, halogen, $-P(O)((C_1-C_6)$ alkyl$)_2$, $-P(O)(aryl)_2$, $-SiMe_3$, or $-SF_5$, wherein in the alkyl, aryl, heteroaryl, cycloalkyl, and heterocycloalkyl are optionally substituted with one or more $R_{15}$;

each $R_{15}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $-OH$, or CN;

each $R_{17}$ is independently $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, $-OH$, CN, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$;

each $R_{11}$ is independently $(C_1-C_6)$ alkyl, $(C_1-C_6)$ alkoxy, $(C_1-C_6)$ haloalkyl, $(C_1-C_6)$ haloalkoxy, halogen, $-C(O)(C_1-C_6)$ alkyl, $-S(O)_q(C_1-C_6)$ alkyl, $-NH_2$, $(C_1-C_6)$ alkylamino, di$(C_1-C_6)$ alkylamino, $-OH$, or CN;

each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-NR_{26}C(O)R_{27}$, $-NR_{26}S(O)_qR_{27}$, $-C(O)R_{26}$, $-C(O)NR_{26}R_{27}$, $-NR_{26}R_{27}$, $-S(O)_qR_{26}$, $-S(O)_qNR_{26}R_{27}$, $-P(O)((C_1-C_6)$ alkyl$)_2$, $-P(O)(aryl)_2$, $-SiMe_3$, $-SF_5$, $-OH$, or CN;

each $R_{20}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-OH$, $-NH_2$, or CN;

each $R_{21}$ and $R_{22}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{23}$ and $R_{24}$ is independently H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, aryl, heteroaryl, cycloalkyl and heterocycloalkyl are optionally substituted with one or more $R_{25}$;

each $R_{25}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-OH$, or CN;

each $R_{26}$ and $R_{27}$ is independently at each occurrence H, $(C_1-C_6)$ alkyl, $(C_2-C_6)$ alkenyl, $(C_2-C_6)$ alkynyl, $(C_6-C_{14})$ aryl, heteroaryl, $(C_5-C_8)$ cycloalkyl, or heterocycloalkyl, wherein the alkyl, alkenyl, alkynyl, aryl, heteroaryl, cycloalkyl and heterocycloalkyl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $-NH_2$, $(C_1-C_6)$ alkylamino, or di$(C_1-C_6)$ alkylamino;

m is 0, 1, 2, 3, or 4;

n is 0, 1, 2, or 3; and q is independently at each occurrence 0, 1, or 2.

In some embodiments of the Formulae above, $X_1$ is C. In another embodiment, $X_1$ is S. In yet another embodiment, $X_1$ is S(O).

In some embodiments of the Formulae above, $Y_1$ is N. In another embodiment, $Y_1$ is CH.

In some embodiments of the Formulae above, $Y_2$ is N. In another embodiment, $Y_2$ is $CR_5$.

In some embodiments of the Formulae above, $Y_3$ is N. In another embodiment, $Y_3$ is $CR_6$.

In some embodiments of the Formulae above, $Y_4$ is N. In another embodiment, $Y_4$ is $CR_7$.

In some embodiments of the Formulae above, $R_1$ is H, $-OH$, $-SH$, $-NH_2$, or F. In another embodiment, $R_1$ is H, $-OH$, or F. In yet another embodiment, $R_1$ is $-OH$, or F. In another embodiment, $R_1$ is $-OH$.

In some embodiments of the Formulae above, $R_2$ is $(C_1-C_6)$ alkyl, $(C_6-C_{14})$ aryl, heteroaryl, $(C_5-C_8)$ cycloalkyl, heterocycloalkyl, $NR_{10}R_{11}$, or $-OR_{10}$, wherein the alkyl, aryl, heteroaryl, cycloalkyl and heterocycloalkyl are optionally substituted with one or more $R_8$. In another embodiment, $R_2$ is $(C_1-C_6)$ alkyl, $(C_6-C_{14})$ aryl, heteroaryl, $(C_5-C_8)$ cycloalkyl, heterocycloalkyl, or $NR_{10}R_{11}$, wherein the alkyl, aryl, heteroaryl, cycloalkyl and heterocycloalkyl are optionally substituted with one or more $R_8$. In yet another embodiment, $R_2$ is $(C_1-C_6)$ alkyl, $(C_6-C_{14})$ aryl, heteroaryl, $(C_5-C_8)$ cycloalkyl, heterocycloalkyl, or $NR_{10}R_{11}$, wherein the alkyl, aryl, heteroaryl, cycloalkyl and heterocycloalkyl are optionally substituted with one to three $R_8$. In another embodiment, $R_2$ is $(C_1-C_4)$ alkyl, $(C_6-C_{14})$ aryl, heteroaryl, or $NR_{10}R_{11}$, wherein the alkyl, aryl, or heteroaryl are optionally substituted with one to three $R_8$. In yet another embodiment, $R_2$ is $(C_1-C_4)$ alkyl, $(C_6-C_{14})$ aryl, or $NR_{10}R_{11}$, wherein the alkyl and aryl are optionally substituted with one to three $R_8$.

In some embodiments of the Formulae above, $R_3$ is selected from D, $(C_1-C_6)$ alkyl, $(C_6-C_{14})$ aryl, heteroaryl, $(C_3-C_8)$ cycloalkyl, or heterocycloalkyl, wherein the alkyl, aryl, heteroaryl, cycloalkyl, and heterocycloalkyl are optionally substituted with one or more $R_{20}$. In another embodiment, $R_3$ is selected from D or $(C_1-C_6)$ alkyl, optionally substituted with one or more $R_{20}$. In yet another embodiment, $R_3$ is selected from D or $(C_1-C_6)$ alkyl, optionally substituted with one to three $R_{20}$. In another embodiment, $R_3$ is selected from D or $(C_1-C_4)$ alkyl, optionally substituted with one to three $R_{20}$.

In another embodiment, two $R_3$ together when on adjacent carbons form a $(C_3-C_8)$ cycloalkyl optionally substituted with one or more $R_{20}$. In another embodiment, two $R_3$ together when attached to the same carbon atom form a $(C_3-C_8)$ spirocycloalkyl optionally substituted with one or more $R_{20}$. In another embodiment, two $R_3$ together when attached to the same carbon atom form a spiroheterocycloalkyl optionally substituted with one or more $R_{20}$. In another embodiment, two $R_3$ together when on adjacent carbons form an aryl ring optionally substituted with one or more $R_{20}$. In another embodiment, two $R_3$ together when on adjacent carbons form a heteroaryl ring optionally substituted with one or more $R_{20}$.

In some embodiments of the Formulae above, $R_4$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, or CN. In another embodiment, $R_4$ is H, D, $(C_1-C_6)$ alkyl, $(C_1-C_6)$ alkoxy, $(C_1-C_6)$ haloalkyl, $(C_1-C_6)$ haloalkoxy, or halogen. In yet another embodiment, $R_4$ is H, D, $(C_1-C_3)$ alkyl, $(C_1-C_3)$ alkoxy, $(C_1-C_3)$ haloalkyl, $(C_1-C_3)$ haloalkoxy, or halogen. In another embodiment, $R_4$ is H, D, $(C_1-C_3)$ alkyl, or halogen. In yet another embodiment, $R_4$ is H, D, methyl, ethyl, propyl, iso-propyl, or halogen.

In some embodiments of the Formulae above, $R_{4'}$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, or CN. In another embodiment, $R_{4'}$ is H, D, $(C_1-C_6)$ alkyl, $(C_1-C_6)$ alkoxy, $(C_1-C_6)$ haloalkyl, $(C_1-C_6)$ haloalkoxy, or halogen. In yet another embodiment, $R_{4'}$ is H, D, $(C_1-C_3)$ alkyl, $(C_1-C_3)$ alkoxy, $(C_1-C_3)$ haloalkyl, $(C_1-C_3)$ haloalkoxy, or halogen. In another embodiment, $R_{4'}$ is H, D, $(C_1-C_3)$ alkyl, or halogen. In yet another embodiment, $R_{4'}$ is H, D, methyl, ethyl, propyl, iso-propyl, or halogen.

In some embodiments of the Formulae above, $R_5$ is H, $(C_1-C_6)$ alkyl, $(C_2-C_6)$ alkenyl, $(C_2-C_6)$ alkynyl, $(C_1-C_6)$ haloalkyl, halogen, $NO_2$, or CN, wherein the alkyl, alkenyl, and alkynyl are optionally substituted with one or more $R_{12}$. In another embodiment, $R_5$ is H, $(C_1-C_6)$ alkyl, $(C_2-C_6)$ alkenyl, $(C_2-C_6)$ alkynyl, $(C_1-C_6)$ haloalkyl, halogen, $NO_2$, or CN, wherein the alkyl, alkenyl, and alkynyl are optionally substituted with one to three $R_{12}$. In yet another embodiment, $R_5$ is H, $(C_1-C_6)$ alkyl, $(C_1-C_6)$ haloalkyl, halogen, $NO_2$, or CN, wherein the alkyl is optionally substituted with one to three $R_{12}$. In another embodiment, $R_5$ is H or $(C_1-C_6)$ alkyl optionally substituted with one to three $R_{12}$.

In some embodiments of the Formulae above, $R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, $NO_2$, $-NH_2$, $-NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{13}$. In another embodiment, $R_6$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, CN, $NO_2$, $-NH_2$, $-NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one to three $R_{13}$. In yet another embodiment, $R_6$ is H, $(C_1-C_6)$ alkyl, $(C_1-C_6)$ alkoxy, $-NH_2$, $-NHC(O)(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one to three $R_{13}$. In another embodiment, $R_6$ is H, $(C_1-C_6)$ alkyl, $(C_1-C_6)$ alkoxy, $-NH_2$, $-NHC(O)(C_1-C_6)$ alkyl, $(C_6-C_{14})$ aryl, or heteroaryl, wherein the alkyl, aryl, and heteroaryl are optionally substituted with one to three $R_{13}$.

In some embodiments of the Formulae above, $R_7$ is H, $(C_1-C_6)$ alkyl, $(C_6-C_{14})$ aryl, heteroaryl, $(C_5-C_8)$ cycloalkyl, heterocycloalkyl, $-O$-aryl, $-O$-heteroaryl, $-N((C_1-C_6)$ alkyl)-aryl, NH-aryl, $-N((C_1-C_6)$ alkyl)-heteroaryl, or $-NH$-heteroaryl, wherein the alkyl, aryl, heteroaryl, cycloalkyl, and heterocycloalkyl are optionally substituted with one or more $R_{14}$. In another embodiment, $R_7$ is H, $(C_1-C_6)$ alkyl, $(C_6-C_{14})$ aryl, heteroaryl, $(C_5-C_8)$ cycloalkyl, heterocycloalkyl, $-O$-aryl, $-O$-heteroaryl, $-N((C_1-C_6)$ alkyl)-aryl, NH-aryl, $-N((C_1-C_6)$ alkyl)-heteroaryl, or $-NH$-heteroaryl, wherein the alkyl, aryl, heteroaryl, cycloalkyl, and heterocycloalkyl are optionally substituted with one to three $R_{14}$. In yet another embodiment, $R_7$ is H, $(C_1-C_6)$ alkyl, $(C_6-C_{14})$ aryl, heteroaryl, $-O$-aryl, or $-O$-heteroaryl, wherein the alkyl, aryl, and heteroaryl are optionally substituted with one to three $R_{14}$. In another embodiment, $R_7$ is H, $(C_1-C_6)$ alkyl, $(C_6-C_{14})$ aryl, or $-O$-aryl, wherein the alkyl and aryl are optionally substituted with one to three $R_{14}$.

In some embodiments of the Formulae above, each $R_8$ is D, $(C_1-C_6)$ alkyl, $(C_1-C_6)$ alkoxy, $(C_1-C_6)$ haloalkyl, $(C_1-C_6)$ haloalkoxy, halogen, CN, $-(C_1-C_3)$-alkylene-O-$(C_1-C_6)$ alkyl, $-(C_0-C_4)$-alkylene-aryl, $-(C_0-C_4)$-alkylene-heteroaryl, $(C_3-C_{10})$ cycloalkyl, heterocycloalkyl, $-(C_0-C_4)$-alkylene-O-aryl, $-(C_0-C_4)$-alkylene-O-heteroaryl, $-O-(C_3-C_8)$cycloalkyl, $-S$-heteroaryl, $-C(O)R_{21}$, $-CO(O)R_{21}$, $-C(O)NR_{21}R_{22}$, $-S(O)_qR_{21}$, $-S(O)_qNR_{21}R_{22}$, $-NR_{21}S(O)_qR_{22}$, $-(C_0-C_3)$-alkylene-$NR_{21}R_{22}$, $-NR_{21}C(O)R_{22}$, $-NR_{21}C(O)C(O)R_{22}$, $-NR_{21}C(O)NR_{21}R_{22}$, $-P(O)((C_1-C_6)$ alkyl)$_2$, $-P(O)(aryl)_2$, $-SiMe_3$, $-SF_5$, or $-OR_{21}$, wherein the alkyl, alkylene, aryl, heteroaryl, cycloalkyl, and heterocycloalkyl are optionally substituted with one or more $R_9$. In another embodiment, each $R_8$ is D, $(C_1-C_6)$ alkyl, $(C_1-C_6)$ alkoxy, $(C_1-C_6)$ haloalkyl, $(C_1-C_6)$ haloalkoxy, halogen, CN, $-(C_1-C_3)$-alkylene-O-$(C_1-C_6)$ alkyl, $-(C_0-C_4)$-alkylene-aryl, $-(C_0-C_4)$-alkylene-heteroaryl, $(C_3-C_{10})$ cycloalkyl, heterocycloalkyl, $-(C_0-C_4)$-alkylene-O-aryl, $-(C_0-C_4)$-alkylene-O-heteroaryl, $-O-(C_3-C_8)$cycloalkyl, $-S$-heteroaryl, $-C(O)R_{21}$, $-CO(O)R_{21}$, $-C(O)NR_{21}R_{22}$, $-S(O)_qR_{21}$, $-S(O)_qNR_{21}R_{22}$, $-NR_{21}S(O)_qR_{22}$, $-(C_0-C_3)$-alkylene-$NR_{21}R_{22}$, $-NR_{21}C(O)R_{22}$, $-NR_{21}C(O)C(O)R_{22}$, $-NR_{21}C(O)NR_{21}R_{22}$, $-P(O)((C_1-C_6)$ alkyl)$_2$, $-P(O)(aryl)_2$, $-SiMe_3$, $-SF_5$, or $-OR_{21}$, wherein the alkyl, alkylene, aryl, heteroaryl, cycloalkyl, and heterocycloalkyl are optionally substituted with one to three $R_9$.

In another embodiment, two $R_8$ together when on adjacent atoms form a $(C_3-C_8)$ cycloalkyl optionally substituted with one or more $R_9$. In yet another embodiment, two $R_8$ together when on adjacent atoms form a heterocycloalkyl ring optionally substituted with one or more $R_9$. In another embodiment, two $R_8$ together when on adjacent atoms form an aryl ring optionally substituted with one or more $R_9$. In yet another embodiment, two $R_8$ together when on adjacent atoms form an heteroaryl ring optionally substituted with one or more $R_9$.

In some embodiments of the Formulae above, $R_9$ is $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, $-(C_0-C_3)$-alkylene-$(C_6-C_{14})$ aryl, $-(C_0-C_3)$-alkylene-heteroaryl, $-NH_2$, $-OH$, $-C(O)R_{23}$, $-C(O)NR_{23}R_{24}$, $-NR_{23}C(O)R_{24}$, $-NR_{23}R_{24}$, $-S(O)_qR_{23}$, $-S(O)_qNR_{23}R_{24}$, $-NR_{23}S(O)_qR_{24}$, OXO, $-P(O)((C_1-C_6)$ alkyl)$_2$, $-P(O)(aryl)_2$, $-SiMe_3$, $-SF_5$, $-O$-aryl, CN, or $-O-$ heteroaryl, wherein the alkyl, aryl, heteroaryl, cycloalkyl, and heterocycloalkyl are optionally substituted with one or more $R_{19}$. In another embodiment, $R_9$ is independently $(C_1-C_6)$ alkyl, $(C_1-C_6)$ alkoxy, $(C_1-C_6)$ haloalkyl, $(C_1-C_6)$ haloalkoxy, halogen, $(C_3-C_8)$ cycloalkyl, heterocycloalkyl, —$(C_0-C_3)$-alkylene-$(C_6-C_{14})$ aryl, —$(C_0-C_3)$-alkylene-heteroaryl, —$NH_2$, —OH, —$C(O)R_{23}$, —$C(O)NR_{23}R_{24}$, —$NR_{23}C(O)R_{24}$, —$NR_{23}R_{24}$, —$S(O)_qR_{23}$, —$S(O)_qNR_{23}R_{24}$, —$NR_{23}S(O)_qR_{24}$, OXO, —$P(O)((C_1-C_6)$ alkyl$)_2$, —$P(O)(aryl)_2$, —$SiMe_3$, —$SF_5$, —O-aryl, CN, or —O-heteroaryl, wherein the alkyl, aryl, heteroaryl, cycloalkyl, and heterocycloalkyl are optionally substituted with one to three $R_{19}$.

In some embodiments of the Formulae above, $R_{10}$ is H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$. In another embodiment, $R_{10}$ is H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one to three $R_{17}$.

In some embodiments of the Formulae above, $R_{11}$ is H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one or more $R_{17}$. In another embodiment, $R_{11}$ is H, $(C_1-C_6)$ alkyl, $(C_6-C_{14})$ aryl, heteroaryl, $(C_5-C_8)$ cycloalkyl, or heterocycloalkyl, wherein the alkyl, aryl, heteroaryl, cycloalkyl, and heterocycloalkyl are optionally substituted with one to three $R_{17}$.

In another embodiment, $R_{10}$ and $R_{11}$ together with the nitrogen to which they are attached form a heterocycloalkyl ring optionally substituted with one or more $R_{17}$. In yet another embodiment, $R_{10}$ and $R_{11}$ together with the nitrogen to which they are attached form a heterocycloalkyl ring optionally substituted with one to three $R_{17}$.

In some embodiments of the Formulae above, $R_{12}$ is $(C_1-C_6)$ alkyl, $(C_1-C_6)$ alkoxy, $(C_1-C_6)$ haloalkyl, $(C_1-C_6)$ haloalkoxy, halogen, CN, —$C(O)(C_1-C_6)$ alkyl, —$S(O)_q(C_1-C_6)$ alkyl, —$NH_2$, $(C_1-C_6)$ alkylamino, or di$(C_1-C_6)$ alkylamino. In another embodiment, $R_{12}$ is $(C_1-C_4)$ alkyl, $(C_1-C_4)$ alkoxy, $(C_1-C_4)$ haloalkyl, $(C_1-C_4)$ haloalkoxy, halogen, CN, —$C(O)(C_1-C_4)$ alkyl, —$S(O)_q(C_1-C_4)$ alkyl, —$NH_2$, $(C_1-C_4)$ alkylamino, or di$(C_1-C_4)$ alkylamino.

In some embodiments of the Formulae above, $R_{13}$ is D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one or more $R_{15}$. In another embodiment, $R_{13}$ is D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one to three $R_{15}$.

In some embodiments of the Formulae above, $R_{14}$ is D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one or more $R_{16}$. In another embodiment, $R_{14}$ is D, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$C(O)(C_1-C_6)$ alkyl, —$S(O)_q(C_1-C_6)$ alkyl, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —$C(O)O(C_1-C_6)$ alkyl, —$C(O)NR_{26}R_{27}$, —$S(O)_qNR_{26}R_{27}$, —$NR_{26}R_{27}$, —$NR_{26}C(O)NR_{26}R_{27}$, —$NR_{26}C(O)OR_{27}$, —$NR_{26}S(O)_qR_{27}$, —$NR_{26}C(O)R_{27}$, halogen, —$P(O)((C_1-C_6)$ alkyl$)_2$, —$P(O)(aryl)_2$, —$SiMe_3$, or —$SF_5$, wherein in the alkyl, aryl, heteroaryl, cycloalkyl, and heterocycloalkyl are optionally substituted with one to three $R_{16}$.

In some embodiments of the Formulae above, $R_{15}$ is $(C_1-C_6)$ alkyl, $(C_1-C_6)$ alkoxy, $(C_1-C_6)$ haloalkyl, $(C_1-C_6)$ haloalkoxy, halogen, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, —OH, or CN. In another embodiment, $R_{15}$ is $(C_1-C_4)$ alkyl, $(C_1-C_4)$ alkoxy, $(C_1-C_4)$ haloalkyl, $(C_1-C_4)$ haloalkoxy, halogen, —$C(O)(C_1-C_4)$ alkyl, —$S(O)_q(C_1-C_4)$ alkyl, —$NH_2$, $(C_1-C_6)$ alkylamino, di$(C_1-C_4)$ alkylamino, —OH, or CN.

In some embodiments of the Formulae above, $R_{16}$ is $(C_1-C_6)$ alkyl, $(C_1-C_6)$ alkoxy, $(C_1-C_6)$ haloalkyl, $(C_1-C_6)$ haloalkoxy, halogen, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —OH, or CN, wherein in the alkyl, aryl, heteroaryl, cycloalkyl, and heterocycloalkyl are optionally substituted with one or more $R_{28}$. In another embodiment, $R_{16}$ is $(C_1-C_4)$ alkyl, $(C_1-C_4)$ alkoxy, $(C_1-C_4)$ haloalkyl, $(C_1-C_4)$ haloalkoxy, halogen, —$C(O)(C_1-C_4)$ alkyl, —$S(O)_q(C_1-C_4)$ alkyl, —$NH_2$, $(C_1-C_6)$ alkylamino, di$(C_1-C_4)$ alkylamino, $(C_6-C_{14})$ aryl, heteroaryl, $(C_3-C_8)$ cycloalkyl, heterocycloalkyl, —O-aryl, —O-heteroaryl, —O-heterocycloalkyl, —O—$(C_3-C_8)$cycloalkyl, —OH, or CN, wherein in the alkyl, aryl, heteroaryl, cycloalkyl, and heterocycloalkyl are optionally substituted with one to three $R_{28}$.

In some embodiments of the Formulae above, $R_{17}$ is $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, $(C_6-C_{14})$ aryl, heteroaryl, $(C_5-C_8)$ cycloalkyl, or heterocycloalkyl, wherein in the alkyl, aryl, heteroaryl, cycloalkyl, and heterocycloalkyl are optionally substituted with one or more $R_{18}$. In another embodiment, $R_{17}$ is $(C_1-C_6)$ alkyl, $(C_1-C_6)$ alkoxy, $(C_1-C_6)$ haloalkyl, $(C_1-C_6)$ haloalkoxy, halogen, $(C_1-C_6)$ hydroxyalkyl, —OH, CN, —$C(O)(C_1-C_6)$ alkyl, —$S(O)_q(C_1-C_6)$ alkyl, —$NH_2$, $(C_1-C_6)$ alkylamino, di$(C_1-C_6)$ alkylamino, ($C_6$-$C_{14}$) aryl, heteroaryl, ($C_5$-$C_8$) cycloalkyl, or heterocycloalkyl, wherein in the alkyl, aryl, heteroaryl, cycloalkyl, and heterocycloalkyl are optionally substituted with one to three $R_{18}$. In yet another embodiment, $R_{17}$ is ($C_1$-$C_4$) alkyl, ($C_1$-$C_4$) alkoxy, ($C_1$-$C_4$) haloalkyl, ($C_1$-$C_4$) haloalkoxy, halogen, ($C_1$-$C_4$) hydroxyalkyl, —OH, CN, —C(O)($C_1$-$C_4$) alkyl, —S(O)$_q$($C_1$-$C_4$) alkyl, —NH$_2$, ($C_1$-$C_4$) alkylamino, di($C_1$-$C_4$) alkylamino, ($C_6$-$C_{14}$) aryl, heteroaryl, ($C_5$-$C_8$) cycloalkyl, or heterocycloalkyl, wherein in the alkyl, aryl, heteroaryl, cycloalkyl, and heterocycloalkyl are optionally substituted with one to three $R_{18}$.

In some embodiments of the Formulae above, $R_{18}$ is ($C_1$-$C_6$) alkyl, ($C_1$-$C_6$) alkoxy, ($C_1$-$C_6$) haloalkyl, ($C_1$-$C_6$) haloalkoxy, halogen, —C(O)($C_1$-$C_6$) alkyl, —S(O)$_q$($C_1$-$C_6$) alkyl, —NH$_2$, ($C_1$-$C_6$) alkylamino, di($C_1$-$C_6$) alkylamino, —OH, or CN. In another embodiment, $R_{18}$ is ($C_1$-$C_4$) alkyl, ($C_1$-$C_4$) alkoxy, ($C_1$-$C_4$) haloalkyl, ($C_1$-$C_4$) haloalkoxy, halogen, —C(O)($C_1$-$C_4$) alkyl, —S(O)$_q$($C_1$-$C_4$) alkyl, —NH$_2$, ($C_1$-$C_4$) alkylamino, di($C_1$-$C_4$) alkylamino, —OH, or CN.

In some embodiments of the Formulae above, $R_{19}$ is ($C_1$-$C_6$) alkyl, ($C_1$-$C_6$) alkoxy, ($C_1$-$C_6$) haloalkyl, ($C_1$-$C_6$) haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)(($C_1$-$C_6$) alkyl)$_2$, —P(O)(aryl)$_2$, —SiMe$_3$, —SF$_5$, —OH, or CN. In another embodiment, $R_{19}$ is ($C_1$-$C_4$) alkyl, ($C_1$-$C_4$) alkoxy, ($C_1$-$C_4$) haloalkyl, ($C_1$-$C_4$) haloalkoxy, halogen, —NR$_{26}$C(O)R$_{27}$, —NR$_{26}$S(O)$_q$R$_{27}$, —C(O)R$_{26}$, —C(O)NR$_{26}$R$_{27}$, —NR$_{26}$R$_{27}$, —S(O)$_q$R$_{26}$, —S(O)$_q$NR$_{26}$R$_{27}$, —P(O)(($C_1$-$C_6$) alkyl)$_2$, —P(O)(aryl)$_2$, —SiMe$_3$, —SF$_5$, —OH, or CN.

In some embodiments of the Formulae above, $R_{20}$ is ($C_1$-$C_6$) alkyl, ($C_1$-$C_6$) alkoxy, ($C_1$-$C_6$) haloalkyl, ($C_1$-$C_6$) haloalkoxy, halogen, —OH, —NH$_2$, or CN. In another embodiment, $R_{20}$ is ($C_1$-$C_4$) alkyl, ($C_1$-$C_4$) alkoxy, ($C_1$-$C_4$) haloalkyl, ($C_1$-$C_4$) haloalkoxy, halogen, —OH, —NH$_2$, or CN.

In some embodiments of the Formulae above, $R_{21}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one or more $R_{25}$. In another embodiment, $R_{21}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one to three $R_{25}$.

In some embodiments of the Formulae above, $R_{22}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one or more $R_{25}$. In another embodiment, $R_{22}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one to three $R_{25}$.

In some embodiments of the Formulae above, $R_{23}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one or more $R_{25}$. In another embodiment, $R_{23}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one to three $R_{25}$.

In some embodiments of the Formulae above, $R_{24}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one or more $R_{25}$. In another embodiment, $R_{24}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, aryl, heteroaryl, cycloalkyl and heterocycloalkyl are optionally substituted with one to three $R_{25}$.

In some embodiments of the Formulae above, $R_{25}$ is ($C_1$-$C_6$) alkyl, ($C_1$-$C_6$) alkoxy, ($C_1$-$C_6$) haloalkyl, ($C_1$-$C_6$) haloalkoxy, halogen, —OH, or CN. In another embodiment, $R_{25}$ is ($C_1$-$C_4$) alkyl, ($C_1$-$C_4$) alkoxy, ($C_1$-$C_4$) haloalkyl, ($C_1$-$C_4$) haloalkoxy, halogen, —OH, or CN.

In some embodiments of the Formulae above, $R_{26}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, alkenyl, alkynyl, aryl, heteroaryl, cycloalkyl and heterocycloalkyl are optionally substituted with one or more substituents independently selected from ($C_1$-$C_6$) alkyl, ($C_1$-$C_6$) alkoxy, ($C_1$-$C_6$) haloalkyl, ($C_1$-$C_6$) haloalkoxy, —NH$_2$, ($C_1$-$C_6$) alkylamino, or di($C_1$-$C_6$) alkylamino. In another embodiment, $R_{26}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, alkenyl, alkynyl, aryl, heteroaryl, cycloalkyl and heterocycloalkyl are optionally substituted with one to three substituents independently selected from ($C_1$-$C_6$) alkyl, ($C_1$-$C_6$) alkoxy, ($C_1$-$C_6$) haloalkyl, ($C_1$-$C_6$) haloalkoxy, —NH$_2$, ($C_1$-$C_6$) alkylamino, or di($C_1$-$C_6$) alkylamino.

In some embodiments of the Formulae above, $R_{27}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, alkenyl, alkynyl, aryl, heteroaryl, cycloalkyl and heterocycloalkyl are optionally substituted with one or more substituents independently selected from ($C_1$-$C_6$) alkyl, ($C_1$-$C_6$) alkoxy, ($C_1$-$C_6$) haloalkyl, ($C_1$-$C_6$) haloalkoxy, —NH$_2$, ($C_1$-$C_6$) alkylamino, or di($C_1$-$C_6$) alkylamino. In another embodiment, $R_{27}$ is H, ($C_1$-$C_6$) alkyl, ($C_2$-$C_6$) alkenyl, ($C_2$-$C_6$) alkynyl, ($C_6$-$C_{14}$) aryl, heteroaryl, ($C_5$-$C_8$) cycloalkyl, or heterocycloalkyl, wherein the alkyl, alkenyl, alkynyl, aryl, heteroaryl, cycloalkyl and heterocycloalkyl are optionally substituted with one to three substituents independently selected from ($C_1$-$C_6$) alkyl, ($C_1$-$C_6$) alkoxy, ($C_1$-$C_6$) haloalkyl, ($C_1$-$C_6$) haloalkoxy, —NH$_2$, ($C_1$-$C_6$) alkylamino, or di($C_1$-$C_6$) alkylamino.

In some of the embodiments of the Formulae above, $R_{28}$ is ($C_1$-$C_6$) alkyl, ($C_1$-$C_6$) alkoxy, ($C_1$-$C_6$) haloalkyl, ($C_1$-$C_6$) haloalkoxy, halogen, —C(O)($C_1$-$C_6$) alkyl, —S(O)$_q$($C_1$-$C_6$) alkyl, —NH$_2$, ($C_1$-$C_6$) alkylamino, di($C_1$-$C_6$) alkylamino, —OH, or CN. In another embodiment, $R_{28}$ is ($C_1$-$C_4$) alkyl, ($C_1$-$C_4$) alkoxy, ($C_1$-$C_4$) haloalkyl, ($C_1$-$C_4$) haloalkoxy, halogen, —C(O)($C_1$-$C_4$) alkyl, —S(O)$_q$($C_1$-$C_4$) alkyl, —NH$_2$, ($C_1$-$C_4$) alkylamino, di($C_1$-$C_4$) alkylamino, —OH, or CN.

In some embodiments of the Formulae above, m is 0, 1, 2, 3, or 4. In another embodiment, m is 0, 1, 2, or 3. In yet another embodiment, m is 0, 1, or 2. In another embodiment, m is 0 or 1. In yet another embodiment, m is 0. In another embodiment, m is 1. In yet another embodiment, m is 2. In yet another embodiment, m is 3. In yet another embodiment, m is 4.

In some embodiments of the Formulae above, n is 0, 1, 2, or 3. In another embodiment, n is 0, 1, or 2. In yet another embodiment, n is 0 or 1. In another embodiment, n is 0. In yet another embodiment, n is 1. In another embodiment, n is 2. In yet another embodiment, n is 3.

In some embodiments of the Formulae above, q is 0, 1, or 2. In another embodiment, q is 0. In yet another embodiment, q is 1. In another embodiment, q is 2.

In some embodiments of the Formulae above, $X_1$ is C.

In some embodiments of the Formulae above, $R_1$ is —OH.

In some embodiments of the Formulae above, $R_2$ is $(C_1$-$C_6)$ alkyl or $(C_6$-$C_{14})$ aryl, wherein the alkyl and aryl are optionally substituted with one or more $R_8$.

In some embodiments of the Formulae above, $R_4$ is H.

In some embodiments of the Formulae above, $R_{4'}$ is H.

In some embodiments of the Formulae above, $Y_2$ is N or $CR_5$ and $R_5$ is H.

In some embodiments of the Formulae above, $Y_3$ is N or $CR_6$ and $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$.

In some embodiments of the Formulae above, $Y_4$ is N or $CR_7$ and $R_7$ is H, $(C_1$-$C_6)$ alkyl, $(C_6$-$C_{14})$ aryl, or —O-aryl, wherein the alkyl and aryl are optionally substituted with one or more $R_{14}$.

In some embodiments of the Formulae above, n is 1.

In some embodiments of the Formulae above, $R_5$, $R_6$, and $R_7$ are not all simultaneously H.

In some embodiments of the Formulae above, $R_2$ is optionally substituted alkyl, $R_5$ is H, $R_7$ is H, and $R_6$ is not chloro.

In some embodiments of the Formulae above, $X_1$ is C. In another embodiment, $X_1$ is C and $Y_1$ is CH. In yet another embodiment, $X_1$ is C, $Y_1$ is CH, and $Y_2$ is $CR_5$. In another embodiment, $X_1$ is C, $Y_1$ is CH, $Y_2$ is $CR_5$, and $Y_3$ is $CR_6$. In another embodiment, $X_1$ is C, $Y_1$ is CH, $Y_2$ is $CR_5$, $Y_3$ is $CR_6$, and $Y_4$ is $CR_7$. In yet another embodiment, $X_1$ is C, $Y_1$ is CH, $Y_2$ is CRS, $Y_3$ is $CR_6$, $Y_4$ is $CR_7$, and $R_1$ is OH. In another embodiment, $X_1$ is C, $Y_1$ is CH, $Y_2$ is $CR_5$, $Y_3$ is $CR_6$, $Y_4$ is $CR_7$, $R_1$ is OH, and $R_2$ is $(C_1$-$C_6)$ alkyl or $(C_6$-$C_{14})$ aryl, wherein the alkyl and aryl are optionally substituted with one or more $R_8$. In yet another embodiment, $X_1$ is C, $Y_1$ is CH, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, and $R_4$ is H. In another embodiment, $X_1$ is C, $Y_1$ is CH, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, and $R_{4'}$ is H. In another embodiment, $X_1$ is C, $Y_1$ is CH, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, and $R_5$ is H. In yet another embodiment, $X_1$ is C, $Y_1$ is CH, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, $R_5$ is H, and $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$. In another embodiment, $X_1$ is C, $Y_1$ is CH, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, $R_5$ is H, $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$, and $R_7$ is H, $(C_1$-$C_6)$ alkyl, $(C_6$-$C_{14})$ aryl, or —O-aryl, wherein the alkyl and aryl are optionally substituted with one or more $R_{14}$.

In some embodiments of the Formulae above, $X_1$ is C. In another embodiment, $X_1$ is C and $Y_1$ is N. In yet another embodiment, $X_1$ is C, $Y_1$ is N, and $Y_2$ is $CR_5$. In another embodiment, $X_1$ is C, $Y_1$ is N, $Y_2$ is $CR_5$, and $Y_3$ is $CR_6$. In another embodiment, $X_1$ is C, $Y_1$ is N, $Y_2$ is $CR_5$, $Y_3$ is $CR_6$, and $Y_4$ is $CR_7$. In yet another embodiment, $X_1$ is C, $Y_1$ is N, $Y_2$ is $CR_5$, $Y_3$ is $CR_6$, $Y_4$ is $CR_7$, and $R_1$ is OH. In another embodiment, $X_1$ is C, $Y_1$ is N, $Y_2$ is $CR_5$, $Y_3$ is $CR_6$, $Y_4$ is $CR_7$, $R_1$ is OH, and $R_2$ is $(C_1$-$C_6)$ alkyl or $(C_6$-$C_{14})$ aryl, wherein the alkyl and aryl are optionally substituted with one or more $R_8$. In yet another embodiment, $X_1$ is C, $Y_1$ is N, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, and $R_4$ is H. In another embodiment, $X_1$ is C, $Y_1$ is N, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, and $R_{4'}$ is H. In yet another embodiment, $X_1$ is C, $Y_1$ is N, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, and $R_5$ is H. In another embodiment, $X_1$ is C, $Y_1$ is N, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, $R_5$ is H, and $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$. In yet another embodiment, $X_1$ is C, $Y_1$ is N, $Y_2$ is $CR_5$, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, $R_5$ is H, $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$, and $R_7$ is H, $(C_1$-$C_6)$ alkyl, $(C_6$-$C_{14})$ aryl, or —O-aryl, wherein the alkyl and aryl are optionally substituted with one or more $R_{14}$.

In some embodiments of the Formulae above, $X_1$ is C. In another embodiment, $X_1$ is C and $Y_1$ is CH. In yet another embodiment, $X_1$ is C, $Y_1$ is CH, and $Y_2$ is N. In another embodiment, $X_1$ is C, $Y_1$ is CH, $Y_2$ is N, and $Y_3$ is $CR_6$. In yet another embodiment, $X_1$ is C, $Y_1$ is CH, $Y_2$ is N, $Y_3$ is $CR_6$, and $Y_4$ is $CR_7$. In another embodiment, $X_1$ is C, $Y_1$ is CH, $Y_2$ is N, $Y_3$ is $CR_6$, $Y_4$ is $CR_7$, and $R_1$ is OH. In yet another embodiment, $X_1$ is C, $Y_1$ is CH, $Y_2$ is N, $Y_3$ is $CR_6$, $Y_4$ is $CR_7$, $R_1$ is OH, and $R_2$ is $(C_1$-$C_6)$ alkyl or $(C_6$-$C_{14})$ aryl, wherein the alkyl and aryl are optionally substituted with one or more $R_8$. In another embodiment, $X_1$ is C, $Y_1$ is CH, $Y_2$ is N, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, and $R_4$ is H. In yet another embodiment, $X_1$ is C, $Y_1$ is CH, $Y_2$ is N, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, and $R_{4'}$ is H. In yet another embodiment, $X_1$ is C, $Y_1$ is CH, $Y_2$ is N, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, and $R_6$ is H, $(C_1$-$C_6)$ alkyl, $(C_1$-$C_6)$ alkoxy, —$NH_2$, —$NHC(O)(C_1$-$C_6)$ alkyl, or $(C_6$-$C_{14})$ aryl, wherein the alkyl, and aryl are optionally substituted with one or more $R_{13}$. In another embodiment, $X_1$ is C, $Y_1$ is CH, $Y_2$ is N, $Y_3$ is $CR_6$, $Y_4$ is $CR_7$, $R_1$ is OH, $R_2$ is $(C_1$-$C_6)$ alkyl or $(C_6$-$C_{14})$ aryl, wherein the alkyl and aryl are optionally substituted with one or more $R_8$, $R_4$ is H, $R_{4'}$ is H, $R_6$ is H, ($C_1$-$C_6$) alkyl, ($C_1$-$C_6$) alkoxy, —$NH_2$, —NHC(O)($C_1$-$C_6$) alkyl, or ($C_6$-$C_{14}$) aryl, wherein the alkyl, and aryl are optionally substituted with one or more $R_{13}$, and $R_7$ is H, ($C_1$-$C_6$) alkyl, ($C_6$-$C_{14}$) aryl, or —O-aryl, wherein the alkyl and aryl are optionally substituted with one or more $R_{14}$.

In some embodiments of the Formulae above, $X_1$ is C. In another embodiment, $X_1$ is C and $Y_1$ is CH. In yet another embodiment, $X_1$ is C, $Y_1$ is CH, and $Y_2$ is $CR_5$. In another embodiment, $X_1$ is C, $Y_1$ is CH, $Y_2$ is $CR_5$, and $Y_3$ is N. In yet another embodiment, $X_1$ is C, $Y_1$ is CH, $Y_2$ is $CR_5$, $Y_3$ is N, and $Y_4$ is $CR_7$. In another embodiment, $X_1$ is C, $Y_1$ is CH, $Y_2$ is $CR_5$, $Y_3$ is N, $Y_4$ is $CR_7$, and $R_1$ is OH. In yet another embodiment, $X_1$ is C, $Y_1$ is CH, $Y_2$ is $CR_5$, $Y_3$ is N, $Y_4$ is $CR_7$, $R_1$ is OH, and $R_2$ is ($C_1$-$C_6$) alkyl or ($C_6$-$C_{14}$) aryl, wherein the alkyl and aryl are optionally substituted with one or more $R_8$. In another embodiment, $X_1$ is C, $Y_1$ is CH, $Y_2$ is CRS, $Y_3$ is N, $Y_4$ is $CR_7$, $R_1$ is OH, $R_2$ is ($C_1$-$C_6$) alkyl or ($C_6$-$C_{14}$) aryl, wherein the alkyl and aryl are optionally substituted with one or more $R_8$, and $R_4$ is H. In yet another embodiment, $X_1$ is C, $Y_1$ is CH, $Y_2$ is $CR_5$, $Y_3$ is N, $Y_4$ is $CR_7$, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, and $R_{4'}$ is H. In another embodiment, $X_1$ is C, $Y_1$ is CH, $Y_2$ is $CR_5$, $Y_3$ is N, $Y_4$ is $CR_7$, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, $R_{4'}$ is H, and $R_5$ is H. In yet another embodiment, $X_1$ is C, $Y_1$ is CH, $Y_2$ is $CR_5$, $Y_3$ is N, $Y_4$ is $CR_7$, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, $R_{4'}$ is H, $R_5$ is H, and $R_7$ is H, ($C_1$-$C_6$) alkyl, ($C_6$-$C_{14}$) aryl, or —O-aryl, wherein the alkyl and aryl are optionally substituted with one or more $R_{14}$.

In some embodiments of the Formulae above, $X_1$ is C. In another embodiment, $X_1$ is C and $Y_1$ is CH. In yet another embodiment, $X_1$ is C, $Y_1$ is CH, and $Y_2$ is $CR_5$. In another embodiment, $X_1$ is C, $Y_1$ is CH, $Y_2$ is $CR_5$, and $Y_3$ is $CR_6$. In yet another embodiment, $X_1$ is C, $Y_1$ is CH, $Y_2$ is $CR_5$, $Y_3$ is $CR_6$, and $Y_4$ is N. In another embodiment, $X_1$ is C, $Y_1$ is CH, $Y_2$ is $CR_5$, $Y_3$ is $CR_6$, $Y_4$ is N, and $R_1$ is OH. In yet another embodiment, $X_1$ is C, $Y_1$ is CH, $Y_2$ is $CR_5$, $Y_3$ is $CR_6$, $Y_4$ is N, $R_1$ is OH, and $R_2$ is ($C_1$-$C_6$) alkyl or ($C_6$-$C_{14}$) aryl, wherein the alkyl and aryl are optionally substituted with one or more $R_8$. In another embodiment, $X_1$ is C, $Y_1$ is CH, $Y_2$ is $CR_5$, $Y_3$ is $CR_6$, $Y_4$ is N, $R_1$ is OH, $R_2$ is ($C_1$-$C_6$) alkyl or ($C_6$-$C_{14}$) aryl, wherein the alkyl and aryl are optionally substituted with one or more $R_8$, and $R_4$ is H. In yet another embodiment, $X_1$ is C, $Y_1$ is CH, $Y_2$ is $CR_5$, $Y_3$ is $CR_6$, $Y_4$ is N, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, and $R_{4'}$ is H. In another embodiment, $X_1$ is C, $Y_1$ is CH, $Y_2$ is $CR_5$, $Y_3$ is $CR_6$, $Y_4$ is N, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, $R_{4'}$ is H, and $R_5$ is H. In yet another embodiment, $X_1$ is C, $Y_1$ is CH, $Y_2$ is $CR_5$, $Y_3$ is $CR_6$, $Y_4$ is N, $R_1$ is OH, $R_2$ is ($C_1$-$C_6$) alkyl or ($C_6$-$C_{14}$) aryl, wherein the alkyl and aryl are optionally substituted with one or more $R_8$, $R_4$ is H, $R_{4'}$ is H, $R_5$ is H, and $R_6$ is H, ($C_1$-$C_6$) alkyl, ($C_1$-$C_6$) alkoxy, —$NH_2$, —NHC(O)($C_1$-$C_6$) alkyl, or ($C_6$-$C_{14}$) aryl, wherein the alkyl, and aryl are optionally substituted with one or more $R_{13}$.

Non-limiting illustrative compounds of the disclosure include:
3-((4-hydroxy-1-(3-phenylbutanoyl)piperidin-4-yl)methyl)-7-methoxyquinazolin-4(3H)-one (I-1);
3-((4-hydroxy-1-(3-phenylbutanoyl)piperidin-4-yl)methyl)-8-methylquinazolin-4(3H)-one (I-2);
7-amino-3-((4-hydroxy-1-(3-phenylbutanoyl)piperidin-4-yl)methyl)quinazolin-4(3H)-one (I-3);
N-(3-((4-hydroxy-1-(3-phenylbutanoyl)piperidin-4-yl)methyl)-4-oxo-3,4-dihydroquinazolin-7-yl)acetamide (I-4);
(R)-3-((4-hydroxy-1-(3-phenylbutanoyl)piperidin-4-yl)methyl)-7-methoxyquinazolin-4(3H)-one (I-5);
(R)-3-((4-hydroxy-1-(3-phenylbutanoyl)piperidin-4-yl)methyl)-8-methylquinazolin-4(3H)-one (I-6);
3-((1-(1-benzylindoline-5-carbonyl)-4-hydroxypiperidin-4-yl)methyl)-7-methoxyquinazolin-4(3H)-one (I-7);
3-((1-benzoyl-4-hydroxypiperidin-4-yl)methyl)-7-phenylquinazolin-4(3H)-one (I-8);
3-((1-benzoyl-4-hydroxypiperidin-4-yl)methyl)-8-phenylquinazolin-4(3H)-one (I-9);
3-((1-(4-fluorobenzoyl)-4-hydroxypiperidin-4-yl)methyl)-8-(4-fluorophenoxy)quinazolin-4(3H)-one (I-10);
3-((4-hydroxy-1-(3-phenylbutanoyl)piperidin-4-yl)methyl)pyrido[2,3-d]pyrimidin-4(3H)-one (I-11);
3-((4-hydroxy-1-(3-phenylbutanoyl)piperidin-4-yl)methyl)pyrido[3,4-d]pyrimidin-4(3H)-one (I-12); and
3-((4-hydroxy-1-(3-phenylbutanoyl)piperidin-4-yl)methyl)pyrido[3,2-d]pyrimidin-4(3H)-one (I-13).

In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this disclosure. Reference to a compound of the Formula herein is understood to include reference to salts thereof, unless otherwise indicated.

The present disclosure relates to compounds which are modulators of USP7. In one embodiment, the compounds of the present disclosure are inhibitors of USP7.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below. Compounds of the present disclosure can be synthesized by following the steps outlined in General Schemes 1 and 2 which comprise different sequences of assembling intermediates Ia-Ih. Starting materials are either commercially available or made by known procedures in the reported literature or as illustrated.

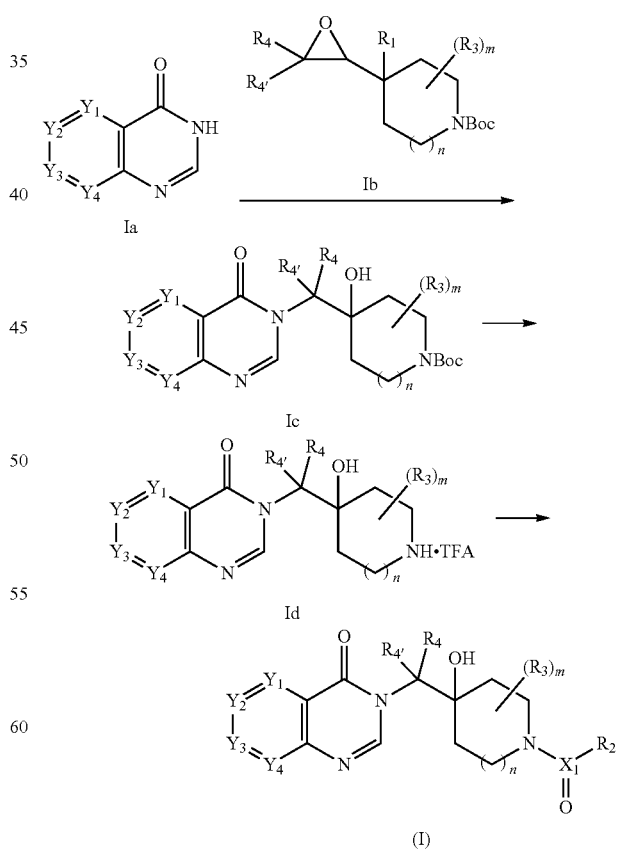

General Scheme 1 wherein $R_2$—$R_4$, $R_{4'}$, $X_1$, $Y_1$, $Y_2$, $Y_3$, $Y_4$, m, and n are defined as in Formula (I).

The general way of preparing compounds of Formula (I) by using intermediates Ia, Ib, Ic, and Id is outlined in General Scheme 1. Alkylation of Ia with Ib using a base, e.g., cesium carbonate, in a solvent, e.g., dimethylformamide (DMF), at elevated temperature yields Ic. Deprotection of intermediate Ic using a strong acid such as trifluoroacetic acid (TFA) in a solvent, e.g., 1,2,-dichloroethane or dichloromethane (DCM) optionally at elevated temperature yields Id. Acylation of intermediate Id to produce a compound of Formula (I) where $X_1$ is C can be accomplished by coupling of an acid under standard coupling conditions using a coupling reagent, e.g., 2-(7-Aza-1H-benzotriazole-1-yl)-1,1,3,3-tetramethyluronium hexafluorophosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF to provide compounds of Formula (I). Alternatively, intermediate Id can be acylated with an acid chloride or carbamoyl chloride using a base, e.g., triethylamine or DIPEA, and in a solvent, e.g., dichloromethane, to produce a compound of Formula (I) where $X_1$ is C. For synthesis of compounds of Formula (I) where $X_1$ is S or S(O), intermediate Id is treated with a sulfonyl chloride or a sulfinic chloride and a base, e.g., triethylamine or N,N-diisopropylethylamine (DIPEA), in a solvent, e.g., dichloromethane, DMF to provide the desired product of Formula (I).

General Scheme 2

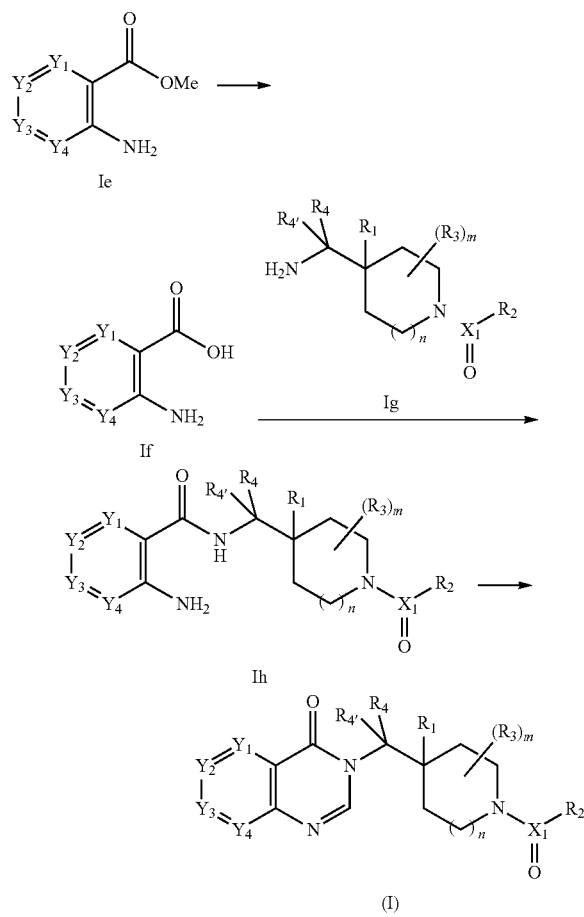

wherein $R_1$—$R_4$, $R_{4'}$, $X_1$, $Y_1$, $Y_2$, $Y_3$, $Y_4$, m, and n are defined as in Formula (I).

Alternatively, molecules of Formula I can be prepared using intermediates Ie, If, Ig, and Ih as outlined in General Scheme 2. Hydrolysis of intermediate Ie with lithium hydroxide in solvent, e.g., methanol and/or water, provides intermediate If. Coupling of If with Ig using a coupling reagent, e.g., 2-(7-Aza-1H-benzotriazole-1-yl)-1,1,3,3-tetramethyluronium hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Ih. Cyclization of Ih with trimethyl orthoformate at elevated temperature provides the desired product of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R_1$—$R_4$, $R_{4'}$, $X_1$, $Y_1$, $Y_2$, $Y_3$, $Y_4$, m, n, and other variables are as defined above, except where otherwise indicated. Furthermore, for synthetic purposes, the compounds of General Schemes 1 and 2 are mere representative with elected radicals to illustrate the general synthetic methodology of the compounds of Formula (I) as defined herein.

Methods of Using the Disclosed Compounds

Another aspect of the disclosure relates to a method of treating a disease or disorder associated with modulation of USP7. The method comprises administering to a patient in need of a treatment for diseases or disorders associated with modulation of USP7 an effective amount the compositions and compounds of Formula (I).

In another aspect, the present disclosure is directed to a method of inhibiting USP7. The method involves administering to a patient in need thereof an effective amount of a compound of Formula (I).

Another aspect of the present disclosure relates to a method of treating, preventing, inhibiting or eliminating a disease or disorder in a patient associated with the inhibition of USP7, the method comprising administering to a patient in need thereof an effective amount of a compound of Formula (I). In one embodiment, the disease or disorder is selected from the group consisting of cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present disclosure also relates to the use of an inhibitor of USP7 for the preparation of a medicament used in the treatment, prevention, inhibition or elimination of a disease or condition mediated by USP7, wherein the medicament comprises a compound of Formula (I).

In another aspect, the present disclosure relates to a method for the manufacture of a medicament for treating, preventing, inhibiting, or eliminating a disease or condition mediated by USP7, wherein the medicament comprises a compound of Formula (I).

Another aspect of the present disclosure relates to a compound of Formula (I) for use in the manufacture of a medicament for treating a disease associated with inhibiting USP7.

In another aspect, the present disclosure relates to the use of a compound of Formula (I) in the treatment of a disease associated with inhibiting USP7.

Another aspect of the disclosure relates to a method of treating cancer. The method comprises administering to a patient in need thereof an effective amount of a compound of Formula (I).

In another aspect, the present disclosure relates to a method of treating a neurodegenerative disease. The method comprises administering to a patient in need thereof an effective amount of a compound of Formula (I).

Another aspect of the disclosure relates to a method of treating a viral infection and disease. The method comprises administering to a patient in need thereof an effective amount of a compound of Formula (I).

In another aspect, the present disclosure relates to a method of treating an inflammatory disease or condition. The method comprises administering to a patient in need thereof an effective amount of a compound of Formula (I).

Another aspect of the disclosure relates to a method of inducing cell cycle arrest, apoptosis in tumor cells, and/or enhanced tumor-specific T cell immunity. The method comprises contacting the cells with an effective amount of a compound of Formula (I).

In one embodiment, the present disclosure relates to the use of an inhibitor of USP7 for the preparation of a medicament used in treatment, prevention, inhibition or elimination of a disease or disorder associated with associated with cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

In another embodiment, the present disclosure relates to a compound of Formula (I) or a pharmaceutical composition comprising a compound of the present disclosure and a pharmaceutically acceptable carrier used for the treatment of cancers including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid or vaginal cancer or Epstein-Barr Virus-associated nasopharyngeal carcinoma, gastric cancer, rectal cancer, thyroid cancer, Hodgkin lymphoma or diffuse large B-cell lymphoma.

In some embodiments, the patient is selected for treatment based on gene amplification and/or elevated tumor expression of USP7, MDM2 or MDM4 relative to tissue-matched expression. In other embodiments, the patient is selected for the treatment based on tumor expression of wild type TP53 or based on the tumor immune cell composition, specifically elevated regulatory T lymphocytes, CD4+CD25+FoxP3+ T cells.

In some embodiments, administration of a compound of Formula (I) or a pharmaceutical composition comprising a compound of the present disclosure and a pharmaceutically acceptable carrier induces a change in the cell cycle or cell viability.

For example, the change in the cell cycle or cell viability may be indicated by decreased tumor levels of MDM2 protein and/or increased levels of TP53, CDKN1A (p21, Cip1), PUMA or BAX or by increased expression of one or more p53 target genes. In one embodiment, the p53 target genes include, but are not limited to, CDKN1A (p21, Cip1), BBC3 (PUMA), BAX or MDM2.

In another embodiment, the present disclosure relates to a compound of Formula (I) or a pharmaceutical composition comprising a compound of the present disclosure and a pharmaceutically acceptable carrier used for the treatment of neurodegenerative diseases including, but not limited to, Alzheimer's disease, multiple sclerosis, Huntington's disease, infectious meningitis, encephalomyelitis, Parkinson's disease, amyotrophic lateral sclerosis, or encephalitis.

Another embodiment of the present disclosure relates to a compound of Formula (I) or a pharmaceutical composition comprising a compound of the present disclosure and a pharmaceutically acceptable carrier used for the treatment of viral infections and diseases including but not limited to, herpes simplex-1 or -2 viral infections, hepatitis A, hepatitis C, SARS coronavirus infection and disease, Epstein-Barr virus, rhinoviral infections and diseases, adenoviral infections and diseases, or poliomyelitis.

In another embodiment, the present disclosure relates to a compound of Formula (I) or a pharmaceutical composition comprising a compound of the present disclosure and a pharmaceutically acceptable carrier used for the treatment of inflammatory diseases or conditions is associated with metabolic disorders including, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, or macular edema.

In another embodiment, the present disclosure relates to a compound of Formula (I) or a pharmaceutical composition comprising a compound of the present disclosure and a pharmaceutically acceptable carrier used for the treatment of inflammatory diseases or conditions is associated with inflammatory bowel diseases including, but not limited to, ileitis, ulcerative colitis, Barrett's syndrome, or Crohn's disease Another aspect of the disclosure is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of USP7 including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I).

One therapeutic use of the compounds or compositions of the present disclosure which inhibit USP7 is to provide treatment to patients or subjects suffering from cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The disclosed compounds of the disclosure can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.
Analytical Methods, Materials, and Instrumentation Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm ($\delta$) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 µm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted on a Waters SunFire C18 OBD Prep Column, 100 Å, 5 µm, 19 mm×50 mm, Waters XBridge BEH C18 OBD Prep Column, 130 Å, 5 µm, 19 mm×50 mm with UV detection (Waters 2489 UV/998 PDA), Waters SunFire C18 OBD Prep Column, 100 Å, 5 µm, 19 mm×150 mm, Waters XBridge BEH Shield RP18 OBD Prep Column, 130 Å, 5 µm, 19 mm×150 mm, or Waters XSelect CSH C18 OBD Prep Column, 130 Å, 5 µm, 19 mm×150 mm at 254 nm or 220 nm using a standard solvent gradient program (or as designated below).

Abbreviations used in the following examples and elsewhere herein are:

atm atmosphere
br broad
BINAP (2,2'-bis(diphenylphosphino)-1,1'-binaphthyl)
DABCO 1,4-diazabicyclo[2.2.2]octane
DAST diethylaminosulfur trifluoride
DBU 2,3,4,6,7,8,9,10-octahydropyrimido[1,2-a]azepine
DIPEA N,N-diisopropylethylamine
DMA N,N-dimethylacetamide
DMF N,N-dimethylformamide
DMSO dimethyl sulfoxide
dppf 1,1'-bis(diphenylphosphino)ferrocene
EDC N-(3-Dimethylaminopropyl)-N'-ethylcarbodiimide hydrochloride
EI electron ionization
ESI electrospray ionization
Et ethyl
GCMS gas chromatography-mass spectrometry
h hour(s)
HATU 2-(7-Aza-1H-benzotriazole-1-yl)-1,1,3,3-tetramethyluronium hexafluorophosphate
HPLC high-performance liquid chromatography
LCMS liquid chromatography-mass spectrometry
m multiplet
Me methyl
MHz megahertz
min minutes
MS molecular sieves
MTBE 2-methoxy-2-methylpropane
MW microwave
NMR nuclear magnetic resonance
ppm parts per million
RuPhos 2-dicyclohexylphosphino-2',6'-diisopropoxybiphenyl
s singlet
TFA trifluoroacetic acid
TLC thin layer chromatography
v volume
wt weight Example 1: Intermediate 2-1. 3-((4-Hydroxy-1-(3-phenylbutanoyl)piperidin-4-yl) methyl)-7-nitroquinazolin-4(3H)-one

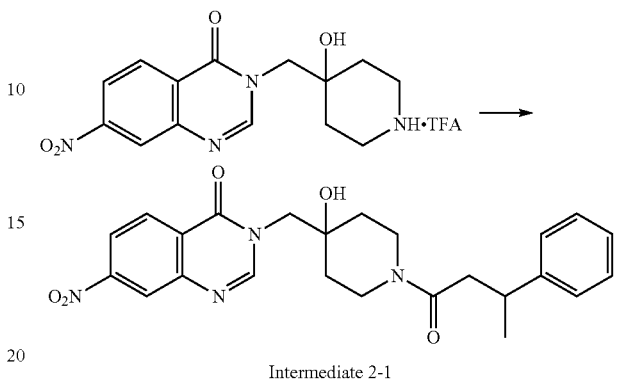

Intermediate 2-1

3-((4-Hydroxy-1-(3-phenylbutanoyl)piperidin-4-yl) methyl)-7-nitroquinazolin-4(3H)-one (Intermediate 2-1, 88 mg, 39%) was prepared from 7-nitroquinazolin-4(3H)-one (prepared using Method A below, Example 5) and purified by column chromatography eluting with 50 to 100% ethyl acetate/hexanes. LCMS (ESI) m/z 451.22 [M+H].

Example 2: Intermediate 2-2. 7-Phenylquinazolin-4(3H)-one

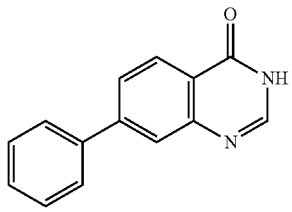

Intermediate 2-2

7-Bromoquinazolin-4(3H)-one (1.60 g, 7.12 mmol), phenylboronic acid (1.04 g, 8.56 mmol), [1,1'-bis(diphenylphosphino)ferrocene]dichloropalladium(II), complex with dichloromethane (696 mg, 0.852 mmol), sodium carbonate (1.49 g, 14.1 mmol), 1,4-dioxane (150 mL) and water (30 mL) were added to a 250-mL 3-necked round-bottom flask fitted with a nitrogen inlet, magnetic stir bar and thermometer. The resulting solution was stirred for 3 h at 100° C., then cooled to room temperature, filtered and diluted with water (100 mL). The mixture was extracted with ethyl acetate (3×100 mL) and the organic layers were combined, dried over anhydrous sodium sulfate, filtered and concentrated under reduced pressure. The residue was purified by column chromatography eluting with dichloromethane/methanol (20:1 v/v) to afford 7-phenylquinazolin-4(3H)-one (Intermediate 2-2, 600 mg, 38%). LCMS (ESI) m/z 223 [M+H].

Example 3: Intermediate 2-3. 8-Phenylquinazolin-4(3H)-one

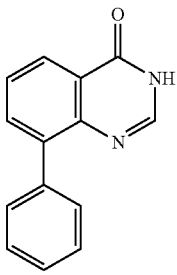

Intermediate 2-3

8-Phenylquinazolin-4(3H)-one (Intermediate 2-3, 700 mg, 28%) was prepared from 8-bromoquinazolin-4(3H)-one according to the procedure used for Intermediate 2-2 (Example 2), and was purified by column chromatography eluting with dichloromethane/methanol (10:1 v/v). LCMS (ESI) m/z 223 [M+H].

Example 4: Intermediate 2-4. (4-(Aminomethyl)-4-hydroxypiperidin-1-yl)(4-fluorophenyl) methanone

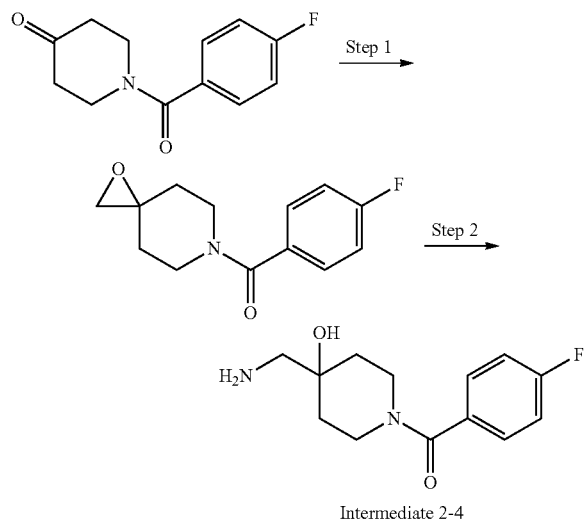

Intermediate 2-4

Step 1. (4-Fluorophenyl)(1-oxa-6-azaspiro[2.5]octan-6-yl)methanone

Trimethylsulfoxonium iodide (2.60 g, 11.8 mmol), sodium hydride (60% in mineral oil, 480 mg, 12.0 mmol) and dimethyl sulfoxide (15 mL) were added to a 100-mL round-bottom flask fitted with a nitrogen inlet and magnetic stir bar. The resulting mixture was stirred for 30 min at room temperature. 1-(4-Fluorobenzoyl)piperidin-4-one (2.00 g, 9.04 mmol) was added and stirring was continued for an additional 4 h at room temperature. The reaction was quenched by the addition of water (30 mL) and extracted with dichloromethane (3×30 mL). The organic layers were combined, dried over anhydrous sodium sulfate, filtered and concentrated under reduced pressure. The residue was purified by column chromatography eluting with ethyl acetate to afford (4-fluorophenyl)(1-oxa-6-azaspiro[2.5]octan-6-yl)methanone (0.75 g, 40%). LCMS: (ESI) m/z 236 [M+H].

Step 2. (4-(Aminomethyl)-4-hydroxypiperidin-1-yl)(4-fluorophenyl)methanone

Ammonia (7.0 M in methanol, 15 mL, 0.105 mol) and (4-fluorophenyl)(1-oxa-6-azaspiro[2.5]octan-6-yl)methanone (Step 1, 350 mg, 1.49 mmol) were added to a 100-mL round-bottom flask fitted with a magnetic stir bar. The resulting solution was stirred for 3 h at 60° C., then cooled to room temperature and concentrated under reduced pressure. The residue was purified by column chromatography eluting with ethyl acetate/petroleum ether (1:2 v/v) to afford (4-(aminomethyl)-4-hydroxypiperidin-1-yl)(4-fluorophenyl)methanone (Intermediate 2-4, 0.28 g, 73%). LCMS: (ESI) m/z 253 [M+H]. $^1$H NMR (400 MHz, DMSO-d$^6$) δ 7.47-7.43 (m, 2H), 7.29-7.24 (m, 2H), 4.95 (s, 1H), 3.16-2.96 (m, 2H), 2.54-2.52 (m, 2H), 2.25-1.70 (m, 1H), 1.65-1.15 (m, 4H) ppm.

Methods for the Synthesis of Compounds of Formula (I)

Method A

Example 5: 3-((4-Hydroxy-1-(3-phenylbutanoyl)piperidin-4-yl)methyl)-8-methylquinazolin-4(3H)-one (I-2)

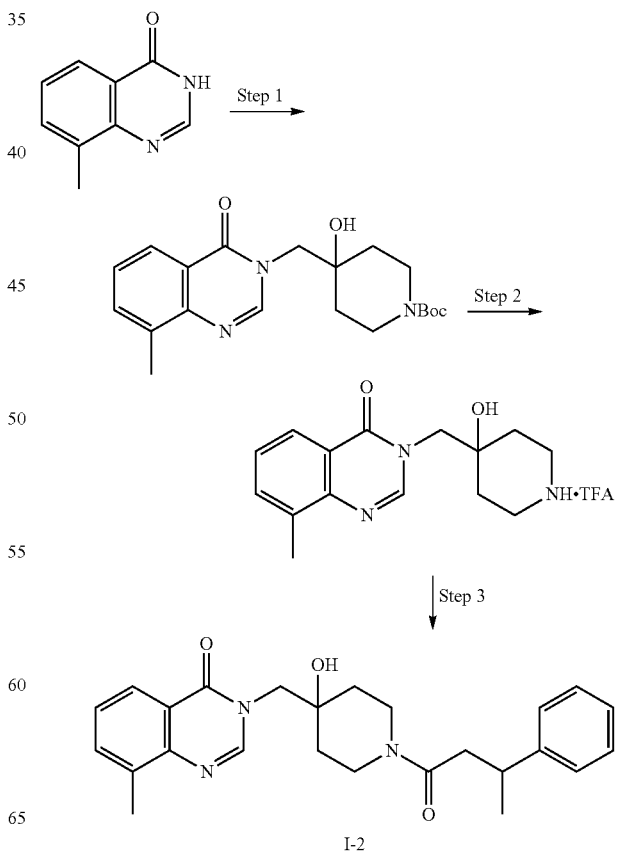

I-2

Step 1. tert-Butyl 4-hydroxy-4-((8-methyl-4-oxoquinazolin-3(4H)-yl)methyl)piperidine-1-carboxylate To a solution of 8-methylquinazolin-4(3H)-one (20 mg, 0.125 mmol) and tert-butyl 1-oxa-6-azaspiro[2.5]octane-6-carboxylate (33 mg, 0.156 mmol) in DMF (0.625 mL) was added cesium carbonate (122 mg, 0.375 mmol). The reaction mixture was stirred at 80° C. for 16 h, then cooled to room temperature, diluted with ethyl acetate (0.5 mL) and washed with water (0.5 mL). The organic layer was concentrated under reduced pressure to afford tert-butyl 4-hydroxy-4-((8-methyl-4-oxoquinazolin-3(4H)-yl)methyl)piperidine-1-carboxylate, which was used without further purification. LCMS: (ESI) m/z 396.29 [M+Na].

Step 2. 3-((4-Hydroxypiperidin-4-yl)methyl)-8-methylquinazolin-4(3H)-one trifluoroacetic Acid Salt To a solution of tert-butyl 4-hydroxy-4-((8-methyl-4-oxoquinazolin-3(4H)-yl)methyl)piperidine-1-carboxylate (Step 1) in 1,2-dichloroethane (0.625 mL) was added trifluoroacetic acid (0.096 mL, 1.25 mmol). The reaction mixture was stirred at 50° C. for 2 h and then concentrated under reduced pressure to afford 3-((4-hydroxypiperidin-4-yl)methyl)-8-methylquinazolin-4(3H)-one trifluoroacetic acid salt, which was used without further purification. LCMS: (ESI) m/z 274.23 [M+H].

Step 3. 3-((4-Hydroxy-1-(3-phenylbutanoyl)piperidin-4-yl)methyl)-8-methylquinazolin-4(3H)-one To 3-((4-hydroxypiperidin-4-yl)methyl)-8-methylquinazolin-4(3H)-one trifluoroacetic acid salt (Step 2) was added 3-phenylbutanoic acid (0.2 M in 1,2-dichloroethane, 0.750 mL, 0.150 mmol), DIPEA (0.109 mL, 0.625 mmol) and HATU (57 mg, 0.150 mmol). The reaction mixture was stirred at 50° C. for 1 h, then cooled to room temperature, diluted with dichloromethane (0.5 mL) and washed with water (0.5 mL). The organic layer was concentrated under reduced pressure and the residue was purified by preparative HPLC to afford 3-((4-hydroxy-1-(3-phenylbutanoyl)piperidin-4-yl)methyl)-8-methylquinazolin-4(3H)-one (I-2, 21.1 mg, 40% over three steps). LCMS (ESI) m/z 420.28 [M+H]. HPLC Column: XBridge BEH C18 OBD Prep Column, 130 Å, 5 μm, 19 mm×50 mm. Mobile phase A: Water with 0.1% ammonium hydroxide/Mobile phase B: Acetonitrile with 0.1% ammonium hydroxide. Gradient: 35% B to 100% B over 6 min. Flow rate: 23 mL/min. Detector: 220 and 254 nm.

Method B

Example 6: 7-Amino-3-((4-hydroxy-1-(3-phenylbutanoyl)piperidin-4-yl)methyl)quinazolin-4(3H)-one (I-4)

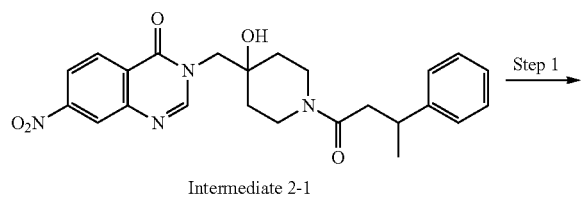

Intermediate 2-1

Step 1

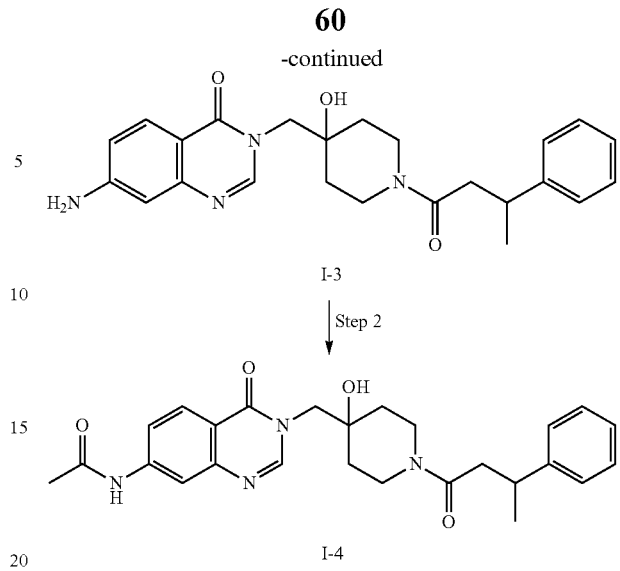

Step 1. 7-Amino-3-((4-hydroxy-1-(3-phenylbutanoyl)piperidin-4-yl)methyl)quinazolin-4(3H)-one Iron (97 mg, 1.74 mmol) and ammonium chloride (4.0 M aqueous, 0.869 mL, 3.47 mmol) were added to a solution of 3-((4-hydroxy-1-(3-phenylbutanoyl)piperidin-4-yl)methyl)-7-nitroquinazolin-4(3H)-one (Intermediate 2-1, 78 mg, 0.17 mmol) in ethanol (1.74 mL). The resulting mixture was heated at 80° C. for 1 h, then diluted with saturated aqueous sodium bicarbonate (2 mL) and extracted with ethyl acetate (4 mL). The organic layer was concentrated under reduced pressure. Some of the residue was used in subsequent reactions without further purification (92% by weight) and the remainder (8% by weight) was purified by preparative HPLC to afford 7-amino-3-((4-hydroxy-1-(3-phenylbutanoyl) piperidin-4-yl)methyl)quinazolin-4(3H)-one (I-3, 0.9 mg, 15%). LCMS (ESI) m/z 421.24 [M+H]. HPLC Column: XBridge BEH C18 OBD Prep Column, 130 Å, 5 μm, 19 mm×50 mm. Mobile phase A: Water with 0.1% ammonium hydroxide/Mobile phase B: Acetonitrile with 0.1% ammonium hydroxide. Gradient: 35% B to 100% B over 6 min. Flow rate: 23 mL/min. Detector: 220 and 254 nm.

Step 2. N-(3-((4-Hydroxy-1-(3-phenylbutanoyl)piperidin-4-yl)methyl)-4-oxo-3,4-dihydro-quinazolin-7-yl)acetamide Acetyl chloride (5 μL, 0.072 mmol) was added to a solution of 7-amino-3-((4-hydroxy-1-(3-phenylbutanoyl)piperidin-4-yl)methyl)quinazolin-4(3H)-one (used crude from Step 1, 17 mg, assumed to be 0.040 mmol) and DIPEA (21 μL, 0.120 mmol) in DCE (0.4 mL). The resulting solution was stirred for 16 h at 50° C. Additional acetyl chloride (5 μL, 0.072 mmol) was added and the mixture was stirred for 1 h at 50° C. The reaction mixture was cooled to room temperature, diluted with saturated aqueous sodium bicarbonate (0.5 mL) and extracted with ethyl acetate (2×0.5 mL). The combined organic extracts were concentrated under reduced pressure and the residue was purified by preparative HPLC to afford N-(3-((4-hydroxy-1-(3-phenylbutanoyl)piperidin-4-yl)methyl)-4-oxo-3,4-dihydro-quinazolin-7-yl)acetamide (I-4, 2.1 mg, 11%). LCMS (ESI) m/z 463.24 [M+H]. HPLC Column: XBridge BEH C18 OBD Prep Column, 130 Å, 5 μm, 19 mm×50 mm. Mobile phase A: Water with 0.1% ammonium hydroxide/Mobile phase B: Acetonitrile with 0.1% ammonium hydroxide. Gradient: 35% B to 100% B over 6 min. Flow rate: 23 mL/min. Detector: 220 and 254 nm.

Method C

Example 7: 3-((1-(4-Fluorobenzoyl)-4-hydroxypiperidin-4-yl)methyl)-8-(4-fluorophenoxy) quinazolin-4(3H)-one (I-10)

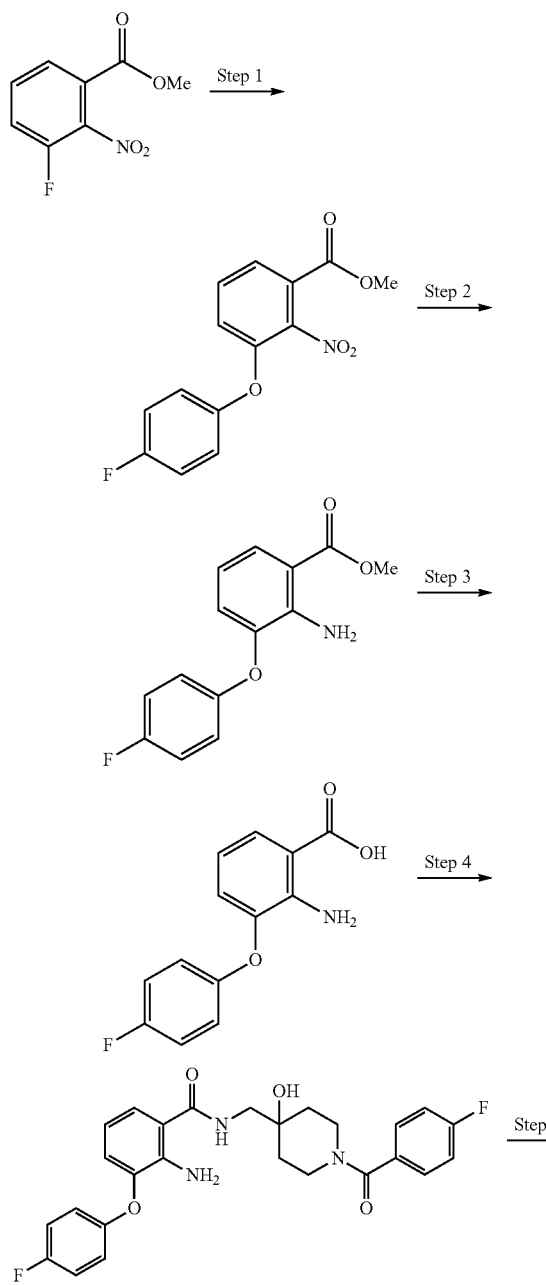

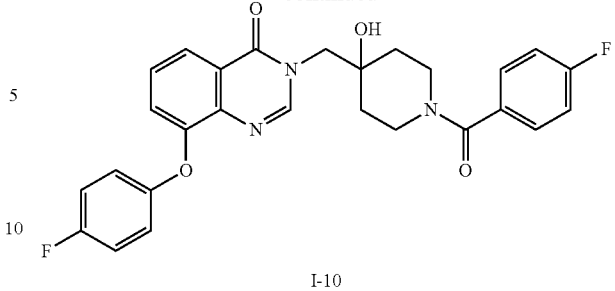

I-10

Step 1. Methyl 3-(4-fluorophenoxy)-2-nitrobenzoate

Methyl 3-fluoro-2-nitrobenzoate (1.50 g, 7.53 mmol), 4-fluorophenol (840 mg, 7.49 mmol), potassium carbonate (5.00 g, 36.2 mmol) and DMF (15 mL) were added to a 100-mL round-bottom flask fitted with a magnetic stir bar. The resulting solution was stirred overnight at 100° C., then cooled to room temperature and diluted with water (40 mL). The resulting solution was extracted with dichloromethane (3×40 mL) and the organic layers were combined, dried over anhydrous sodium sulfate, filtered and concentrated under reduced pressure. The residue was purified by column chromatography eluting with ethyl acetate to afford methyl 3-(4-fluorophenoxy)-2-nitrobenzoate (1.50 g, 68%). LCMS (ESI) m/z 292 [M+H].

Step 2. Methyl 2-amino-3-(4-fluorophenoxy)benzoate

Palladium on carbon (10% wt, 0.20 g) was added to a solution of methyl 3-(4-fluorophenoxy)-2-nitrobenzoate (Step 1, 1.50 g, 5.15 mmol) in ethyl acetate (80 mL) in a 100-mL round-bottom flask fitted with a magnetic stir bar. The mixture was stirred for 16 h at room temperature under an atmosphere of hydrogen then filtered and concentrated under reduced pressure to afford methyl 2-amino-3-(4-fluorophenoxy)benzoate which was used without further purification (1.30 g). LCMS (ESI) m/z 262 [M+H].

Step 3. 2-Amino-3-(4-fluorophenoxy)benzoic Acid

Methyl 2-amino-3-(4-fluorophenoxy)benzoate (Step 2, 300 mg, assumed to be 1.19 mmol), methanol (10 mL), lithium hydroxide (500 mg, 20.9 mmol) and water (3 mL) were added to a 100-mL round-bottom flask fitted with a magnetic stir bar. The resulting solution was stirred for 4 h at room temperature, then acidified to pH 2 with hydrochloric acid (1.0 M aqueous). The resulting solution was extracted with dichloromethane (3×20 mL) and the organic layers were combined, dried over anhydrous sodium sulfate, filtered and concentrated under reduced pressure to afford 2-amino-3-(4-fluorophenoxy)benzoic acid (0.2 g) which was used in next step without further purification. LCMS (ESI) m/z 248 [M+H]

Step 4. 2-Amino-N-((1-(4-fluorobenzoyl)-4-hydroxypiperidin-4-yl)methyl)-3-(4-fluoro-phenoxy) benzamide 2-Amino-3-(4-fluorophenoxy)benzoic acid (Step 3, 0.1 g, assumed to be 0.59 mmol), (4-(aminomethyl)-4-hydroxypiperidin-1-yl)(4-fluorophenyl)methanone (Intermediate 2-4, 122 mg, 0.48 mmol), HATU (186 mg, 0.49 mmol), DIPEA (155 mg, 1.20 mmol) and dichloromethane (10 mL) were added to a 100-mL round-bottom flask fitted with a magnetic stir bar. The resulting solution was stirred for 2 h at room temperature and then concentrated under reduced pressure. The crude product was purified by preparative TLC eluting with ethyl acetate to afford 2-amino-N-((1-(4-fluorobenzoyl)-4-hydroxypiperidin-4-yl)methyl)-3-(4-fluoro-phenoxy)benzamide (0.13 g, 56%). LCMS (ESI) m/z 482 [M+H].

Step 5. 3-((1-(4-Fluorobenzoyl)-4-hydroxypiperidin-4-yl)methyl)-8-(4-fluorophenoxy) quinazolin-4(3H)-one 2-Amino-N-((1-(4-fluorobenzoyl)-4-hydroxypiperidin-4-yl)methyl)-3-(4-fluorophenoxy)benzamide (Step 4, 130 mg, 0.28 mmol) and trimethyl orthoformate (15 mL) were added to a 100-mL round-bottom flask fitted with a magnetic stir bar. The resulting solution was stirred overnight at 100° C. The resulting mixture was concentrated under reduced pressure and purified by preparative HPLC to afford 3-((1-(4-fluorobenzoyl)-4-hydroxypiperidin-4-yl)methyl)-8-(4-fluorophenoxy)quinazolin-4(3H)-one (I-10, 30 mg, 21%). LCMS (ESI) m/z 492.22 [M+H]. $^1$H NMR (400 MHz, DMSO-d$^6$) δ 8.21 (s, 1H), 7.99-7.96 (m, 1H), 7.53-7.45 (m, 3H), 7.42-7.39 (m, 1H), 7.29-7.21 (m, 2H), 7.19-7.16 (m, 2H), 7.02-6.97 (m, 2H), 5.01 (s, 1H), 4.18-4.17 (m, 1H), 4.05 (s, 2H), 3.38-3.32 (m, 1H), 3.30-2.90 (m, 2H), 1.63-1.62 (m, 2H), 1.53-1.50 (m, 2H) ppm. HPLC Column: Waters HSS C18, 1.8 μm, 2.1 mm×50 mm. XBridge BEH C18 OBD Prep Column, 130 Å, 5 μm, 19 mm×50 mm. Mobile phase A: Ammonium bicarbonate (10 mM aqueous)/Mobile phase B: Acetonitrile. Gradient: 5% B to 95% B over 4 min. Detector: 220 and 254 nm.

Method D

Example 8: 3-((1-(4-Fluorobenzoyl)-4-hydroxypiperidin-4-yl)methyl)-8-(4-fluorophenoxy) quinazolin-4(3H)-one (I-12)

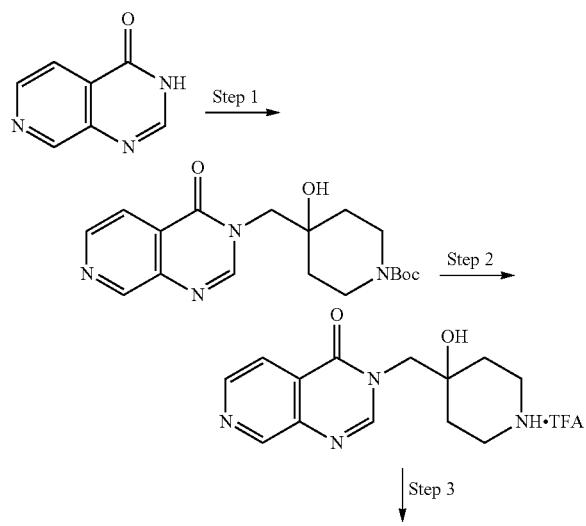

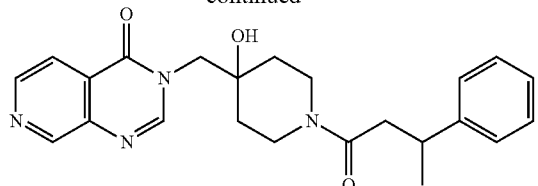

I-12

Step 1. tert-Butyl 4-hydroxy-4-((4-oxopyrido[3,4-d]pyrimidin-3(4H)-yl)methyl)piperidine-1-carboxylate To a solution of pyrido[3,4-d]pyrimidin-4(3H)-one (12 mg, 0.080 mmol) and tert-butyl 1-oxa-6-azaspiro[2.5]octane-6-carboxylate (21 mg, 0.10 mmol) in DMF (0.400 mL) was added cesium carbonate (78 mg, 0.240 mmol). The reaction mixture was stirred at 80° C. for 16 h, then cooled to room temperature, diluted with ethyl acetate (0.5 mL) and washed with water (0.5 mL). The organic layer was concentrated under reduced pressure to afford tert-butyl 4-hydroxy-4-((4-oxopyrido[3,4-d]pyrimidin-3 (4H)-yl)methyl)piperidine-1-carboxylate, which was used without further purification. LCMS: (ESI) m/z 361.19 [M+H].

Step 2. 3-((4-Hydroxypiperidin-4-yl)methyl)pyrido[3,4-d]pyrimidin-4(3H)-one trifluoroacetic Acid Salt To a solution of tert-butyl 4-hydroxy-4-((4-oxopyrido[3,4-d]pyrimidin-3(4H)-yl)methyl)piperidine-1-carboxylate (Step 1) in 1,2-dichloroethane (0.2 mL) was added trifluoroacetic acid (0.062 mL, 0.80 mmol). The reaction mixture was stirred at 50° C. for 2 h and then concentrated under reduced pressure to afford 3-((4-hydroxypiperidin-4-yl)methyl)pyrido[3,4-d]pyrimidin-4(3H)-one trifluoroacetic acid salt, which was used without further purification. LCMS: (ESI) m/z 261.14 [M+H].

Step 3. 3-((4-hydroxy-1-(3-phenylbutanoyl)piperidin-4-yl)methyl)pyrido[3,4-d]pyrimidin-4(3H)-one To 3-((4-hydroxypiperidin-4-yl)methyl)pyrido[3,4-d]pyrimidin-4(3H)-one trifluoroacetic acid salt (Step 2) was added 3-phenylbutanoic acid (0.2 M in 1,2-dichloroethane, 0.480 mL, 0.096 mmol), DIPEA (0.070 mL, 0.400 mmol) and HATU (37 mg, 0.096 mmol). The reaction mixture was stirred at 50° C. for 1 h, then cooled to room temperature, diluted with dichloromethane (0.5 mL) and washed with water (0.5 mL). The organic layer was concentrated under reduced pressure and the residue was purified by preparative HPLC to afford 3-((4-hydroxy-1-(3-phenylbutanoyl)piperidin-4-yl)methyl)pyrido[3,4-d]pyrimidin-4(3H)-one (I-12, 17 mg, 52% over three steps). LCMS (ESI) m/z 407.24 [M+H]. HPLC Column: XBridge BEH C18 OBD Prep Column, 130 Å, 5 μm, 19 mm×50 mm. Mobile phase A: Water with 0.1% ammonium hydroxide/Mobile phase B: Acetonitrile with 0.1% ammonium hydroxide. Gradient: 35% B to 100% B over 6 min. Flow rate: 23 mL/min. Detector: 220 and 254 nm.

Biochemical Assays

Example 9: USP7 Assay A (Ubitquin-Rhodamine 110 Assay)

Each assay was performed in a final volume of 15 μL in assay buffer containing 20 mM Tris-HCl (pH 8.0, (1M Tris-HCl, pH 8.0 solution; Corning 46-031-CM)), 1 mM GSH (L-Glutathione reduced; Sigma # G4251), 0.03% BGG (0.22 µM filtered, Sigma, # G7516-25G), and 0.01% Triton X-100 (Sigma, # T9284-10L). Nanoliter quantities of either an 8-point or 10-point, 3-fold serial dilution in DMSO was pre-dispensed into assay plates (Perkin Elmer, ProxiPlate-384 F Plus, #6008269) for a final test concentration range of either 25 µM to 11 nM or 25 µM to 1.3 nM, respectively. The final concentration of the enzyme (USP7, construct USP7 (208-1102) 6*His, Viva Biotech) in the assay was 62.5 pM. Final substrate (Ub-Rh110; Ubiquitin-Rhodamine 110, R&D Systems # U-555) concentration was 25 nM with [Ub-Rh110]<<Km. 5 µL of 2× enzyme was added to assay plates (pre-stamped with compound) preincubated with USP7 for 30 min and then 5 µL of 2×Ub-Rh110 was added to assay plates. Plates were incubated stacked for 20 min at room temperature before 5 µL of stop solution (final concentration of 10 mM citric acid in assay buffer (Sigma, #251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example 10: USP7 Assay B (Ubitquin-Rhodamine 110 Assay)

Each assay was performed in a final volume of 20 µL in assay buffer containing 20 mM Tris-HCl (pH 8.0, (1M Tris-HCl, pH 8.0 solution; Corning 46-031-CM)), 2 mM $CaCl_2$ (1M Calcium Chloride solution; Sigma #21114) 1 mM GSH (L-Glutathione reduced; Sigma # G4251), 0.01% Prionex (0.22 µM filtered, Sigma # G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 µM ($DMSO_{(fc)}$=0.5%). For follow-up studies, 250 nL of an 8-point, 3-fold serial dilution in DMSO was pre-dispensed into assay plates for a final test concentration of 25 µM-11 nM (1.25% DMSO final concentration). Unless otherwise indicated, all follow-up assays were run on triplecate plates. Enzyme (USP7, construct Met (208-1102)-TEV-6*His; Viva Q93009-1) concentration and incubation times were optimized for the maximal signal-to-background while maintaining initial velocity conditions at a fixed substrate concentration. The final concentration of the enzyme in the assay was either 75 pM or 250 pM. Final substrate (Ub-Rh110; Ubiquitin-Rhodamine 110, R&D Systems (biotechne) # U-555) concentration was 25 nM with [Ub-Rh110]<<Km. Pre-stamped with compounds were either not preincubated or preincubated with USP7 between 30 to 120 min prior to the addition of 10 µL of 2×Ub-Rh110 to compound plates. Plates were incubated stacked for either 23 or 45 min at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

Data from USP7 Assays A and B were reported as percent inhibition (inh) compared with control wells based on the following equation: % $inh=1-((FLU-Ave_{Low})/(Ave_{High}-Ave_{Low}))$ where FLU=measured Fluorescence. $Ave_{Low}$=average Fluorescence of no enzyme control (n=16). $Ave_{High}$=average Fluorescence of DMSO control (n=16). $IC_{50}$ values were determined by curve fitting of the standard 4 parameter logistic fitting algorithm included in the Activity Base software package: IDBS XE Designer Model205. Data is fitted using the Levenburg Marquardt algorithm. $IC_{50}$ data from USP7 Assays A and B for the compounds of the disclosure can be found in the Table below.

TABLE 1

USP7 activity of compounds of the disclosure in USP7 assay A and B.
USP7 Activity of compounds of the present disclosure in USP Assays A and B.

| Example | Method of Synthesis | Intermediate In Synthesis | LCMS: (ESI) m/z [M + H] | HPLC Retention time/min | IC50 (µM) |
|---|---|---|---|---|---|
| I-1  | A | —   | 436.27 | 1.2  | ++++ |
| I-2  | A | —   | 420.28 | 1.3  | ++++ |
| I-3  | B | 2-1 | 421.24 | 1.01 | ++++ |
| I-4  | B | 2-1 | 463.24 | 1.03 | ++++ |
| I-5  | A | —   | 436.16 | 1.2  | ++++ |
| I-6  | A | —   | 420.17 | 1.31 | ++++ |
| I-7  | A | —   | 509.19 | 1.5  | ++   |
| I-8  | A | 2-2 | 440.15 | 1.33 | +    |
| I-9  | A | 2-3 | 440.16 | 1.38 | ++   |
| I-10 | C | 2-4 | 492.22 | 1.38 | ++   |
| I-11 | D | —   | 407.28 | 0.97 | +    |
| I-12 | D | —   | 407.24 | 0.99 | ++   |
| I-13 | D | —   | 407.16 | 0.92 | +++  |

++++ indicates an $IC_{50}$ of less than about 0.2 µM,
+++ indicates an $IC_{50}$ between about 0.2 µM and about 1 µM,
++ indicates an $IC_{50}$ between about 1 µM and about 10 µM, and
+ indicates an $IC_{50}$ greater than 10 µM.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of inhibiting USP7 in a patient suffering from a disease or disorder associated with modulation of USP7, comprising administering to the patient an effective amount of a compound of Formula (I):

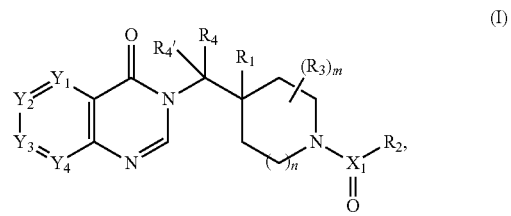

or a pharmaceutically acceptable salt thereof, wherein:
$X_1$ is C, S, or S(O);
$Y_1$ is N or CH;
$Y_2$ is N or $CR_5$;
$Y_3$ is N or $CR_6$;
$Y_4$ is N or $CR_7$;
$R_1$ is OH;
$R_2$ is $(C_1-C_6)$ alkyl or $(C_6-C_{14})$ aryl, wherein the alkyl or aryl are optionally substituted with one to three $R_8$;
$R_4$ and $R_{4'}$ are independently H;
$R_5$ is H;

$R_6$ is H, $(C_1$-$C_6)$ alkyl, $(C_1$-$C_6)$ alkoxy, halogen, —$NH_2$, —$NHC(O)(C_1$-$C_6)$ alkyl, or $(C_6$-$C_{14})$ aryl, wherein the alkyl or aryl are optionally substituted with one to three $R_{13}$;

$R_7$ is H, $(C_1$-$C_6)$ alkyl, $(C_6$-$C_{14})$ aryl, or —O—$(C_6$-$C_{14})$ aryl, wherein the alkyl or aryl are optionally substituted with one to three $R_{14}$;

each $R_8$ is independently $(C_1$-$C_6)$ alkyl, halogen, or —$(C_0$-$C_4)$-alkylene-$(C_6$-$C_{14})$ aryl, wherein the alkyl or aryl are optionally substituted with one to three $R_9$;

or two $R_8$ together when on adjacent atoms form a $(C_3$-$C_8)$ cycloalkyl optionally substituted with one to three $R_9$;

each $R_9$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, or —$(C_0$-$C_3)$-alkylene-$(C_6$-$C_{14})$ aryl, wherein alkyl or aryl are optionally substituted with one to three $R_{19}$;

each $R_{13}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —$NH_2$, $(C_1$-$C_6)$ alkylamino, di$(C_1$-$C_6)$ alkylamino, or heterocycloalkyl independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl; wherein the alkyl and heterocycloalkyl are optionally substituted with one to three $R_{15}$;

each $R_{14}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —$NH_2$, —$C(O)(C_1$-$C_6)$ alkyl, —$S(O)_q(C_1$-$C_6)$ alkyl, $(C_1$-$C_6)$ alkylamino, or di$(C_1$-$C_6)$ alkylamino;

each $R_{15}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, —$C(O)(C_1$-$C_6)$ alkyl, —$S(O)_q(C_1$-$C_6)$ alkyl, —$NH_2$, $(C_1$-$C_6)$ alkylamino, di$(C_1$-$C_6)$ alkylamino, —OH, or CN;

each $R_{19}$ is independently at each occurrence $(C_1$-$C_6)$ alkyl, $(C_1$-$C_6)$ alkoxy, $(C_1$-$C_6)$ haloalkyl, $(C_1$-$C_6)$ haloalkoxy, halogen, —OH, or CN;

m is 0;

n is 1;

q is independently at each occurrence 0, 1, or 2; and provided that
(a) when $R_2$ is optionally substituted $(C_1$-$C_6)$ alkyl, $R_5$ is H; and $R_7$ is H; then $R_6$ is not chloro;
(b) $R_5$, $R_6$, and $R_7$ are not all simultaneously H; and
(c) the compound is further characterized by any one or more of the following:
  i. at least one of $Y_1$, $Y_2$, $Y_3$, or $Y_4$ is N;
  ii. at least one of $R_6$ or $R_7$ is an optionally substituted $(C_6$-$C_{14})$ aryl;
  iii. $R_6$ is $(C_1$-$C_6)$ alkyl, —$NHC(O)(C_1$-$C_6)$ alkyl, or $(C_6$-$C_{14})$ aryl, wherein the alkyl or aryl of $R_6$ is substituted with a $R_{13}$ that is $(C_1$-$C_6)$ alkoxy, $(C_1$-$C_6)$ haloalkyl, $(C_1$-$C_6)$ haloalkoxy, halogen, CN, —OH, —$NH_2$, $(C_1$-$C_6)$ alkylamino, or di$(C_1$-$C_6)$ alkylamino;
  iv. $R_6$ is $(C_1$-$C_6)$ alkyl, —$NHC(O)(C_1$-$C_6)$ alkyl, or $(C_6$-$C_{14})$ aryl, wherein the alkyl or aryl of $R_6$ is substituted with a $R_{13}$ that is $(C_1$-$C_6)$ alkyl or a heterocycloalkyl, independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl; wherein the heterocycloalkyl is substituted with one to three $R_{15}$; or
  V. $R_7$ is H, $(C_1$-$C_6)$ alkyl, $(C_6$-$C_{14})$ aryl, or —O—$(C_6$-$C_{14})$ aryl, wherein the alkyl or aryl of $R_7$ is substituted with a $R_{14}$ that is $(C_1$-$C_6)$ alkoxy, $(C_1$-$C_6)$ haloalkyl, $(C_1$-$C_6)$ haloalkoxy, halogen, CN, —OH, —$NH_2$, —$C(O)(C_1$-$C_6)$ alkyl, $S(O)_q(C_1$-$C_6)$ alkyl, $(C_1$-$C_6)$ alkylamino, or di$(C_1$-$C_6)$ alkylamino.

2. The method of claim 1, wherein:
$R_2$ is $(C_1$-$C_6)$ alkyl or $(C_6$-$C_{14})$ aryl, wherein the alkyl or aryl are optionally substituted with one to two $R_8$;

each $R_8$ is independently halogen or —$(C_0$-$C_4)$-alkylene-$(C_6$-$C_{14})$ aryl, wherein the aryl is optionally substituted with one to three $R_9$; or two $R_8$ together when on adjacent atoms form a $(C_3$-$C_8)$ cycloalkyl optionally substituted with one to three $R_9$; and each $R_9$ is —$(C_0$-$C_3)$-alkylene-$(C_6$-$C_{14})$ aryl.

3. The method of claim 2, wherein $R_2$ is $(C_1$-$C_6)$ alkyl substituted with one $R_8$; and $R_8$ is —$(C_0$-$C_4)$-alkylene-$(C_6$-$C_{14})$ aryl.

4. The method of claim 2, wherein $R_2$ is $(C_6$-$C_{14})$ aryl.

5. The method of claim 4, wherein two $R_8$ together when on adjacent atoms form a $(C_3$-$C_8)$ cycloalkyl optionally substituted with one to three $R_9$.

6. The method of claim 5, wherein the $(C_3$-$C_8)$cycloalkyl formed by two $R_8$ together on adjacent atoms is substituted with one $R_9$ and $R_9$ is —$(C_0$-$C_3)$-alkylene-$(C_6$-$C_{14})$ aryl.

7. The method of claim 2, wherein
$R_6$ is H;
$R_7$ is $(C_1$-$C_6)$ alkyl, $C_6$-aryl, or —O—$C_6$-aryl, wherein the alkyl or aryl are optionally substituted with one to three $R_{14}$; and
each $R_{14}$ is independently $(C_1$-$C_6)$ alkyl, $(C_1$-$C_6)$ alkoxy, $(C_1$-$C_6)$ haloalkyl, $(C_1$-$C_6)$ haloalkoxy, halogen, CN, —OH, —$NH_2$, $(C_1$-$C_6)$ alkylamino, or di$(C_1$-$C_6)$ alkylamino.

8. The method of claim 7, wherein $R_{14}$ is halogen.

9. The method of claim 8, wherein $R_7$ is $C_6$-aryl.

10. The method of claim 8, wherein $R_7$ is —O—$C_6$-aryl.

11. The method of claim 2, wherein
$R_6$ is $(C_1$-$C_6)$ alkyl, $(C_1$-$C_6)$ alkoxy, halogen, —$NH_2$, —$NHC(O)(C_1$-$C_6)$ alkyl, or $(C_6$-$C_{14})$ aryl, wherein the alkyl or aryl are optionally substituted with one to three $R_{13}$;

$R_{13}$ is independently $(C_1$-$C_6)$ alkyl or heterocycloalkyl selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl;

wherein the alkyl and heterocycloalkyl are optionally substituted with one to three $R_{15}$;

each $R_{15}$ is independently $(C_1$-$C_6)$ alkyl; and $R_7$ is H.

12. The method of claim 11, wherein $R_6$ is NHC(O)($C_1$-$C_6$) alkyl.

13. The method of claim 1, wherein the compound is of formula (Ic):

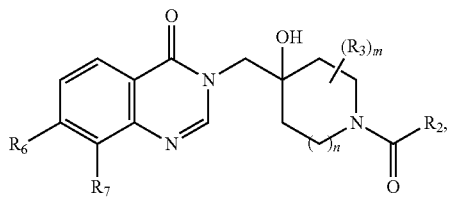

(Ic)

or a pharmaceutically acceptable salt thereof; wherein:
- $R_2$ is ($C_1$-$C_6$) alkyl or ($C_6$-$C_{14}$) aryl, wherein the alkyl or aryl are optionally substituted with one to three $R_8$;
- $R_6$ is H, ($C_1$-$C_6$) alkyl, ($C_1$-$C_6$) alkoxy, halogen, —$NH_2$, —NHC(O)($C_1$-$C_6$) alkyl, or ($C_6$-$C_{14}$) aryl, wherein the alkyl or aryl are optionally substituted with one to three $R_{13}$;
- $R_7$ is H, ($C_1$-$C_6$) alkyl, ($C_6$-$C_{14}$) aryl, or —O—($C_6$-$C_{14}$) aryl, wherein the alkyl or aryl are optionally substituted with one to three $R_{14}$;
- each $R_8$ is independently ($C_1$-$C_6$) alkyl, halogen, or —($C_0$-$C_4$)-alkylene-($C_6$-$C_{14}$) aryl, wherein the alkyl or aryl are optionally substituted with one to three $R_9$;
- or two $R_8$ together when on adjacent atoms form a ($C_3$-$C_8$) cycloalkyl optionally substituted with one to three $R_9$;
- each $R_9$ is independently ($C_1$-$C_6$) alkyl, ($C_1$-$C_6$) alkoxy, ($C_1$-$C_6$) haloalkyl, ($C_1$-$C_6$) haloalkoxy, halogen, or —($C_0$-$C_3$)-alkylene-($C_6$-$C_{14}$) aryl, wherein alkyl and aryl are optionally substituted with one to three $R_{19}$;
- each $R_{13}$ is independently ($C_1$-$C_6$) alkyl, ($C_1$-$C_6$) alkoxy, ($C_1$-$C_6$) haloalkyl, ($C_1$-$C_6$) haloalkoxy, halogen, CN, —OH, —$NH_2$, ($C_1$-$C_6$) alkylamino, di($C_1$-$C_6$) alkylamino, or heterocycloalkyl independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl;
- wherein the alkyl and heterocycloalkyl are optionally substituted with one to three $R_{15}$;
- each $R_{14}$ is independently ($C_1$-$C_6$) alkyl, ($C_1$-$C_6$) alkoxy, ($C_1$-$C_6$) haloalkyl, ($C_1$-$C_6$) haloalkoxy, halogen, CN, —OH, —$NH_2$, —C(O)($C_1$-$C_6$) alkyl, —S(O)$_q$($C_1$-$C_6$) alkyl, ($C_1$-$C_6$) alkylamino, or di($C_1$-$C_6$) alkylamino;
- each $R_{15}$ is independently ($C_1$-$C_6$) alkyl, ($C_1$-$C_6$) alkoxy, ($C_1$-$C_6$) haloalkyl, ($C_1$-$C_6$) haloalkoxy, halogen, —C(O)($C_1$-$C_6$) alkyl, —S(O)$_q$($C_1$-$C_6$) alkyl, —$NH_2$, ($C_1$-$C_6$) alkylamino, di($C_1$-$C_6$) alkylamino, —OH, or CN; and
- each $R_{19}$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, —OH, or CN.

14. The method of claim 13, wherein
- $R_2$ is ($C_1$-$C_6$) alkyl, optionally substituted with one $R_8$; and
- $R_8$ is independently —($C_0$-$C_4$)-alkylene-($C_6$) aryl, wherein the aryl are optionally substituted with one to three $R_9$.

15. The method of claim 14, wherein $R_8$ is not substituted with $R_9$.

16. The method of claim 15, wherein
- $R_6$ is ($C_1$-$C_6$) alkyl, ($C_1$-$C_6$) alkoxy, halogen, —$NH_2$, —NHC(O)($C_1$-$C_6$) alkyl, or ($C_6$-$C_{14}$) aryl, wherein the alkyl or aryl are optionally substituted with one to three $R_{13}$; and
- $R_7$ is H.

17. The method of claim 16, wherein $R_6$ is ($C_1$-$C_6$) alkyl $NH_2$, or NHC(O)($C_1$-$C_6$) alkyl wherein the alkyl is optionally substituted with one to three $R_{13}$.

18. The method of claim 17, wherein $R_{13}$ is a heterocycloalkyl independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl; optionally substituted with one to three $R_{15}$.

19. The method of claim 18, wherein $R_{15}$ is ($C_1$-$C_6$) alkyl.

20. The method of claim 15, wherein
- $R_6$ is H; and
- $R_7$ is ($C_1$-$C_6$) alkyl, ($C_6$-$C_{14}$) aryl, or —O—($C_6$-$C_{14}$) aryl, wherein the alkyl or aryl are optionally substituted with one to three $R_{14}$.

21. The method of claim 20, wherein $R_7$ is ($C_6$-$C_{14}$) aryl or —O—($C_6$-$C_{14}$) aryl, wherein the aryl is optionally substituted with one $R_{14}$, wherein $R_{14}$ is halogen.

22. The method of claim 1, selected from formula (Id) or formula (Ie):

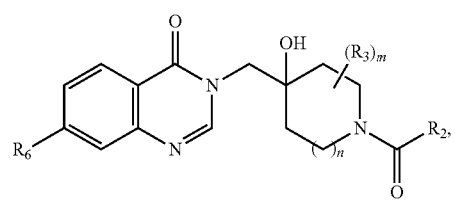

(Id)

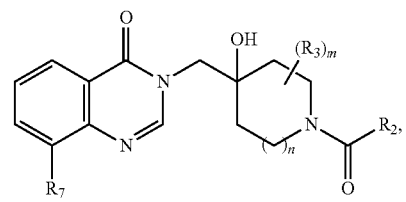

(Ie)

or a pharmaceutically acceptable salt thereof; wherein:
- $R_2$ is ($C_1$-$C_6$) alkyl, optionally substituted with $R_8$;
- $R_6$ is ($C_1$-$C_6$) alkyl, ($C_1$-$C_6$) alkoxy, halogen, —$NH_2$, —NHC(O)($C_1$-$C_6$) alkyl, ($C_6$-$C_{14}$) aryl, wherein the alkyl or aryl are optionally substituted with one to three $R_{13}$;
- $R_7$ is ($C_1$-$C_6$) alkyl, ($C_6$-$C_{14}$) aryl, or —O—($C_6$-$C_{14}$) aryl, wherein the alkyl or aryl are optionally substituted with one to three $R_{14}$;

$R_8$ is independently $(C_1-C_6)$ alkyl, halogen, or —$(C_0-C_4)$-alkylene-$(C_6-C_{14})$ aryl, wherein the alkyl or aryl are optionally substituted with one to three $R_9$;

each $R_{13}$ is independently $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, $(C_1-C_6)$ alkylamino, di$(C_1-C_6)$ alkylamino, or heterocycloalkyl independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl; wherein the alkyl and heterocycloalkyl are optionally substituted with one to three $R_{15}$;

each $R_{14}$ is independently $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —C(O)$(C_1-C_6)$ alkyl, —S(O)$_q$$(C_1-C_6)$ alkyl, $(C_1-C_6)$ alkylamino, or di$(C_1-C_6)$ alkylamino;

each $R_{15}$ is independently $(C_1-C_6)$ alkyl, $(C_1-C_6)$ alkoxy, $(C_1-C_6)$ haloalkyl, $(C_1-C_6)$ haloalkoxy, halogen, —C(O)$(C_1-C_6)$ alkyl, —S(O)$_q$$(C_1-C_6)$ alkyl, —NH$_2$, $(C_1-C_6)$ alkylamino, di$(C_1-C_6)$ alkylamino, —OH, or CN; and each $R_{19}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, or CN.

23. The method of claim 22, wherein $R_2$ is $(C_1-C_6)$ alkyl substituted with $R_8$; and $R_8$ is —$(C_0-C_4)$-alkylene-$(C_6-C_{14})$ aryl.

24. The method of claim 23, wherein:

$R_6$ is $(C_1-C_6)$ alkyl, $(C_1-C_6)$ alkoxy, —NH$_2$, —NHC(O)$(C_1-C_6)$ alkyl, wherein the alkyl is optionally substituted with one to three $R_{13}$; and $R_7$ is $(C_1-C_6)$ alkyl, $(C_6-C_{14})$ aryl, or —O—$(C_6-C_{14})$ aryl, wherein the alkyl or aryl are optionally substituted with one to three $R_{14}$.

25. The method of claim 24, wherein the compound is of formula (Ie) wherein $R_7$ is $(C_6-C_{14})$ aryl or —O—$(C_6-C_{14})$ aryl, wherein the aryl is optionally substituted with one to three $R_{14}$; and each $R_{14}$ is independently $(C_1-C_6)$ alkyl or halogen.

26. The method of claim 24, wherein the compound is of formula (Ie) wherein $R_7$ is $(C_1-C_6)$ alkyl.

27. The method of claim 1, wherein the patient is suffering from cancer, a neurodegenerative disease, an immunological disorder, diabetes, a bone and joint disease, osteoporosis, an arthritis, an inflammatory disorder, a cardiovascular disease, an ischemic disease, a viral infection or disease, a viral infectivity and/or latency, or a bacterial infection or disease.

28. The method of claim 27, wherein the patient is suffering from liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid or vaginal cancer or Epstein-Barr Virus-associated nasopharyngeal carcinoma, gastric cancer, rectal cancer, thyroid cancer, Hodgkin lymphoma, or diffuse large B-cell lymphoma; or Alzheimer's disease, multiple sclerosis, Huntington's disease, infectious meningitis, encephalomyelitis, Parkinson's disease, amyotrophic lateral sclerosis, or encephalitis; or herpes simplex-1 or -2 viral infections, hepatitis A, hepatitis C, SARS coronavirus infection and disease, Epstein-Barr virus, rhinoviral infections and diseases, adenoviral infections and diseases, or poliomyelitis; or Type II diabetes, insulin resistance cardiovascular disease, arrhythmia, atherosclerosis, coronary artery disease, hypertriglyceridemia, dyslipidemia, retinopathy, nephropathy, neuropathy, or macular edema; or ileitis, ulcerative colitis, Barrett's syndrome, or Crohn's disease.

* * * * *